United States Patent
Soni et al.

(10) Patent No.: US 10,583,113 B2
(45) Date of Patent: Mar. 10, 2020

(54) CROMOLYN COMPOSITIONS FOR TREATMENT OF PULMONARY FIBROSIS

(71) Applicant: Respivant Sciences, GmbH, Basel (CH)

(72) Inventors: Pravin Soni, Sunnyvale, CA (US); William Gerhart, Del Mar, CA (US); Ahmet Tutuncu, Del Mar, CA (US); Robert Craig Armstrong, San Diego, CA (US)

(73) Assignee: Respivant Sciences GmbH, Basel (CH)

( * ) Notice: Subject to any disclaimer, the term of this patent is extended or adjusted under 35 U.S.C. 154(b) by 0 days.

(21) Appl. No.: 16/370,677

(22) Filed: Mar. 29, 2019

(65) Prior Publication Data

US 2019/0224162 A1     Jul. 25, 2019

Related U.S. Application Data

(63) Continuation of application No. PCT/US2017/053327, filed on Sep. 25, 2017.

(Continued)

(51) Int. Cl.
| | |
|---|---|
| *A61K 31/353* | (2006.01) |
| *A61K 47/02* | (2006.01) |
| *A61K 9/00* | (2006.01) |
| *A61K 31/352* | (2006.01) |
| *A61P 11/00* | (2006.01) |

(Continued)

(52) U.S. Cl.
CPC .......... *A61K 31/353* (2013.01); *A61K 9/0075* (2013.01); *A61K 9/0078* (2013.01); *A61K 31/352* (2013.01); *A61K 45/06* (2013.01); *A61K 47/02* (2013.01); *A61K 47/10* (2013.01);

(Continued)

(58) Field of Classification Search
CPC ................ A61K 31/277; A61K 31/352; A61K 31/4422; A61K 31/4535; A61K 31/4741; A61K 47/02; A61K 47/183; A61K 9/0075; A61K 9/0078; A61K 9/12; A61M 11/00; A61M 11/005; A61M 11/041; A61M 11/06; A61M 15/00; A61M 15/009; A61M 2202/064

See application file for complete search history.

(56) References Cited

U.S. PATENT DOCUMENTS

| | | |
|---|---|---|
| 3,419,578 A | 12/1968 | Fitzmaurice et al. |
| 3,598,122 A | 8/1971 | Zaffaroni |

(Continued)

FOREIGN PATENT DOCUMENTS

| | | |
|---|---|---|
| AU | 2012238334 A1 | 11/2012 |
| AU | 2013200711 A1 | 2/2013 |

(Continued)

OTHER PUBLICATIONS

Asmus et al., "Pulmonary function response to EDTA, and additive nebulized bronchodilators," J. Allergy Clin Immunology, 107(1):68-71 (2001).

(Continued)

*Primary Examiner* — Savitha M Rao
(74) *Attorney, Agent, or Firm* — Fish & Richardson P.C.

(57) ABSTRACT

The disclosure provides a method of treating pulmonary fibrosis, including idiopathic pulmonary fibrosis, in a comprising administering to the subject a pharmaceutical composition comprising from about 1% by weight to about 99% by weight of cromolyn sodium with an inhalation device.

20 Claims, 11 Drawing Sheets

Related U.S. Application Data

(60) Provisional application No. 62/417,887, filed on Nov. 4, 2016, provisional application No. 62/405,587, filed on Oct. 7, 2016.

(51) Int. Cl.
*A61K 47/18* (2017.01)
*A61K 47/26* (2006.01)
*A61K 45/06* (2006.01)
*A61K 47/10* (2017.01)

(52) U.S. Cl.
CPC ............ *A61K 47/183* (2013.01); *A61K 47/26* (2013.01); *A61P 11/00* (2018.01)

(56) References Cited

U.S. PATENT DOCUMENTS

| | | |
|---|---|---|
| 3,598,123 A | 8/1971 | Zaffaroni |
| 3,683,320 A | 8/1972 | Woods et al. |
| 3,686,320 A | 8/1972 | Fitzmaurice et al. |
| 3,686,412 A | 8/1972 | Fitzmaurice et al. |
| 3,710,795 A | 1/1973 | Higuchi et al. |
| 3,720,690 A | 3/1973 | King et al. |
| 3,731,683 A | 5/1973 | Zaffaroni |
| 3,742,951 A | 7/1973 | Zaffaroni |
| 3,777,033 A | 12/1973 | Fitzmaurice et al. |
| 3,790,580 A | 2/1974 | Johnson et al. |
| 3,814,097 A | 6/1974 | Ganderton et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,031,894 A | 6/1977 | Urquhart et al. |
| 4,060,084 A | 11/1977 | Chandrasekaran et al. |
| 4,067,992 A | 1/1978 | Kingsley et al. |
| 4,069,307 A | 1/1978 | Higuchi et al. |
| 4,077,407 A | 3/1978 | Theeuwes et al. |
| 4,151,273 A | 4/1979 | Riegelman et al. |
| 4,152,448 A | 5/1979 | Wardell |
| 4,189,571 A | 2/1980 | Bodor et al. |
| 4,201,211 A | 5/1980 | Chandrasekaran et al. |
| 4,229,447 A | 10/1980 | Porter |
| 4,230,105 A | 10/1980 | Harwood |
| 4,268,519 A | 5/1981 | Turner |
| 4,292,299 A | 9/1981 | Suzuki et al. |
| 4,292,303 A | 9/1981 | Keith et al. |
| 4,343,789 A | 8/1982 | Kawata et al. |
| 4,362,742 A | 12/1982 | Sullivan |
| 4,476,116 A | 10/1984 | Anik |
| 4,496,086 A | 1/1985 | Duchadeau |
| 4,596,795 A | 6/1986 | Pitha |
| 4,634,699 A | 1/1987 | McDermed et al. |
| 4,683,135 A | 7/1987 | Pecht et al. |
| 4,755,386 A | 7/1988 | Hsiao et al. |
| 4,804,678 A | 2/1989 | Augstein et al. |
| 4,847,286 A | 7/1989 | Tamaki et al. |
| 4,871,865 A | 10/1989 | Lever, Jr. et al. |
| 4,923,892 A | 5/1990 | Lever, Jr. et al. |
| 4,996,296 A | 2/1991 | Pecht et al. |
| 5,049,389 A | 9/1991 | Radhakrishnan |
| 5,116,817 A | 5/1992 | Anik |
| 5,280,784 A | 1/1994 | Kohler |
| 5,281,420 A | 1/1994 | Kelm et al. |
| 5,309,900 A | 5/1994 | Knoch et al. |
| 5,312,046 A | 5/1994 | Knoch et al. |
| 5,336,168 A | 8/1994 | Sibalis |
| 5,340,591 A | 8/1994 | Nakano et al. |
| 5,456,923 A | 10/1995 | Nakamichi et al. |
| 5,458,136 A | 10/1995 | Jaser et al. |
| 5,461,695 A | 10/1995 | Knoch |
| 5,475,023 A | 12/1995 | Baskeyfield et al. |
| 5,485,827 A | 1/1996 | Zapol et al. |
| 5,508,451 A | 4/1996 | Bhattacharya et al. |
| 5,549,102 A | 8/1996 | Lintl et al. |
| 5,552,436 A | 9/1996 | Clemente et al. |
| 5,567,720 A | 10/1996 | Averback |
| 5,576,346 A | 11/1996 | Clemente et al. |
| 5,618,842 A | 4/1997 | Della Valle et al. |
| 5,665,378 A | 9/1997 | Davis et al. |
| 5,700,485 A | 12/1997 | Berde et al. |
| 5,723,269 A | 3/1998 | Akagi et al. |
| 5,739,136 A | 4/1998 | Ellinwood, Jr. et al. |
| 5,740,966 A | 4/1998 | Blaha-Schnabel |
| 5,753,208 A | 5/1998 | Nagy et al. |
| 5,837,280 A | 11/1998 | Kenealy et al. |
| 5,869,090 A | 2/1999 | Rosenbaum |
| 5,952,353 A | 9/1999 | Janicki et al. |
| 5,957,389 A | 9/1999 | Wunderlich et al. |
| 6,000,394 A | 12/1999 | Blaha-Schnabel et al. |
| 6,004,949 A | 12/1999 | Shima et al. |
| 6,083,518 A | 7/2000 | Lindahl |
| 6,085,741 A | 7/2000 | Becker |
| 6,123,924 A | 9/2000 | Mistry et al. |
| 6,138,673 A | 10/2000 | Shepherd |
| 6,176,237 B1 | 1/2001 | Wunderlich et al. |
| 6,207,684 B1 | 3/2001 | Aberg |
| 6,225,327 B1 | 5/2001 | Miller et al. |
| 6,323,219 B1 | 11/2001 | Costanzo |
| 6,365,180 B1 | 4/2002 | Meyer et al. |
| 6,391,452 B1 | 5/2002 | Antonsen et al. |
| 6,433,040 B1 | 8/2002 | Dellamary et al. |
| 6,475,467 B1 | 11/2002 | Keller et al. |
| 6,482,390 B1 | 11/2002 | Hiscocks et al. |
| 6,503,481 B1 | 1/2003 | Thurston et al. |
| 6,513,519 B2 | 2/2003 | Gallem |
| 6,513,727 B1 | 2/2003 | Jaser et al. |
| 6,585,958 B1 | 7/2003 | Keller et al. |
| 6,596,261 B1 | 7/2003 | Adjei et al. |
| 6,596,284 B1 | 7/2003 | Fleming et al. |
| 6,660,715 B2 | 12/2003 | Klibanov |
| 6,923,983 B2 | 8/2005 | Morgan et al. |
| 6,929,801 B2 | 8/2005 | Klose et al. |
| 6,946,144 B1 | 9/2005 | Jordan |
| 7,060,827 B2 | 6/2006 | Singh et al. |
| 7,074,388 B2 | 7/2006 | Adjei et al. |
| 7,109,246 B1 | 9/2006 | Hawtin |
| 7,247,711 B2 | 7/2007 | Benson et al. |
| 7,250,165 B2 | 7/2007 | Heavener et al. |
| 7,258,872 B1 | 8/2007 | Wigmore |
| 7,345,037 B2 | 3/2008 | Garvey et al. |
| 7,427,471 B2 | 9/2008 | Scallon et al. |
| 7,481,995 B2 | 1/2009 | Dickinson et al. |
| 7,550,133 B2 | 6/2009 | Hale et al. |
| 7,566,743 B2 | 7/2009 | Glazman |
| 7,582,297 B2 | 9/2009 | Reed |
| 7,687,054 B2 | 3/2010 | Stefely et al. |
| 7,727,558 B2 | 6/2010 | Milstein et al. |
| 7,744,910 B2 | 6/2010 | Gschneidner et al. |
| 7,758,886 B2 | 7/2010 | Jauernig et al. |
| 7,807,200 B2 | 10/2010 | Lipp et al. |
| 7,867,508 B1 | 1/2011 | Smith |
| 7,897,776 B2 | 3/2011 | Weingarten et al. |
| 7,955,597 B2 | 6/2011 | Giles-Komar et al. |
| 8,006,698 B2 | 8/2011 | Boehm et al. |
| 8,088,935 B2 | 1/2012 | Pearson et al. |
| 8,252,807 B2 | 8/2012 | Logsdon et al. |
| 8,257,744 B2 | 9/2012 | Lopez-Belmonte Encina et al. |
| 8,258,268 B2 | 9/2012 | Wu et al. |
| 8,263,645 B2 | 9/2012 | Keller |
| 8,361,509 B2 | 1/2013 | Lopez-Belmonte Encina et al. |
| 8,383,778 B2 | 2/2013 | Hsieh et al. |
| 8,398,966 B2 | 3/2013 | Wu et al. |
| 8,410,309 B2 | 4/2013 | Leone-Bay et al. |
| 8,430,097 B2 | 4/2013 | Jinks et al. |
| 8,445,437 B2 | 5/2013 | Shi |
| 8,454,938 B2 | 6/2013 | Green et al. |
| 8,461,125 B2 | 6/2013 | Grunstein |
| 8,470,805 B2 | 6/2013 | Chen |
| 8,481,081 B2 | 7/2013 | Babcock et al. |
| 8,513,300 B2 | 8/2013 | Abbas et al. |
| 8,578,933 B2 | 11/2013 | Remmelgas et al. |
| 8,586,044 B2 | 11/2013 | Thumbikat et al. |

(56) References Cited

U.S. PATENT DOCUMENTS

| | | |
|---|---|---|
| 8,586,714 B2 | 11/2013 | Ghayur et al. |
| 8,617,517 B2 | 12/2013 | Elmaleh et al. |
| 8,624,002 B2 | 1/2014 | Gu et al. |
| 8,716,450 B2 | 5/2014 | Ghayur et al. |
| 8,722,855 B2 | 5/2014 | Ghayur et al. |
| 8,785,383 B2 | 7/2014 | Shi |
| 8,808,786 B2 | 8/2014 | Jinks et al. |
| 8,822,645 B2 | 9/2014 | Ghayur et al. |
| 8,853,365 B2 | 10/2014 | Wu et al. |
| 9,011,941 B2 | 4/2015 | Jones et al. |
| 9,029,508 B2 | 5/2015 | Ghayur et al. |
| 9,035,027 B2 | 5/2015 | Ghayur et al. |
| 9,035,085 B2 | 5/2015 | Rath et al. |
| 9,046,513 B2 | 6/2015 | Ghayur et al. |
| 9,095,621 B2 | 8/2015 | Riggs-Sauthier et al. |
| 9,109,026 B2 | 8/2015 | Ghayur et al. |
| 9,181,577 B2 | 11/2015 | Thumbikat et al. |
| 9,198,859 B2 | 12/2015 | Keller et al. |
| 9,226,983 B2 | 1/2016 | Benatuil et al. |
| 9,265,749 B2 | 2/2016 | Gerhart et al. |
| 9,284,279 B2 | 3/2016 | Ford et al. |
| 9,321,836 B2 | 4/2016 | Heavner et al. |
| 9,333,174 B2 | 5/2016 | Batycky et al. |
| 9,353,181 B2 | 5/2016 | Benson et al. |
| 9,439,862 B2 | 9/2016 | Weers et al. |
| 9,447,184 B2 | 9/2016 | Wu et al. |
| 9,492,408 B2 | 11/2016 | Leikauf |
| 9,574,004 B2 | 2/2017 | Ardeleanu et al. |
| 9,592,220 B2 | 3/2017 | Gonda |
| 9,592,293 B2 | 3/2017 | Wu et al. |
| 9,663,587 B2 | 5/2017 | Hsieh et al. |
| 9,670,276 B2 | 6/2017 | Lacy et al. |
| 9,707,206 B2 | 7/2017 | Gerhart et al. |
| 9,744,314 B2 | 8/2017 | Keller et al. |
| 9,855,276 B2 | 1/2018 | Elmaleh |
| 1,039,107 A1 | 8/2019 | Gerhart et al. |
| 1,039,867 A1 | 9/2019 | Gerhart et al. |
| 2002/0009491 A1 | 1/2002 | Rothbard et al. |
| 2004/0013734 A1 | 1/2004 | Babcock et al. |
| 2004/0120956 A1 | 6/2004 | Song et al. |
| 2004/0204399 A1 | 10/2004 | Osbakken et al. |
| 2005/0008638 A1 | 1/2005 | Lu et al. |
| 2005/0033029 A1 | 2/2005 | Lu |
| 2005/0038243 A1 | 2/2005 | Singh et al. |
| 2005/0113317 A1 | 5/2005 | Robinson et al. |
| 2005/0129695 A1 | 6/2005 | Mercken et al. |
| 2005/0191246 A1 | 9/2005 | Bechtold-Peters et al. |
| 2005/0209141 A1 | 9/2005 | Silver et al. |
| 2005/0232923 A1 | 10/2005 | Yan et al. |
| 2005/0244339 A1 | 11/2005 | Jauernig et al. |
| 2005/0266005 A1 | 12/2005 | Heavner et al. |
| 2006/0002995 A1 | 1/2006 | Harwigsson |
| 2006/0069124 A1 | 3/2006 | Rao et al. |
| 2006/0078558 A1 | 4/2006 | Whitsett |
| 2006/0246075 A1 | 11/2006 | Mercken et al. |
| 2007/0036860 A1 | 2/2007 | Wigmore |
| 2007/0086981 A1 | 4/2007 | Meijer et al. |
| 2007/0193577 A1 | 8/2007 | Keller |
| 2007/0219223 A1 | 9/2007 | Wilson et al. |
| 2008/0032918 A1 | 2/2008 | Silver et al. |
| 2008/0078382 A1 | 4/2008 | LeMahieu et al. |
| 2008/0194676 A1 | 8/2008 | Abbas et al. |
| 2008/0214491 A1 | 9/2008 | Logsdon et al. |
| 2008/0227704 A1 | 9/2008 | Kamens |
| 2009/0025713 A1 | 1/2009 | Keller et al. |
| 2009/0081274 A1 | 3/2009 | Silver et al. |
| 2009/0239916 A1 | 9/2009 | Tanaka et al. |
| 2009/0318545 A1 | 12/2009 | Silver et al. |
| 2010/0028351 A1 | 2/2010 | Mercken et al. |
| 2010/0074901 A1 | 3/2010 | Mercken et al. |
| 2010/0087455 A1 | 4/2010 | Gant |
| 2010/0143268 A1 | 6/2010 | Kellaway et al. |
| 2010/0150898 A1 | 6/2010 | Boucher, Jr. |
| 2010/0196286 A1 | 8/2010 | Armer |
| 2010/0233079 A1 | 9/2010 | Jakob et al. |
| 2010/0260668 A1 | 10/2010 | Ghayur et al. |
| 2010/0316576 A1 | 12/2010 | Keller et al. |
| 2011/0044980 A1 | 2/2011 | Ghayur et al. |
| 2011/0112183 A1 | 5/2011 | Riggs-Sauthier et al. |
| 2011/0195924 A1 | 8/2011 | Logsdon et al. |
| 2011/0223216 A1 | 9/2011 | Da Rocha et al. |
| 2011/0250130 A1 | 10/2011 | Benatuil et al. |
| 2012/0076859 A1 | 3/2012 | Hofmann |
| 2012/0118991 A1 | 5/2012 | Keller et al. |
| 2012/0132204 A1 | 5/2012 | Lucking et al. |
| 2012/0201746 A1 | 8/2012 | Liu et al. |
| 2012/0258108 A1 | 10/2012 | Ghayur et al. |
| 2012/0275996 A1 | 11/2012 | Hsieh |
| 2013/0017247 A1 | 1/2013 | Harish et al. |
| 2013/0171059 A1 | 7/2013 | Ghayur et al. |
| 2013/0253475 A1 | 9/2013 | Wang |
| 2014/0007867 A1 | 1/2014 | Bruin et al. |
| 2014/0014094 A1 | 1/2014 | Warner et al. |
| 2014/0065219 A1 | 3/2014 | Bosch et al. |
| 2014/0083422 A1 | 3/2014 | Arvidsson et al. |
| 2014/0109900 A1 | 4/2014 | Jinks |
| 2014/0140927 A1 | 5/2014 | Elmaleh et al. |
| 2014/0242174 A1 | 8/2014 | Walker |
| 2014/0271457 A1 | 9/2014 | Ghayur et al. |
| 2015/0018396 A1 | 1/2015 | Lee et al. |
| 2015/0038530 A1 | 2/2015 | Abraham et al. |
| 2015/0040901 A1 | 2/2015 | Parkes |
| 2015/0057299 A1 | 2/2015 | Ford et al. |
| 2015/0072961 A1 | 3/2015 | Yu et al. |
| 2015/0107589 A1 | 4/2015 | Longest et al. |
| 2015/0224077 A1 | 8/2015 | Gerhart et al. |
| 2015/0224078 A1 | 8/2015 | Gerhart et al. |
| 2015/0273119 A1 | 10/2015 | Heo et al. |
| 2015/0290135 A1 | 10/2015 | Chamarthy et al. |
| 2015/0297557 A1 | 10/2015 | Gerhart et al. |
| 2015/0306107 A1 | 10/2015 | Chen |
| 2015/0320747 A9 | 11/2015 | Schmittmann |
| 2015/0337315 A1 | 11/2015 | Grunstein |
| 2016/0106704 A1 | 4/2016 | Elmaleh et al. |
| 2016/0106802 A1 | 4/2016 | Paterson |
| 2016/0263257 A1 | 9/2016 | Elmaleh et al. |
| 2016/0280791 A1 | 9/2016 | Ghayur et al. |
| 2016/0310681 A1 | 10/2016 | Finke et al. |
| 2016/0319026 A1 | 11/2016 | Ghayur et al. |
| 2016/0346245 A1 | 12/2016 | Gerhart et al. |
| 2016/0346246 A1 | 12/2016 | Gerhart et al. |
| 2016/0347844 A1 | 12/2016 | Dekruyff et al. |
| 2016/0367519 A1 | 12/2016 | Gerhart et al. |
| 2016/0367520 A1 | 12/2016 | Gerhart et al. |
| 2016/0375135 A1 | 12/2016 | Gschneidner et al. |
| 2017/0107574 A1 | 4/2017 | Ziesche |
| 2017/0196904 A1 | 7/2017 | Gotz et al. |
| 2017/0218091 A1 | 8/2017 | Ambrosi |
| 2017/0235918 A1 | 8/2017 | Hagen et al. |
| 2017/0273941 A1 | 9/2017 | Gerhart et al. |
| 2017/0275397 A1 | 9/2017 | Park et al. |
| 2017/0335393 A1 | 11/2017 | Ziesche |
| 2017/0349947 A1 | 12/2017 | Ziesche |

FOREIGN PATENT DOCUMENTS

| | | |
|---|---|---|
| AU | 2015200579 A1 | 2/2015 |
| AU | 2016222339 A1 | 9/2016 |
| EP | 0163683 | 12/1985 |
| EP | 0183457 A2 | 6/1986 |
| EP | 0304802 A2 | 3/1989 |
| EP | 0413583 A3 | 5/1990 |
| EP | 0413583 A2 | 2/1991 |
| EP | 0587264 B1 | 10/1994 |
| EP | 1128826 B1 | 1/2004 |
| EP | 1754492 A1 | 2/2007 |
| EP | 2364696 A1 | 9/2011 |
| EP | 2391618 A2 | 12/2011 |
| EP | 1858485 B1 | 9/2013 |
| EP | 2248517 B1 | 3/2014 |
| EP | 1874270 B1 | 8/2015 |
| EP | 2533777 B1 | 7/2016 |
| GB | 2145107 A | 3/1985 |
| JP | S61143318 A | 7/1986 |

(56) References Cited

FOREIGN PATENT DOCUMENTS

| | | |
|---|---|---|
| JP | H06072869 A | 3/1994 |
| WO | WO-8502541 A1 | 6/1985 |
| WO | WO-9505816 A1 | 3/1995 |
| WO | WO-9631204 A1 | 10/1996 |
| WO | WO-9831346 A1 | 7/1998 |
| WO | WO-9916421 A1 | 4/1999 |
| WO | WO-0027392 A1 | 5/2000 |
| WO | WO-0042993 A2 | 7/2000 |
| WO | WO-0113892 A2 | 3/2001 |
| WO | WO-0212502 A2 | 2/2002 |
| WO | WO-03045331 A2 | 6/2003 |
| WO | WO-2004039826 A1 | 5/2004 |
| WO | WO-2005028511 A2 | 3/2005 |
| WO | WO2005037317 | 4/2005 |
| WO | WO-2005063732 A1 | 7/2005 |
| WO | WO-2005077189 A1 | 8/2005 |
| WO | WO-2005115468 A1 | 12/2005 |
| WO | WO-2006105538 A2 | 10/2006 |
| WO | WO-2007103970 A2 | 9/2007 |
| WO | WO-2008116165 A2 | 9/2008 |
| WO | WO-2009045291 A2 | 4/2009 |
| WO | WO-2009052125 A2 | 4/2009 |
| WO | WO-2009131695 A1 | 10/2009 |
| WO | WO-2010042504 A1 | 4/2010 |
| WO | WO-2010088455 A2 | 8/2010 |
| WO | WO-2010128111 A1 | 11/2010 |
| WO | WO-2012031445 A1 | 3/2012 |
| WO | WO-2012061374 A2 | 5/2012 |
| WO | WO-2014066318 A1 | 5/2014 |
| WO | WO-2014115098 A1 | 7/2014 |
| WO | WO-2015079198 A1 | 6/2015 |
| WO | WO-2015120389 A1 | 8/2015 |
| WO | WO2015120392 | 8/2015 |
| WO | WO-2015161510 A1 | 10/2015 |
| WO | WO-2015185195 A1 | 12/2015 |
| WO | WO-2015185653 A2 | 12/2015 |
| WO | WO-2015185658 A2 | 12/2015 |
| WO | WO-2016004389 A2 | 1/2016 |
| WO | WO-2016011254 A1 | 1/2016 |
| WO | WO-2016064908-1 | 4/2016 |
| WO | WO-2017011729 A1 | 1/2017 |
| WO | WO-2017027387 A1 | 2/2017 |
| WO | WO-2017027402 A1 | 2/2017 |
| WO | WO-2017048860 A1 | 3/2017 |

OTHER PUBLICATIONS

Hammoudeh et al., "Diffuse Alveolar Hemorrhage with ANCA associated vasculitis-review of literature," British Journal of Medical Practitioners (BJMP), 2011, 4(1):a402, 5 pages.
Kim et al., "Nasal and Sinus Inflammation in Chronic Obstructive Pulmonary Disease, COPD," Journal of Chronic Obstructive Pulmonary Disease, 2007, 4:163-166.
Markopoulou et al., "Obliterative bronchiolitis: varying presentations and clinic pathological correlation," Eur. Respir. J., 2002, 19:20-30.
Pratter, "Overview of common causes of chronic cough," Chest, 2006, 129:59S-62S, Supplement.
"View of NCT02412020 on Apr. 7, 2015." *NCT02412020 on 2015_04_07: ClinicalTrials.Gov Archive*, Accessed Jan. 30, 2018 (4 pages). clinicaltrials.gov/archive/NCT02412020/2015_04_07.
"View of NCT02412020 on Apr. 8, 2015." *NCT02412020 on 2015_04_08: ClinicalTrials.Gov Archive*, Accessed Jan. 30, 2018 (4 pages). clinicaltrials.gov/archive/NCT02412020/2015_04_08.
"View of NCT02412020 on Sep. 25, 2015." *NCT02412020 on 2015_09_25: ClinicalTrials.Gov Archive*, Accessed Jan. 30, 2018 (4 pages). clinicaltrials.gov/archive/NCT02412020/2015_09_25.
"View of NCT02412020 on Feb. 19, 2016." *NCT02412020 on 2016_02_19: ClinicalTrials.Gov Archive*, Accessed Jan. 30, 2018 (4 pages). clinicaltrials.gov/archive/NCT02412020/2016_02_19.
"View of NCT02478957 on Jun. 22, 2015." *NCT02478957 on 2015_06_22: ClinicalTrials.Gov Archive*, Accessed Jan. 30, 2018 (4 pages). clinicaltrials.gov/archive/NCT02478957/2015_06_22.

"View of NCT02478957 on Sep. 25, 2015." *NCT02478957 on 2015_09_25: ClinicalTrials.Gov Archive*, Accessed Jan. 30, 2018 (4 pages). clinicaltrials.gov/archive/NCT02478957/2015_09_25.
"View of NCT02478957 on Feb. 26, 2016." *NCT02478957 on 2016_02_26: ClinicalTrials.Gov Archive*, Accessed Jan. 30, 2018 (4 pages). clinicaltrials.gov/archive/NCT02478957/2016_02_26.
"View of NCT02478957 on Sep. 28, 2016." *NCT02478957 on 2016_09_26: ClinicalTrials.Gov Archive*, Accessed Jan. 30, 2018 (4 pages). clinicaltrials.gov/archive/NCT02478957/2016_09_28.
"View of NCT02696499 on Mar. 1, 2016." *NCT02696499 on 2016_03_01: ClinicalTrials.Gov Archive*, Accessed Jan. 30, 2018 (4 pages). clinicaltrials.gov/archive/NCT02696499/2016_03_01.
"View of NCT02696499 on May 3, 2016." *NCT02696499 on 2016_05_03: ClinicalTrials.Gov Archive*, Accessed Jan. 30, 2018 (4 pages). clinicaltrials.gov/archive/NCT02696499/2016_05_03.
"View of NCT02696499 on Apr. 5, 2017." *NCT02696499 on 2017_04_05: ClinicalTrials.Gov Archive*, Accessed Jan. 30, 2018 (4 pages). clinicaltrials.gov/archive/NCT02696499/2017_04_05.
Afrin, B. Lawrence, "Presentation, Diagnosis, and Management of Mast Cell Activation Syndrome," Mast Cells (2013) Chapter 6 (6 pages).
Allistone, A., et al., "The effect of intravenous sodium cromoglycate on the bronchoconstriction induced by sulphur dioxide inhalation in man," Clinical Science, 68:227-232 (1985).
Allowed Claims and Notice of Allowance of U.S. Appl. No. 15/117,711, dated Feb. 13, 2018. (11 pages).
Anderson, et al., "Sodium Cromoglycate Alone and in Combination with Montelukast on the Airway Response to Mannitol in Asthmatic Subjects," J Asthma, 47:429-433 (2010).
Ariyanayagam, M., et al., "Topical sodium cromoglycate in the management of atopic eczema-a controlled trial," British Journal of Dermatology, 112:343-348 (1985).
Ashton, M.J., et al., "The absorption, metabolism and excretion of disodium cromoglycate in nine animal studies," Toxicology and Applied Pharmacology, 26:319-328 (1973).
Asmus, et al., "Pulmonary function response to EDTA, an additive in nebulized bronchodilators," Journal of Allergy and Clinical Immunology, 2001. 107(1): 68-72.
Aswania O.A., et al., "Relative bioavailability of sodium cromoglycate to the lung following inhalation, using urinary excretion," British Journal of Clinical Pharmacology, 47:613-618 (1999).
Aswania O.A., et al., "Relative Lung and Systemic Bioavailability of Sodium Cromoglycate Inhaled Products Using Urinary Drug Excretion Post Inhalation," Biopharm. Drug. Dispos., 23:159-163 (2002).
Aswania O.A., et al., "Relative Lung Bioavailbioty of Generic Sodium Cromoglycate Inhalers Used With and Without a Spacer Device," Pulmonary Pharmacology & Therapeutics, 14:129-133 (2001).
Auty, R.M., et al., "Respiratory tract deposition of sodium cromoglycate is highly dependent upon technique of inhalation using the spinhaler," British Journal Dis. Chest, 81:371-380 (1987).
Balzar, et al., "Mast Cell Phenotype, Location, and Activation in Severe Asthma. Data from the Severe Asthma Research Program," Am J Repir Crit Care Med. 183:299-309, 2010.
Balzar, et al., "Relationships of Small Airway Chymase-Positive Mast Cells and Lung Function in Severe Asthma," Am J Respir Crit Care Med, 171:431-439, (2005).
Barnes, P.J., "New concepts in the pathogenesis of bronchial hyperresponsiveness and asthma," J Allergy Clin Immunol., 83:1013-1026, (1989).
Behr, et al., "Lung Depostition of a Liposomal Cyclosporine a Inhalation Solution in Patients after Lung Transplantation," J Med Pulm Drug Delive., 22(2):121-129, (2009).
Benson, et al., "Uptake of disodium cromoglycate in obstructive airways disease," Clinical Allergy, 3:389-394, (1973).
Bizzintino, et al., "Association between human rhinovirus C and severity of acute asthma in children," Eur Repir J., 37:1037-1042, (2011).
Bourdin, et al., "Upper airway 1:Allergic rhinitis and asthma : united disease through epithelial cells," Thorax, 64:999-1004, (2009).

(56) References Cited

OTHER PUBLICATIONS

Brannan, et al., "Inhibition of mast cell PGD2 release protects against mannitol-induced airway narrowing," Eur Respir J., 27:944-950, (2006).
Burgel, et al., "Update on the roles of distal airways in asthma," Eur Repir Rev., 18:80-95, (2009).
Chen, H.H., Chronic cough. Medscapre Reference. Drugs, Diseases & Procedures. 5 Pages, Updated May 13, 2014.
Cho, A., Recent Advances in Oral Prodrug Disvorey. Annual Reports in Medicinal Chemistry, vol. 41, 395-407, (2006).
Cieslewicz, et al., "The late, but not early, asthmatic response is dependent on IL-5 and correlates with eosinophil inflitration," J. Clin Inv., 104(3):301-308, (1999).
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 11, 2014. Accessed Jan. 30, 2018 (6 pages). [online] Available at: https://www.clinicaltrialsregister.eu/ctr-search/trial/2014-004113-85/DE.
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 22, 2014. Accessed Jan. 30, 2018 (4 pages). [online] Available at: https://www.clinicaltrialsregister.eu/ctr-search/trial/2014-004113-85/ES.
Clinicaltrialsregister.eu. "Randomized, Double-blind, Placebo-controlled, Crossover Design, Efficacy and Safety Study with PA101 in Patients with Indolent Systemic Mastocytosis," Clinical Trials Register. Dec. 4, 2014. Accessed Jan. 30, 2018 (5 pages). [online] Available at: https://www.clinicaltrialsregister.eu/ctr-search/trial/2014-004113-85/NL.
Clinicaltrialsregister.eu. "Treatment of Chronic Cough with PA101," Clinical Trials Register. Dec. 11, 2014. Accessed Jan. 30, 2018 (6 pages). [online] Available at: https://www.clinicaltrialsregister.eu/ctr-search/trial/2014-004025-40/NL.
Clinicaltrialsregister.eu. "Treatment of Chronic Cough with PA101," Clinical Trials Register. Jan. 6, 2015. Accessed Jan. 30, 2018 (6 pages). [online] Available at: https://www.clinicaltrialsregister.eu/ctr-search/trial/2014-004025-40/GB.
Clinicaltrialsregister.eu. "Treatment of Uremic Pruritus with Inhaled PA101B in Patients with End-Stage Renal Disease Requiring Hemodialysis," Clinical Trials Register. Jan. 13, 2016. Accessed Jan. 30, 2018 (6 pages). [online] Available at: https://www.clinicaltrialsregister.eu/ctr-search/trial/2015-004794-33/PL.
Coates, et al., "Rapid Pulmonary Delivery of Inhaled Tobramycin for Pseudomonas Infection in Cystic Fibrosis: A Pilot Project," Pediatr Pulmonol., 43:753-759, (2008).
Cox, et al., "Solid-State Chemistry of Cromolyn Sodium (Disodium Cromoglycate)," J Pharm Sci., 60:1458-1465, (1971).
Curry, et al., "Disposition of Disodium Cromoglycate Administered in Three Particle Sizes," Bristish Journal of Clinical Pharmacology, 2:267-270, (1975).
Deliargyris, Efthymios N., et al., "Mast cell tryptase: a new biomarker in patients with stable coronary artery disease." Atherosclerosis 178.2 (2005): 381-386.
Diaz, et al., "Bronchoalevolar lavage in asthma: The effect of disodium cromoglycate (cromolyn) on leukocyte counts, immunoglobulins, and complement," J Allergy Clin Immunol., 74:41-48, (1984).
Dixon, M., et al., "The Action of sodium cromoglycate on "C" fibre endings in the dog lung," Br. J. Pharm, 70:11-13, (1980).
Doenicke, A., et al., "Osmolalities of propylene Glycol-Contaning Drug Formulations for Parenteral Use. Should Propylene Glycol be used as a Solvent?," Anesth. Analg., 75:431 (5), (1992).
Edwards, A.M., et al., "Oral and inhaled sodium cromoglycate in the management of systemic mastocytosis: a case report," Journal of Medical Case Reports, 4:193-198, (2010).
Edwards, et al., "Sodium cromoglycate in childhood asthma," Thorax, 56:331-332, (2001).

Edwards, et al., "Inhaled sodium cromoglycate in children with asthma," Thorax 57:282, (2002).
Eggleston, P.A., "Exercise-Induces Asthma," Clin Rev Allergy, 1:19-37, (1983).
Emisphere Technologies, Inc., "The facts on . . . Oral Cromolyn Sodium," 2 pages (2006).
Estfan, B. et al., Management of cough in advanced cancer. Journal of Supportive Oncology, 2(6):523-527 (2004).
FDA Guidance for Industry, "Bioavailability and Bioequivalence Studies for Nasal Aerosols and Nasal Sprays for Local Action," Biopharmaceutics, (2003) 37 Pgs.
Finlay, W. H. et al., "Recent advances in predictive understanding respiratory tract deposition."; Journal of Aerosol Medicine, 21:189-205 (2008).
Francis, Heather, and Cynthia J. Meininger. "A review of mast cells and liver disease: What have we learned?." Digestive and Liver Disease 42.8 (2010): 529-536.
Fukasawa, et al., "The Effects of Disodium Cromoglycate on Enhanced Adherence of Haemophilus influenzae to A549 Cells Infected With Respiratory Syncytial Virus," Pediatric Research, (2009), 66(2):168-173.
Furukawa, et al., "A Double-Blind Study Comparing the Effectiveness of Cromolyn Sodium and Sustained-Release Theophylline in Childhood Asthma," Pediatrics, (1984), 74(4):453-459.
Furusho, et al., "The combination of nebulized sodium cromoglycate and salbutamol in the treatment of moderate-to-severe asthma in children," Pediatric Allergy Imminol., (2002), 13:209-216.
Hamid et al., "Inflammation of small airways in asthma," J Allergy Clin Immunol., (1997), 100:44-51.
Hargreaves, M. R. et al., "Inhaled sodium cromoglycate in angiotensin-converting enzyme inhibitor cough," Lancet, 345:13-16 (1995).
Hashimoto et al., "DSCG Reduces RSV-Induced Illness in RSV-Infected Mice," J Med Virol., (2009) 81:354-361.
Hemmati A.A. et al., "The role of sodium cromolyn in treatment of paraquat-induced pulmonary fibrosis in rat", Pharmacological Research, (2002), 46(3):229-234.
Hidari et al., "In Vitro and in Vivo Inhibitory Effects of Disodium Cromoglycate on Influenza Virus Infection," Biol Pharm Bull., (2004), 27(6):825-830.
Hiller et al., "Physical Properties, Hygroscopicity and Estimated Pulmonary Retention of Various Therapeutic Aerosols," Chest, (1980), 77:318-321.
Horan, Richard F., et al., "Cromolyn sodium in the management of systemic mastocytosis." *Journal of Allergy and Clinical Immunology* 85.5 (1990): 852-855.
Hori, Yet al., FDA approved asthma therapeutic agent impacts amyloid B in the brain in a transgenic model of Alzheimer's disease. The Journal of Biological Chemistry, Affinity Sites, Published online on Dec. 2, 2014 as Manuscript M114.586602.
Hoshino et al., "A comparative study of the effects of ketotifen, disodium cromoglycate; and beclomethasone dipropionate on bronchial mucosa and asthma symptoms in patients with atopic asthma," Respir Med., (1998), 92:942-950.
Hoshino et al., "The effect of inhaled sodium cromoglycate on cellular infiltration into the bronchial mucosa and the expression of adhesion molecules in asthmatics," Eur Respir J., (1997), 10:858-865.
Intal FDA Label "Intal® Nebulizer Solution," Aventis Pharmaceuticals, Inc. (2003).
Intal Spincaps, Sodium Cromoglicate 20 mg capsules, Feb. 2007, 4 pages.
Ivax Pharmaceuticals, Cromolyn Sodium—Cromolyn sodium inhalation solution prescribing information, accessed at <https://dailymed.nlm.nih.gov/dailymed/>drugInfo.cfm?setid=8fe37a7a-edd6-4733-bb7e-e01c1906aeba May 2, 2016, (14 pages).
Iyer, V. N. et al., Chronic Cough: An Update. Mayo Clinic Proceedings. 88(10):1115-1126 (2013).
Jones, et al., "Increased Alveolar Epithelial Permeability in Cigarette Smokers," The Lancet, (1980), 1:66-68.
Kano, et al., "Change in osmolarity of disodium cromoglycate solution and protection against exercise-induced bronchospasm in children with asthma," Eur Respir J., (1996), 9:1891-1895.

(56) References Cited

OTHER PUBLICATIONS

Kato, Y. et al. Plasma Concentrations of Disodium Cromoglycate After Various Inhalation Methods in Healthy Subjects. British Journal of Clinical Pharmacology. 48(2) 154-157 (1999).
Keller et al., "Importance of the Inhaler System and Relative Humidity on the Fine Particle Dose (FPD) of Disodium Cromoglycate (DSCG)," RDDD Europe, (2007), 307-310.
Keller, M. "Innovations and perspectives of metered dose inhalers in pulmonary drug delivery," Int J Pharma., (1999), 186:81-90.
Keller, M. et al., Did inappropriate delivery systems hamper therapeutic efficacy of Di-Sodium-Cromo-Glycate (DSCG)? Time for a Reappraisal. Poster Presentation. PARI Pharma: ISAM, P-089, 1 page (2011).
Keller, M. et al., Have inadequate delivery systems hampered the clinical success of inhaled disodium cromoglycate? Time for reconsideration. Expert Opin. Drug Delivery, 8(1):1-17 (2011).
Kippelen et al., "Effect of Sodium Cromoglycate on Mast Cell Mediators during Hyperpnea in Athletes," Med Sci Sports Exerc., (2010) 1853-1860.
Kohler et al., "Lung deposition after inhalation with various nebulisers in preterm infants," Arch Dis Child Fetal Neonatal., (2008), 93(4):F275-F279.
Kohler, et al., "Does Wearing a Noseclip during Inhalation Improve Lung Deposition?" J. Aerosol Med., (2004), 17(2):116-122.
Kohler, et al., "Lung Deposition in Cystic Fibrosis Patients Using an Ultrasonic or a Jet Nebulizer," JAMA, (2003), 16(1):37-46.
Korppi et al., "Disodium Cromoglycate in Asthma—Worth to Be Re-appraised," Allergol Int., (2008), 57:183.
Krawiec et al., "Inhaled Nonsteroidal Anti-inflammatory Medications in the Treatment of Asthma," Respir Care Clin N Am., (1999), 5(4):555-574 (Abstract Only).
Kupper T et al., "Cromoglycate, reproterol, or both—what's best for exercise-induced asthma", Sleep and Breathing; International Journal of the Science and Practice of Sleep Medicine, Springer, (2012)e-pub Dec. 2011, 16(4):1229-1235.
Larsson, et al., "Sodium cromoglycate attenuates pulmonary inflammation without influencing bronchial responsiveness in healthy subjects exposed to organic dust," Clin Exp Allergy, (2001), 31:1356-1368.
Latimer, K. M. et al., Inhibition by sodium cromoglycate of bronchoconstriction stimulated by respiratory heat loss: comparison or pressurized aerosol and powder. Thorax, 39:277-281 (1984).
Laube et al., "The efficacy of slow versus faster inhalation of cromolyn sodium in protecting against allergen challenge in patients with asthma," J. Allergy Clin Immunol., (1998), 101:475-483.
Lavinka, P. C. et al., Molecular signaling and targets from itch: lessons for cough. Cough, 9:8, 13 pages (2013).
Leitch, A.G. et al., "Disodium cromoglycate relieves symptoms in symptomatic young smokers. A double blind placebo controlled trial", Allergy, (1984), 39(3):211-215.
Leone-Bay, A. et al., Oral delivery of sodium cromolyn: Preliminary studies In Vivo and In Vitro.; Pharmaceutical Research, 13(2):222(1995).
Lindstrom, M. et al., A Simple Pharmacokinetic Method to Evaluate the Pulmonary Dose in Clinical Practice—Analyses of Inhaled Sodium Cromoglycate. Respiratory Medice. 98(1): 9-16 (2004).
Luque Carla A. et al., "Treatment of ACE Inhibitor-Induced Cough", Pharmacotherapy: The Journal of Human Pharmacology and Drug Therapy, (1999), 19(7):804-810.
Meltzer, Eric B., and Paul W. Noble., "Idiopathic pulmonary fibrosis." *Orphanet journal of rare diseases* 3.1 (2008): (15 pages).
Miller, T. A. et al., Histone deacetylase inhibitors. Journal of Medicinal Chemistry. 46(24):5097 (2003).
Miyatake, et al., "The New Role of Disodium Cromoglycate in the Treatment of Adults with Bronchial Asthma," Allergol Intl., (2007), 56:231-239.
Moeller, et. al., "Efficacy of high dose inhaled DSCG on asthma control in young children," European Respiratory Society Annual Meeting (ERS), Berlin, Germany, Oct. 4-8, 2008.
Monk, K.R., "Thesis: Consequences of Mast Cell Signaling in Peripheral Nerve," University of Cincinnati, 2006, retrieved Oct. 17, 2017, downloaded from https://etd.ohiolink.edu/rws_etd/document/get/ucin1147889736/inline, (96 pages).
Moon, et al., "Quercetin Inhalation Inhibits the Asthmatic Responses by Exposure to Aerosolized-Ovalbumin in Conscious Guinea-pigs," Arch Pharm Res., (2008), 31(6):771-778.
Moroni, M. et al., "Inhaled sodium cromoglycate to treat cough in advanced lung cancer patients," British Journal of Cancer, 74:309-311 (1996).
Morrison-Smith et al., "Observations on the safety of disodium cromoglycate in long-term use in children," Clinical Allergy, (1972), 2:143-151.
Moss, G. F. et al., Distribution and metabolism of disodium cromoglycate in rats. Toxicology and Applied Pharmacology, 17:691-698 (1970).
Moss, G. F. et al., Plasma levels and urinary excretion of disodium cromoglycate after inhalation by human volunteers. Toicolocy and Applied Pharmacology, 20:147-156 (1971).
NasalCrom FDA Label 2013, (4 pages).
Neale, M. G. et al., The Pharmacokinetics of sodium cromoglycate in man after intravenous and; inhalation administration. British Journal of Clinical Pharm., 22:373-382 (1986).
Nerbrink et al., "Inhalation and Deposition of Nebulized Sodium Cromoglycate in Two Different Particle Size Distributions in Children With Asthma," Pediatr Pulmonol., (2002), 34(5):351-360.
Nogrady. Chapter 4: Pro Drugs and Soft Drugs. In: Medicinal Chemistry: A Biochemical approach. New York: Oxford Universitry Press, p. 388-392 (1985).
Northern General Hospital, Brompton Hospital, "Sodium cromoglycate in chronic asthma," Br. Med. J., (1976), 1:361-364.
Patel, et al., "Dose-response study of sodium cromoglycate in exercise0induces asthma," (1982), 37:663-666.
Patel, et al., "The dose-duration effect of sodium cromoglycate in exercise-induced asthma," Clin Allergy, (1984), 14:87-91.
Patel, K. R. et al., Plasma concentrations of sodium cromoglycate given by nebulisation and metered dose inhalers in patients with exercise-induced asthma: relationship to protective effect. Br. J. Clin. Pharmac., 21:231-233 (1986).
Penttinen, et al., "Disodium cromoglycate can inhibit virus-induced cytopathic effects in vitro," Br Med J., (1977), 1:182.
Picard, M. et al., Expanding spectrum of mast cell activation disorders: Monoclonal and idiopathic mast cell activation syndromes. Clinical Therapeutics, 35(5): 548 (2013).
U.S. Appl. No. 61/405,587, filed Oct. 7, 2016 (12 pages).
U.S. Appl. No. 62/417,887, filed Nov. 4, 2016 (150 pages).
U.S. Appl. No. 62/417,898, filed Nov. 4, 2016 (165 pages).
Reijonen, et al., "Anti-inflammatory Therapy Reduces Wheezing After Bronchiolitis," Arch Pediatr Adolesc Med., (1996), 150:512-517.
Riccardi, V. M., Cutaneous manifestation of neurofibromatosis: cellular interaction, pigmentation, and mast cells, Birth Defects Org Artie Ser, 17: 129-45 (1981) (Abstract only).
Richards, R. et al., Absorption and disposition kinetics of cromolyn sodium and the influence of inhalation technique. Journal of Pharmacology and Experimental Therapeutics, 241(3): 1028-1032 (1987).
Richards, R. et al., Deep inspiration increases the absorption of inhaled sodium cromoglycate. Br. J.; Clin. Pharmac., 27:861-865 (1989).
Richards, R. et al., Effect of methacholine induced bronchoconstriction on the pulmonary distribution and plasma pharmacokinetics of inhaled sodium cromoglycate in subjects with normal and hyperreactive airways. Thorax. 43:611-616 (1988).
Richards, R. et al., Inhalation rate of sodium cromoglycate determines plasma pharmacokinetics and; protection against AMP-induced bronchoconstriction in asthma. Eu.Respir. J., 1:896-901 (1988).
Richards, R. et al., Inhaled histamine increases the rate of absorption of sodium cromoglycate from; the lung. Br. J. Clin. Pharma, 33:337-341 (1992).
Robuschi, M. et al., "Attenuation of aspirin-induced bronchoconstriction by sodium cromoglycate and nedocromil sodium", American Journal of Respiratory and Critical Care Medicine, American Lung Association, New York, NY, (1997), 155(4):1461-1464.
Rooseboom, M. et al., Enzyme-catalyzed activation of anticancer prodrugs. Pharmacological Reviews, 56(1):53-102 (2004).

(56) References Cited

OTHER PUBLICATIONS

Salmon, B. et al., How much aerosol reaches the lungs of wheezy infants and toddlers? Archives of Disease in Childhood, 65:401-403 (1990).
Saulnier, M. G. et al. An efficient method for the synthesis of guanidino prodrugs. Bioorganic &Medicinal Chemistry Letters. 4(16):1985-1990 (1994).
Shenfield, et al., "Absorption of drugs by the Lung," Br. J Clin Pharmac., (1976), 3:583-589.
Silva, PhD Patricia. "Researchers Discover Potential Biomarkers for Identifying IPF Disease Progression." *Pulmonary Fibrosis News*, Oct. 27, 2015, (9 pages), pulmonaryfibrosisnews.com/2015/04/01/researchers-discover-potential-biomarkers-for-identifying-ipf-disease-progression/.
Silverman, M., "Inhaled sodium cromoglycate," Thorax, (2001), 56:585-586.
Silverman, R. B. et al. Chapter 8: Prodrugs and drug delivery systems. In: The Organic Chemistry of Drug Design and Drug Action. San Diego: Academic Press, Inc. p. 352-401 (1992).
Soferman, et al., "Comparison between bronchial response to inhaled hypoosmolar and isoosmolar solutions of sodium cromoglycate after exercise challenge," Annals of Allergy, (1990), 64:143-146.
Spooner, et al., "Mast-cell stabilising agents to prevent exercise-induced bronchoconstriction," Copyright © 2009 The Cochrane Collaboration, Article first published online: Oct. 20, 2003, pp. 1-40.
Stevens, et al., "Sodium cromoglicate: an ineffective drug or meta-analysis misused?" Pharm Stat., (2007), 6:123-137.
Storms, et al., "Cromolyn Sodium: Fitting an Old Friend into Current Asthma Treatment," J Asthma, (2005), 42:79-89.
Tang, et al., "Aerosol Growth Studies III.," J Aerosol Sci., (1977), 8:321-330.
Tasche, M.J.A, et al., "Inhaled disodium cromoglycate (DSCG) as maintenance therapy in children with asthma: a systematic review." Thorax 55.11 (2000): 913-920.
Taylor, et al., "Estimation of equivalent pore radii of pulmonary capillary and alveolar membranes," Am J Physiocol., (1970), 218:1133-1140.
Taylor, K. M. G. et al., The Influence of Liposomal encapsulation on sodium cromoglycate pharmacokinetics in man. Pharmaceutical Research, 6(7):633-636 (1989).
Tulic, et al., "Contribution of the Distal Lung to the Pathologic and Physiologic Changes in Asthma," Chest, (2003), 123:348S-355S.
Tullett et al., "Dose-response effect of sodium cromoglycate pressurised aerosol in exercise induced asthma," Thorax, (1985), 40:41-44.
U.S. Appl. No. 15/750,811, filed Feb. 6, 2018 (155 pages).
U.S. Appl. No. 15/887,825, filed Feb. 2, 2018 (155 pages).
U.S. Office Action for U.S. Appl. No. 14/617,130 dated Jan. 11, 2017 (24 pages).
U.S. Office Action for U.S. Appl. No. 14/617,130 dated May 9, 2016 (22 pages).
U.S. Office Action for U.S. Appl. No. 14/617,221 dated Oct. 25, 2017 (41 pages).
U.S. Office Action for U.S. Appl. No. 14/617,221 dated Aug. 26, 2015 (36 pages).
U.S. Office Action for U.S. Appl. No. 14/617,221 dated Jun. 16, 2016 (33 pages).
U.S. Office Action for U.S. Appl. No. 14/686,535 dated Jan. 5, 2016 (13 pages).
U.S. Office Action for U.S. Appl. No. 14/686,535 dated Jun. 25, 2015 (22 pages).
U.S. Office Action for U.S. Appl. No. 15/232,731 dated Mar. 23, 2017 (22 pages).
U.S. Office Action for U.S. Appl. No. 15/232,731 dated Mar. 29, 2017 (8 pages).
U.S. Office Action for U.S. Appl. No. 15/232,731 dated Nov. 15, 2016 (19 pages).
U.S. Office Action for U.S. Appl. No. 15/232,747 dated Dec. 2, 2016 (16 pages).
Urbano, et al., "Review of the NAEPP 2007 Expert Panel Report (EPR-3) on Asthma Diagnosis and Treatment Guidelines," JMCP, (2008), 14(1):41-49.
US Office Action for U.S. Appl. No. 15/117,711, dated Apr. 6, 2017 (12 pages).
US Office Action for U.S. Appl. No. 15/117,711 dated Oct. 3, 2017 (11 pages).
US Office Action for U.S. Appl. No. 15/232,747 dated Jun. 21, 2017 (22 pages).
Van De Wouden et al., "Sodium Cromoglycate for Asthma in Children(Review)," Cochran Database Syst Rev., (2003), 1-48.
Van De Wouden, et al., "Inhaled sodium cromoglycate for asthma in children (Review)," Cochrane Library, (2011), 3:1-69.
Vessal, G. et al., Effect of oral cromolyn sodium on CKD-associated pruritus and serum tryptase level: a double-blind placebo-controlled study. Nephrol Dial Transplant. 25:1541-1547 (2010).
Walker, S. R. et al., The Fate of [14C]disodium Cromoglycate in Man, J. Pharm. Pharmacol., 24:525-531 (1972).
Weiner et al., "Isotonic Nebulized Disodium Cromoglycate Provides Better Protection against Methacholine- and Exercise-induced Bronchoconstriction," Am Rev Respir Dis., (1988), 137:1309-1311.
Yahav, Y. et al., Sodium cromoglycate in asthma: correlation between response and serum; concentrations. Archives of Disease in Childhood. 63:592-597 (1988).
Yamazaki, et al., "The Inhibitory Effect of Disodium Cromoglycate on the Growth of Chlamydophila (Chlamydia) pneumoniae in Vitro," Biol Pharm Bull., (2006), 29(4):799-800.
Yoshimi, A. et al., Characteristics of 1,3-Bis-(2-ethoxycarbonylchromon-5-yloxy)-2-((S)-lysyloxy)propane Dihydrochloride (N-556), a Prodrug for the oral delivery of disodium cromoglycate, in; absorption and excretion in rats and rabbits. J.Pharmacobio-Dyn., 15:681-686 (1992).
Yoshimi, A. et al., Importance of hydrolysis of amino acid moiety in water-soluble prodrugs of disodium cromoglycate for increased orral bioavailability. J.Pharmacobio-Dyn., 15:339-345 (1992).
Zakynthinos, Epaminondas, and Nikolitsa Pappa. "Inflammatory biomarkers in coronary artery disease." Journal of cardiology 53.3 (2009): 317-333.
Zamora, et al., "Neurofibromatosis-associated lung disease: a case series and literature review," European Respiratory Journal, 2007, 29: 210-214.
PCT/US2015/015029 International Search Report and Written Opinion published Aug. 13, 2015 (18 pages).
PCT/US2015/015033 International Search Report and Written Opinion published Aug. 13, 2015 (15 pages).
PCT/US2016/042437 International Search Report and Written Opinion published Jan. 19, 2017 (17 pages).
PCT/US2016/045804 International Search Report and Written Opinion published Feb. 16, 2017 (8 pages).
PCT/US2016/045849 International Search Report and Written Opinion published Feb. 16, 2017 (8 pages).
Rsc.org. (2018). *Cromolyn | The Merck Index Online*. [online] Available at: https://www.rsc.org/Merck-Index/monograph/print/m3851/cromolyn?q=unauthorize [Accessed Feb. 15, 2018].
Rsc.org. (2018). *Nifedipine | The Merck Index Online*. [online] Available at: https://www.rsc.org/Merck-Index/monograph/print/m7883/nifedipine?q=unauthorize [Accessed Feb. 15, 2018].
Advisory Action for U.S. Appl. No. 14/617,221, dated Aug. 19, 2016.
Aswania et al., "Relative lung and bioavailability of generic sodium cromoglycate inhalers used without a spacer device," Pulmonary Pharmacology & Therapeutics, 14:129-133 (2001).
Final Rejection for U.S. Appl. No. 14/617,221, dated Jun. 16, 2016.
Kitabis Pak reference (www.rxlist.com/kitabis-pak-drug.htm, 2 pages, 2011.
Mazzone, "Old drug, new tricks: reducing cough in IPF," Lancet Respir Med, 2017, pp. 1-2.
U.S. Appl. No. 14/317,130, Restriction Requirement dated Aug. 5, 2015, (701.201).
U.S. Appl. No. 14/617,221 Office Action dated Aug. 26, 2015.

CROMOLYN COMPOSITIONS FOR TREATMENT OF PULMONARY FIBROSIS

CROSS-REFERENCE TO RELATED APPLICATIONS

This application is a continuation application of PCT Application No. PCT/US17/053327, filed Sep. 25, 2017; which claims the priority benefit of U.S. provisional application Nos. 62/405,587 filed on Oct. 7, 2016 and 62/417,887 filed on Nov. 4, 2016; each of which is incorporated by reference herein in its entirety.

FIELD OF THE DISCLOSURE

The disclosure is directed to the field of medicine and, in, particular the use of compositions comprising cromolyn for the treatment pulmonary fibrosis, including idiopathic pulmonary fibrosis.

BACKGROUND

Pulmonary fibrosis, including idiopathic pulmonary fibrosis (IPF), represents a chronic and progressive disease with high mortality and limited therapeutic options. Pulmonary fibrosis is a chronic lung disease characterized pathologically by excessive accumulation of extracellular matrix (ECM) and remodeling of the lung architecture, and additionally characterized by recognizable clinical, physiologic, and radiographic findings. The pathologic findings in pulmonary fibrosis (excessive accumulation of ECM and remodeling of the lung architecture) are a consequence of disturbances in two physiologically balanced processes: proliferation and apoptosis of fibroblasts, and accumulation and breakdown of ECM. When the normal balance between ECM deposition and turnover is shifted toward deposition or away from breakdown, excessive ECM accumulates. When the balance between fibroblast proliferation and apoptosis is shifted toward accelerated proliferation or slowed apoptosis, fibroblasts accumulate.

IPF is characterized by a poor prognosis, with an estimated 5-year survival of approximately 20%. Subjects suffering from IPF experience progressive and irreversible lung functional impairment that leads to chronic respiratory insufficiency with a severely impaired quality of life. Therefore, there is a continuing need to develop new therapeutic approaches to the treatment of subjects having pulmonary fibrosis, including IPF.

SUMMARY

The disclosure provides compositions and methods for the treatment of pulmonary fibrosis, including IPF.

Specifically, the disclosure provides a method of treating pulmonary fibrosis in a subject comprising administering to the subject a pharmaceutical composition comprising from about 1% by weight to about 10% by weight of cromolyn sodium and an ionic osmotic agent with an inhalation device. In certain embodiments, the pharmaceutical composition comprises about 1%, about 2%, about 3%, about 4%, about 5%, about 6%, about 7%, about 8%, about 9%, or about 10% by weight of cromolyn sodium. In certain embodiments, the pharmaceutical composition comprises about 2% by weight of cromolyn sodium. In certain embodiments, the pharmaceutical composition comprises about 4% by weight of cromolyn sodium. In certain embodiments, the pharmaceutical composition comprises about 6% by weight of cromolyn sodium. In certain embodiments, the inhalation device is a nebulizer. In certain embodiments, the inhaler is a high-efficiency nebulizer.

The disclosure provides a pharmaceutically acceptable aerosol for the treatment of pulmonary fibrosis in a subject, comprising droplets of an aqueous solution comprising (i) from about 2% to about 6% by weight of cromolyn sodium and (ii) an osmolarity adjusting agent comprising (a) between about 0.1% and about 0.5% by weight of sodium chloride, inclusive of the endpoints, and (b) optionally salts of ethylenediaminetetraacetic acid (EDTA), wherein said aerosol has a respirable fraction (≤3.3 μm) as measured by USP <1601> of at least about 30%, and wherein said treatment of said pulmonary fibrosis in said subject is achieved via delivery of a therapeutically effective amount of cromolyn sodium to the lungs of the subject by said subject orally inhaling said pharmaceutically acceptable aerosol. In certain embodiments, the aerosol has a respirable fraction (≤3.3 μm) as measured by USP <1601> or USP <601> of at least about 30%. In certain embodiments, the aerosol has a respirable fraction (≤3.3 μm) as measured by USP <1601> or USP <601> of at least about 30% and a respirable fraction (≤5 μm) as measured by USP <1601> or USP <601> of at least about 75%.

The disclosure provides a pharmaceutically acceptable aerosol for the treatment of pulmonary fibrosis in a subject, consisting of droplets of an aqueous solution consisting of (i) from about 2% to about 6% by weight of cromolyn sodium and (ii) an osmolarity adjusting agent consisting of (a) between about 0.1% and about 0.5% by weight of sodium chloride, inclusive of the endpoints, and (b) optionally salts of ethylenediaminetetraacetic acid (EDTA), wherein said aerosol has a respirable fraction (≤3.3 μm) as measured by USP <1601> of at least about 30%, and wherein said treatment of said pulmonary fibrosis in said subject is achieved via delivery of a therapeutically effective amount of cromolyn sodium to the lungs of the subject by said subject orally inhaling said pharmaceutically acceptable aerosol. In certain embodiments, the aerosol has a respirable fraction (≤3.3 μm) as measured by USP <1601> or USP <601> of at least about 30%. In certain embodiments, the aerosol has a respirable fraction (≤3.3 μm) as measured by USP <1601> or USP <601> of at least about 30% and a respirable fraction (≤5 μm) as measured by USP <1601> or USP <601> of at least about 75%.

The disclosure provides a dosage form for the treatment of pulmonary fibrosis in a subject comprising: (a) an aqueous pharmaceutical composition comprising (i) from about 2% to about 6% by weight of cromolyn sodium, and (ii) an osmolarity adjusting agent consisting of (A) between about 0.1% to about 0.5% sodium chloride, inclusive of the endpoints; and (B) optionally salts of EDTA; and (b) an inhalation device that forms an aerosol of said pharmaceutical composition, said aerosol exhibiting a respirable fraction of said pharmaceutical composition (≤5 μm) as measured by USP <1601> of at least about 60%. In certain embodiments, the pharmaceutical composition further comprises purified water and sodium EDTA. In certain embodiments, the pharmaceutical composition comprises from about 5 mg to about 80 mg of cromolyn sodium. In certain embodiments, the pharmaceutical composition comprises from about 36 mg to about 44 mg of cromolyn sodium. In certain embodiments, the aerosol has a respirable fraction (≤3.3 μm) as measured by USP <1601> of at least about 30%. In certain embodiments, the aerosol has a respirable fraction (≤3.3 μm) as measured by USP <1601> of at least about 30% and a respirable fraction (≤5 μm) as measured by USP <1601> of at least about 75%. In certain embodiments, wherein the osmolarity adjusting agent consists of between 0.1% to 0.2% sodium chloride, inclusive of the endpoints.

The disclosure provides a method of treating pulmonary fibrosis in a subject comprising administering to the subject a pharmaceutical composition comprising from about 1% by weight to about 99% by weight of cromolyn sodium with an inhalation device. In certain embodiments, the pharmaceutical composition comprises about 1%, about 2%, about 3%, about 4%, about 5%, about 6%, about 7%, about 8%, about 9%, about 10%, about 20%, about 30%, about 40%, about 50%, about 60%, about 70%, about 80%, about 90%, or about 99% by weight of cromolyn sodium. In certain embodiments, the inhalation device is a dry-powder inhaler.

The disclosure provides a method of treating a subject having pulmonary fibrosis, comprising administering to the subject a pharmaceutical composition comprising from about 2% by weight to about 99% by weight of cromolyn sodium with an inhalation device, wherein in the three-month period prior to said administration the subject was known to have increased serum concentrations of one or more of BGM, C1M, C3A, C3M, C5M, C6M, VICM, CRPM, FPA, and D-dimer. In certain embodiments, in the three-month period prior to the administration the subject was determined to have increased serum concentrations of BGM. In certain embodiments, in the three-month period prior to the administration the subject was determined to have increased serum concentrations of C1M. In certain embodiments, in the three-month period prior to the administration the subject was determined to have increased serum concentrations of C3A. In certain embodiments, in the three-month period prior to the administration the subject was determined to have increased serum concentrations of C3M. In certain embodiments, in the three-month period prior to the administration the subject was determined to have increased serum concentrations of C5M. In certain embodiments, in the three-month period prior to the administration the subject was determined to have increased serum concentrations of C6M. In certain embodiments, in the three-month period prior to the administration the subject was determined to have increased serum concentrations of VICM. In certain embodiments, in the three-month period prior to the administration the subject was determined to have increased serum concentrations of CRPM. In certain embodiments, in the three-month period prior to the administration the subject was determined to have increased serum concentrations of FPA. In certain embodiments, in the three-month period prior to the administration the subject was determined to have increased serum concentrations of D-dimer. In certain embodiments, the pharmaceutical composition comprises from about 2% by weight to about 6% by weight of cromolyn sodium and an ionic osmotic agent, and the inhalation device is a nebulizer. In certain embodiments, the nebulizer is a high-efficiency nebulizer. In certain embodiments, the pharmaceutical composition comprises from about 2% by weight to about 99% by weight of cromolyn sodium and the inhalation device is a dry-powder inhaler.

The disclosure provides a method of treating a subject having pulmonary fibrosis, wherein in the three-month period prior to said treatment the subject was known to have increased serum concentrations of one or more of BGM, C1M, C3A, C3M, C5M, C6M, VICM, CRPM, FPA, and D-dimer, the method comprising administering to the subject a pharmaceutical composition comprising from about 2% by weight to about 99% by weight of cromolyn sodium with an inhalation device. In certain embodiments, in the three-month period prior to the administration the subject was determined to have increased serum concentrations of BGM. In certain embodiments, in the three-month period prior to the administration the subject was determined to have increased serum concentrations of C1M. In certain embodiments, in the three-month period prior to the administration the subject was determined to have increased serum concentrations of C3A. In certain embodiments, in the three-month period prior to the administration the subject was determined to have increased serum concentrations of C3M. In certain embodiments, in the three-month period prior to the administration the subject was determined to have increased serum concentrations of C5M. In certain embodiments, in the three-month period prior to the administration the subject was determined to have increased serum concentrations of C6M. In certain embodiments, in the three-month period prior to the administration the subject was determined to have increased serum concentrations of VICM. In certain embodiments, in the three-month period prior to the administration the subject was determined to have increased serum concentrations of CRPM. In certain embodiments, in the three-month period prior to the administration the subject was determined to have increased serum concentrations of FPA. In certain embodiments, in the three-month period prior to the administration the subject was determined to have increased serum concentrations of D-dimer. In certain embodiments, the pharmaceutical composition comprises from about 2% by weight to about 6% by weight of cromolyn sodium and an ionic osmotic agent and the inhalation device is a nebulizer. In certain embodiments, the nebulizer is a high-efficiency nebulizer. In certain embodiments, the pharmaceutical composition comprises from about 2% by weight to about 99% by weight of cromolyn sodium and the inhalation device is a dry-powder inhaler.

The disclosure provides a method of treating a subject having pulmonary fibrosis, comprising: (a) determining whether in the 3-month period prior to said treatment, the subject has increased serum concentrations of one or more of BGM, C1M, C3A, C3M, C5M, C6M, VICM, CRPM, FPA, and D-dimer; and (b) if the subject is determined to have increased serum concentrations of one or more of BGM, C1M, C3A, C3M, C5M, C6M, VICM, CRPM, FPA, and D-dimer, a pharmaceutical composition comprising from about 2% by weight to about 99% by weight of cromolyn sodium is administered to the subject with an inhalation device. In certain embodiments, in the three-month period prior to the administration the subject was determined to have increased serum concentrations of BGM. In certain embodiments, in the three-month period prior to the administration the subject was determined to have increased serum concentrations of C1M. In certain embodiments, in the three-month period prior to the administration the subject was determined to have increased serum concentrations of C3A. In certain embodiments, in the three-month period prior to the administration the subject was determined to have increased serum concentrations of C3M. In certain embodiments, in the three-month period prior to the administration the subject was determined to have increased serum concentrations of C5M. In certain embodiments, in the three-month period prior to the administration the subject was determined to have increased serum concentrations of C6M. In certain embodiments, in the three-month period prior to the administration the subject was determined to have increased serum concentrations of VICM. In certain embodiments, in the three-month period prior to the administration the subject was determined to have increased serum concentrations of CRPM. In certain embodiments, in the three-month period prior to the administration the subject was determined to have increased serum concentrations of FPA. In certain embodiments, in the three-month period prior to the administration the subject was determined to have increased serum concentrations of D-dimer. In certain embodiments, the pharmaceutical composition comprises from about 2% by weight to about 6% by weight of cromolyn sodium and an ionic osmotic agent and the inhalation device is a nebulizer. In certain embodiments, the nebulizer is a high-efficiency nebulizer. In certain embodiments, the pharmaceutical composition comprises from about 2% by weight to about 99% by weight of cromolyn sodium and the inhalation device is a dry-powder inhaler.

The disclosure provides a method of treating a subject having pulmonary fibrosis, comprising (a) determining whether in the 3-month period prior to said treatment, the subject has increased serum concentrations of one or more of BGM, C1M, C3A, C3M, C5M, C6M, VICM, CRPM, FPA, and D-dimer; and (b) administering to the subject a pharmaceutical composition comprising from about 2% by weight to about 99% by weight of cromolyn sodium with an inhalation device if the subject is determined to have increased serum concentrations of one or more of BGM, C1M, C3A, C3M, C5M, C6M, VICM, CRPM, FPA, and D-dimer. In certain embodiments, in the three-month period prior to the administration the subject was determined to have increased serum concentrations of BGM. In certain embodiments, in the three-month period prior to the administration the subject was determined to have increased serum concentrations of C1M. In certain embodiments, in the three-month period prior to the administration the subject was determined to have increased serum concentrations of C3A. In certain embodiments, in the three-month period prior to the administration the subject was determined to have increased serum concentrations of C3M. In certain embodiments, in the three-month period prior to the administration the subject was determined to have increased serum concentrations of C5M. In certain embodiments, in the three-month period prior to the administration the subject was determined to have increased serum concentrations of C6M. In certain embodiments, in the three-month period prior to the administration the subject was determined to have increased serum concentrations of VICM. In certain embodiments, in the three-month period prior to the administration the subject was determined to have increased serum concentrations of CRPM. In certain embodiments, in the three-month period prior to the administration the subject was determined to have increased serum concentrations of FPA. In certain embodiments, in the three-month period prior to the administration the subject was determined to have increased serum concentrations of D-dimer. In certain embodiments, the pharmaceutical composition comprises from about 2% by weight to about 6% by weight of cromolyn sodium and an ionic osmotic agent and the inhalation device is a nebulizer. In certain embodiments, the inhaler is a high-efficiency nebulizer. In certain embodiments, the pharmaceutical composition comprises from about 2% by weight to about 99% by weight of cromolyn sodium and the inhalation device is a dry-powder inhaler.

The disclosure provides any of the methods described herein, wherein the subject experiences a decline of forced vital capacity (% FVC) of less than about 10%, or less than about 9%, or less than about 8%, or less than about 7%, or less than about 6%, or less than about 5%, or less than about 4%, or less than about 3%, or less than about 2%, or less than about 1%, or no decline following administration of the pharmaceutical compositions disclosed herein to the subject for at least 2 weeks, or for at least 4 weeks, or for at least 8 weeks, or for at least 12 weeks, or for at least 16 weeks, or for at least 20 weeks, or for at least 24 weeks, or for at least 48 weeks, or for at least 52 weeks. In certain embodiments, the subject experiences a decline of forced vital capacity (% FVC) of less than 10%. In certain embodiments, the subject experiences a decline of forced vital capacity (% FVC) of less than 9%. In certain embodiments, the subject experiences a decline of forced vital capacity (% FVC) of less than 8%. In certain embodiments, the subject experiences a decline of forced vital capacity (% FVC) of less than 7%. In certain embodiments, the subject experiences a decline of forced vital capacity (% FVC) of less than 6%. In certain embodiments, the subject experiences a decline of forced vital capacity (% FVC) of less than 5%. In certain embodiments, the subject experiences a decline of forced vital capacity (% FVC) of less than 4%. In certain embodiments, the subject experiences a decline of forced vital capacity (% FVC) of less than 3%. In certain embodiments, the subject experiences a decline of forced vital capacity (% FVC) of less than 2%. In certain embodiments, the subject experiences a decline of forced vital capacity (% FVC) of less than 1%. In certain embodiments, the subject experiences no decline in forced vital capacity (% FVC).

The disclosure provides any of the methods described herein, wherein the subject experiences a decline of forced vital capacity (FVC) of less than about 300 mL, or less than about 250 mL, or less than about 200 mL, or less than about 150 mL, or less than about 100 mL or less than about 50 mL, or less than about 25 mL, or no decline following administration of the pharmaceutical compositions disclosed herein to the subject for at least 2 weeks, or for at least 4 weeks, or for at least 8 weeks, or for at least 12 weeks, or for at least 16 weeks, or for at least 20 weeks, or for at least 24 weeks, or for at least 48 weeks, or for at least 52 weeks. The disclosure provides any of the methods described herein, wherein the subject experiences a decline of forced vital capacity (FVC) of less than about 300 mL following administration of the pharmaceutical composition to the subject for at least 24 weeks. In certain embodiments, the subject experiences a decline of forced vital capacity (FVC) of less than about 275 mL. In certain embodiments, the subject experiences a decline of forced vital capacity (FVC) of less than about 250 mL. In certain embodiments, the subject experiences a decline of forced vital capacity (FVC) of less than about 200 mL. In certain embodiments, the subject experiences a decline of forced vital capacity (FVC) of less than about 175 mL. In certain embodiments, the subject experiences a decline of forced vital capacity (FVC) of less than about 150 mL. In certain embodiments, the subject experiences a decline of forced vital capacity (FVC) of less than about 125 mL. In certain embodiments, the subject experiences a decline of forced vital capacity (FVC) of less than about 100 mL. In certain embodiments, the subject experiences a decline of forced vital capacity (FVC) of less than about 75 mL. In certain embodiments, the subject experiences a decline of forced vital capacity (FVC) of less than about 50 mL. In certain embodiments, the subject experiences a decline of forced vital capacity (FVC) of less than about 25 mL. In certain embodiments, the subject experiences no decline of forced vital capacity (FVC).

The disclosure provides any of the methods disclosed herein, wherein the inhalation device is a nebulizer or a dry-powder inhaler. In certain embodiments, the inhalation device is a nebulizer. In certain embodiments, the inhalation device is a high-efficiency nebulizer. In certain embodiments, the inhalation device is a dry-powder inhaler.

The disclosure provides use of a composition comprising from about 2% by weight to about 6% by weight of cromolyn sodium in the manufacture of a medicament for the treatment of a subject having pulmonary fibrosis. In certain embodiments, the composition comprising from about 2% by weight to about 6% by weight of cromolyn sodium is used with a nebulizer, such as a high-efficiency nebulizer.

The disclosure provides use of a composition comprising from about 2% by weight to about 99% by weight of cromolyn sodium in the manufacture of a medicament for the treatment of a subject having pulmonary fibrosis. In certain embodiments, the composition comprising from about 2% by weight to about 99% by weight of cromolyn sodium is used with a dry-powder inhaler.

The disclosure provides a kit for the treatment of a subject having pulmonary fibrosis, comprising (a) a pharmaceutical composition comprising from about 2% by weight to about 99% by weight of cromolyn sodium, and (b) an inhalation device for the administration of the pharmaceutical composition to the subject. In certain embodiments, the pharmaceutical composition comprises from about 2% by weight to about 6% by weight of cromolyn sodium and an ionic osmotic agent and the inhalation device is a nebulizer. In certain embodiments, the inhaler is a high-efficiency nebulizer. In certain embodiments, the pharmaceutical composition comprises from about 2% by weight to about 99% by weight of cromolyn sodium and the inhalation device is a dry-powder inhaler.

The disclosure provides any of the methods described herein, wherein the pharmaceutical composition comprising from about 2% by weight to about 99% by weight of cromolyn sodium is administered to the subject in combination with one or more other agents. In some embodiments, the one or more other agents is selected from an inhibitor of alpha-PDGFR, beta-PDGFR, FGFR, VEGFR and FLT3. In some embodiments, the one or more other agents is selected from an inhibitor of alpha-PDGFR. In some embodiments, the one or more other agents is selected from an inhibitor of beta-PDGFR. In some embodiments, the one or more other agents is selected from an inhibitor of FGFR. In some embodiments, the one or more other agents is selected from an inhibitor of VEGFR. In some embodiments, the one or more other agents is selected from an inhibitor of FLT3. In some embodiments, the one or more other agents is nintedanib. In some embodiments, the pharmaceutical composition comprising from about 2% by weight to about 99% by weight of cromolyn sodium is administered to the subject from one to five times per day, and the one or more other agents is administered to the subject from one to three times per day. In some embodiments, the pharmaceutical composition comprising from about 2% by weight to about 99% by weight of cromolyn sodium is administered to the subject from one to five times per day, and nintedanib is administered to the subject from one to three times per day. In some embodiments, nintedanib is administered to the subject two times per day. In some embodiments, the total dose of said nintedanib in each dosing period comprises from about 100 mg to about 150 mg of said nintedanib. In some embodiments are provided any of the methods described herein wherein the one or more other agents is pirfenidone. In some embodiments, the pirfenidone is administered to the subject from one to five times per day. In some embodiments, the pirfenidone is administered to the subject three times per day. In some embodiments, the total dose of said pirfenidone in each dosing period comprises about 801 mg of pirfenidone. In some embodiments, the total dose of said pirfenidone administered to the subject on daily basis is 2403 mg. In certain embodiments, the pharmaceutical composition comprises from about 2% by weight to about 6% by weight of cromolyn sodium and an ionic osmotic agent and the inhalation device is a nebulizer. In certain embodiments, the inhaler is a high-efficiency nebulizer. In certain embodiments, the pharmaceutical composition comprises from about 2% by weight to about 99% by weight of cromolyn sodium and the inhalation device is a dry-powder inhaler.

The disclosure provides any of the methods disclosed herein, wherein administration of the pharmaceutical composition with the inhalation device produces in the subject an AUC(0-∞) of the cromolyn sodium greater than about 200 ng*hr/mL, and a Cmax of the cromolyn sodium greater than about 80 ng/mL. In certain embodiments, administration of the pharmaceutical composition with the inhalation device produces in the subject an AUC(0-∞) of the cromolyn sodium greater than about 330 ng*hr/mL, and a Cmax of the cromolyn sodium greater than about 150 ng/mL. In certain embodiments, administration of the pharmaceutical composition with the inhalation device produces in the subject an AUC(0-∞) of the cromolyn sodium greater than about 100 ng*hr/mL, and a Cmax of the cromolyn sodium greater than about 40 ng/mL. In certain embodiments, administration of the pharmaceutical composition comprising about 40 mg of cromolyn sodium with the inhalation device produces in the subject an AUC(0-∞) of the cromolyn sodium that is between about 120 ng*hr/mL and about 500 ng*hr/mL. In certain embodiments, administration of the pharmaceutical composition comprising about 40 mg of cromolyn sodium with the inhalation device produces in the subject an AUC (0-∞) of the cromolyn sodium that is within 80% to 125% of about 340 ng*hr/mL. In certain embodiments, administration of the pharmaceutical composition comprising about 40 mg of cromolyn sodium with the inhalation device produces in the subject an AUC(0-6) of the cromolyn sodium that is between about 120 ng*hr/mL and about 350 ng*hr/mL. In certain embodiments, administration of the pharmaceutical composition comprising about 40 mg of cromolyn sodium with the inhalation device produces in the subject an AUC(0-6) of the cromolyn sodium that is within 80% to 125% of about 237 ng*hr/mL. In certain embodiments, administration of the pharmaceutical composition comprising about 40 mg of cromolyn sodium with the inhalation device produces in the subject a Cmax of the cromolyn sodium of between about 40 ng/mL and about 150 ng/mL. In certain embodiments, administration of the pharmaceutical composition comprising about 40 mg of cromolyn sodium with the inhalation device produces in the subject a Cmax of the cromolyn sodium that is within 80% to 125% of about 75 ng/mL, or about 82 ng/mL, or about 85 ng/mL, or about 93 ng/mL. In certain embodiments, administration of the pharmaceutical composition comprising about 60 mg of cromolyn sodium with the inhalation device produces in the subject an AUC(0-∞) of the cromolyn sodium that is between about 250 ng*hr/mL and about 1000 ng*hr/mL. In certain embodiments, administration of the pharmaceutical composition comprising about 60 mg of cromolyn sodium with the inhalation device produces in the subject an AUC(0-∞) of the cromolyn sodium that is within 80% to 125% of about 542 ng*hr/mL. In certain embodiments, administration of the pharmaceutical composition comprising about 60 mg of cromolyn sodium with the inhalation device produces in the subject an AUC(0-6) of the cromolyn sodium that is between about 200 ng*hr/mL and about 700 ng*hr/mL. In certain embodiments, administration of the pharmaceutical composition comprising about 60 mg of cromolyn sodium with the inhalation device produces in the subject an AUC(0-6) of the cromolyn sodium that is within 80% to 125% of about 389 ng*hr/mL. In certain embodiments, administration of the pharmaceutical composition comprising about 60 mg of cromolyn sodium with the inhalation device produces in the subject a Cmax of the cromolyn sodium of between about 50 ng/mL and about 250 ng/mL. In certain embodiments, administration of the pharmaceutical composition comprising about 60 mg of cromolyn sodium with the inhalation device produces in the subject a Cmax of the cromolyn sodium that is within 80% to 125% of about 119 ng/mL, or about 148 ng/mL, or about 157 ng/mL. In certain embodiments, administration of the pharmaceutical composition comprising about 80 mg of cromolyn sodium with the inhalation device produces in the subject an AUC(0-∞) of the cromolyn sodium that is between about 300 ng*hr/mL and about 800 ng*hr/mL. In certain embodiments, administration of the pharmaceutical composition comprising about 80 mg of cromolyn sodium with the inhalation device produces in the subject an AUC (0-∞) of the cromolyn sodium that is within 80% to 125% of about 526 ng*hr/mL. In certain embodiments, administration of the pharmaceutical composition comprising about 80 mg of cromolyn sodium with the inhalation device produces in the subject a Cmax of the cromolyn sodium of between about 90 ng/mL and about 450 ng/mL. In certain embodiments, the inhalation device is a nebulizer. In certain embodiments, the nebulizer is a high-efficiency nebulizer. In certain embodiments, the inhalation device is a dry-powder inhaler.

The disclosure provides any of the methods disclosed herein, wherein the pharmaceutical composition is administered to the subject from once to five times per day. In certain embodiments, the pharmaceutical composition is administered to the subject once per day, or two times per day, or three times per day, or four times per day, or five times per day. In certain embodiments, the pharmaceutical composition is administered the subject once per day. In certain embodiments, the pharmaceutical composition is administered the subject twice per day. In certain embodiments, the pharmaceutical composition is administered the subject three times per day. In certain embodiments, the pharmaceutical composition is administered the subject four times per day. In certain embodiments, the pharmaceutical composition is administered the subject five times per day.

The disclosure provides a pharmaceutically acceptable composition, comprising from about 1% to about 99% by weight of cromolyn sodium, wherein an aerosol created from the pharmaceutically acceptable composition is suitable for inhalation by a subject having pulmonary fibrosis. In certain embodiments, the aerosol has a respirable fraction (≤3.3 μm) as measured by USP <1601> or USP <601> of at least about 30%. In certain embodiments, the aerosol has a respirable fraction (≤3.3 μm) as measured by USP <1601> or USP <601> of at least about 30% and a respirable fraction (≤5 μm) as measured by USP <1601> or USP <601> of at least about 75%.

The disclosure provides a pharmaceutically acceptable solution for use in the treatment of a subject having pulmonary fibrosis, comprising from about 1% to about 10% by weight of cromolyn sodium and an osmotic agent, wherein an aerosol created from the pharmaceutically acceptable solution is suitable for inhalation by a subject having pulmonary fibrosis. In certain embodiments, the aerosol has a respirable fraction (≤3.3 μm) as measured by USP <1601> of at least about 30%. In certain embodiments, the aerosol has a respirable fraction (≤3.3 μm) as measured by USP <1601> of at least about 30% and a respirable fraction (≤5 μm) as measured by USP <1601> of at least about 75%.

Dry powder inhalers for use in administering a composition or formulation of the disclosure may provide an aerosol having a respirable fraction ≤3.3 μm as measured by USP <601> of at least about 30% and a respirable fraction ≤5 μm as measured by USP <601> of at least about 65%. Dry powder inhalers for use in administering a composition or formulation of the disclosure may provide an aerosol having a respirable fraction ≤3.3 μm as measured by USP <601> of at least about 45% and a respirable fraction ≤5 μm as measured by USP <601> of at least about 75%.

The terms pharmaceutical composition, composition, solution, and formulation are used interchangeably throughout the disclosure.

In certain embodiments, in the compositions and formulations used in the treatment of a subject having pulmonary fibrosis, the ionic osmotic agent may comprise, consist essentially of, or consist of an ionic osmotic agent. In certain embodiments of the compositions and formulations of the disclosure, the ionic osmotic agent may comprise, consist essentially of, or consist of sodium chloride. In certain embodiments, the compositions and formulations comprise an ionic osmotic agent. In certain embodiments, the compositions and formulations consist essentially of an ionic osmotic agent. In certain embodiments, the compositions and formulations consist of an ionic osmotic agent. In certain embodiments, the ionic osmotic agent comprises sodium chloride. In certain embodiments, the ionic osmotic agent consists essentially of sodium chloride. In certain embodiments, the ionic osmotic agent consists of sodium chloride.

The disclosure provides any of the methods, uses, kits, dosage forms, compositions and formulations disclosed herein, wherein the ionic osmotic agent of the compositions may comprise between 0.0% and 1%, by weight, of the composition, inclusive of the endpoints. In certain embodiments, the ionic osmotic agent may comprise between 0.1% and 0.2%, by weight, of the composition, inclusive of the endpoints. In certain embodiments. In certain embodiments, the ionic osmotic agent may comprise about 0.1%, or about 0.2%, or about 0.3%, or about 0.4%, or about 0.5%, or about 0.6%, or about 0.7% by weight, of the composition. In certain embodiments, the ionic osmotic agent may comprise about 0.1%, by weight, of the composition. In certain embodiments, the ionic osmotic agent may comprise about 0.1%, by weight, of the composition. In certain embodiments, the ionic osmotic agent may comprise about 0.2%, by weight, of the composition. In certain embodiments, the ionic osmotic agent may comprise about 0.3%, by weight, of the composition. In certain embodiments, the ionic osmotic agent may comprise about 0.4%, by weight, of the composition. In certain embodiments, the ionic osmotic agent may comprise about 0.5%, by weight, of the composition. In certain embodiments, the ionic osmotic agent may comprise about 0.6%, by weight, of the composition. In certain embodiments, the ionic osmotic agent may comprise about 0.7%, by weight, of the composition. In certain embodiments, the ionic osmotic agent may comprise about 0.8%, by weight, of the composition. In certain embodiments, the ionic osmotic agent may comprise about 0.9%, by weight, of the composition. In certain embodiments, the ionic osmotic agent may comprise about 1%, by weight, of the composition.

In certain embodiments, the ionic osmotic agent may comprise 0.0%, or about 0.1%, or about 0.2%, or about 0.3%, or about 0.4%, or about 0.5%, or about 0.6%, or about 0.7% by weight, of the composition.

The disclosure provides any of the methods, uses, kits, dosage forms, compositions and formulations disclosed herein, wherein the pharmaceutical composition has an osmolality of between about 100 mOsm/kg and about 200 mOsm/kg, or between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 100 mOsm/kg and about 135 mOsm/kg, or between about 100 mOsm/kg and about 125 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg, or of between about 125 mOsm/kg and about 135 mOsm/kg. In certain embodiments, the osmolality of the formulation is about 120 mOsm/kg, about 125 mOsm/kg, about 130 mOsm/kg, about 135 mOsm/kg, about 140 mOsm/kg, about 145 mOsm/kg, or about 150 mOsm/kg. Compositions and formulations of the disclosure may have an osmolality of about 100 mOsm/kg. Compositions and formulations of the disclosure may have an osmolality of about 125 mOsm/kg. The disclosure provides any of the methods, uses, kits, dosage forms, compositions and formulations disclosed herein, wherein the pharmaceutical composition has an osmolality of about 135 mOsm/kg. The disclosure provides any of the methods, uses, kits, dosage forms, compositions and formulations disclosed herein, wherein the pharmaceutical composition has an osmolality of about 200 mOsm/kg. One of ordinary skill in the art will understand that the osmolality and the osmorsity of the solution are related.

The disclosure provides any of the methods, uses, kits, dosage forms, compositions and formulations disclosed herein, wherein the pharmaceutical composition has an osmolality of between about 50 mOsm/kg and about 200 mOsm/kg. Compositions and formulations of the disclosure may have an osmolality of about 50 mOsm/kg. Compositions and formulations of the disclosure may have osmolality of about 100 mOsm/kg.

The disclosure provides any of the methods, uses, kits, dosage forms, compositions and formulations disclosed herein, wherein the pharmaceutical composition has an osmolarity of between about 100 mOsm/L and about 200 mOsm/L, or between about 100 mOsm/L and about 175 mOsm/L, or between about 100 mOsm/L and about 170 mOsm/L, or between about 100 mOsm/L and about 165 mOsm/L, or between about 100 mOsm/L and about 160 mOsm/L, or between about 100 mOsm/L and about 150 mOsm/L, or between about 100 mOsm/L and about 135 mOsm/L, or between about 100 mOsm/L and about 125 mOsm/L, or between about 110 mOsm/L and about 150 mOsm/L, or between about 110 mOsm/L and about 140 mOsm/L, or between about 115 mOsm/L and about 140 mOsm/L, or between about 120 mOsm/L and about 140 mOsm/L, or between about 120 mOsm/L and about 130 mOsm/L, or of between about 125 mOsm/L and about 135 mOsm/L. In certain embodiments, the osmolarity of the formulation is about 120 mOsm/L, about 125 mOsm/L, about 130 mOsm/L, about 135 mOsm/L, about 140 mOsm/L, about 145 mOsm/L, or about 150 mOsm/L. In certain embodiments, the formulations disclosed herein have an osmolarity of about 100 mOsm/L. In certain embodiments, the formulations disclosed herein have an osmolarity of about 125 mOsm/L. In certain embodiments, the formulations disclosed herein have an osmolarity of about 135 mOsm/L. In certain embodiments, the formulations disclosed herein have an osmolarity of about 200 mOsm/L.

The disclosure provides any of the methods, uses, kits, dosage forms, compositions and formulations disclosed herein, wherein the pharmaceutical composition has an osmolarity of between about 50 mOsm/L and about 200 mOsm/L In certain embodiments, the osmolarity of the formulation is about 50 mOsm/L, about 120 mOsm/L, about 125 mOsm/L, about 130 mOsm/L, about 135 mOsm/L, about 140 mOsm/L, about 145 mOsm/L, or about 150 mOsm/L. In certain embodiments, the formulations disclosed herein have an osmolarity of about 50 mOsm/L.

The disclosure provides any of the methods, uses, kits, dosage forms, compositions and formulations disclosed herein, wherein the pharmaceutical composition is isotonic, hypertonic or hypotonic. In certain embodiments, the pharmaceutical composition is isotonic. In certain embodiments, the pharmaceutical composition is hypertonic. In certain embodiments, the pharmaceutical composition is hypotonic. One of ordinary skill in the art will understand that the osmolality, osmolarity and tonicity of pharmaceutical compositions are related.

Compositions and formulations used in the treatment of a subject having pulmonary fibrosis may further comprise a chelating agent. In certain embodiments, the chelating agent may comprise about 0.01%, or about 0.02%, or about 0.03%, or about 0.04%, or about 0.05%, or about 0.06%, or about 0.07%, or about 0.08%, or about 0.09%, or about 0.1%, or about 0.2%, or about 0.3%, or about 0.4%, or about 0.5%, or about 0.6%, or about 0.7%, or about 0.8% or about 0.9%, or about 1% by weight, of the composition. In certain embodiments, the chelating agent comprises ethylenediaminetetraacetic acid (EDTA), sodium-EDTA, or sodium citrate. In certain embodiments, the chelating agent comprises EDTA. In certain embodiments, the chelating agent comprises sodium-EDTA. In certain embodiments, the chelating agent comprises sodium citrate.

Compositions and formulations used in the treatment of a subject having pulmonary fibrosis may further comprise a non-ionic osmotic agent, preferably, wherein the non-ionic osmotic agent comprises or consists of mannitol.

Compositions and formulations used in the treatment of a subject having pulmonary fibrosis may exclude, or, may not comprise a non-ionic osmotic agent. In certain embodiments, compositions and formulations used in the treatment of a subject having pulmonary fibrosis may not comprise a non-ionic osmatic agent comprising or consisting of mannitol, a sugar alcohol and/or propylene glycol. In certain embodiments, compositions and formulations used in the treatment of a subject having pulmonary fibrosis, do not comprise propylene glycol, regardless of any potential functional role of the propylene glycol known to those of ordinary skill in the art.

Compositions and formulations of the disclosure may exclude, or, may not comprise a non-ionic osmotic agent. In certain embodiments, compositions of the disclosure may not comprise a non-ionic osmotic agent comprising or consisting of mannitol, any other sugar alcohol and/or propylene glycol. In certain embodiments, compositions of the disclosure do not comprise mannitol, any other sugar alcohol and/or propylene glycol, regardless of any potential functional role, chemical property or use of mannitol, any other sugar alcohol and/or propylene glycol known to those of ordinary skill in the art.

Compositions and formulations of the disclosure may have a surface tension effective for deposition, penetration or retention of the composition primarily in the peripheral lung regions, including the bronchioles and alveoli. In certain embodiments, the compositions and formulations of the disclosure may have a surface tension in the range similar to that or water or higher. In certain embodiments, the compositions and formulations according to the present disclosure has a surface tension of at least about 30 mN/m, or at least about 40 mN/m, or at least about 50 mN/m, or at least about 60 mN/m, or at least about 70 mN/m, such as in the range of about 30 mN/m to about 75 mN/m, or about 50 mN/m to about 75 mN/m, or about 70 mN/m to about 75 mN/m Compositions and formulations of the disclosure may exclude, or, may not comprise a surfactant. In certain embodiments, compositions of the disclosure may not comprise any dispersing agent, solubilizing agent, or spreading agent. Some examples of surfactants that are excluded from the present compositions and formulations include: PEG (polyethylene glycol) 400; Sodium lauryl sulfate sorbitan laurate, sorbitan palmitate, sorbitan stearate available under the tradename Span® (20-40-60 etc.); polyoxyethylene (20) sorbitan monolaurate, polyoxyethylene (20) sorbitan monopalmitate, polyoxyethylene (20) sorbitan monostearate available under the tradename Tween (polysorbates, 20-40-60 etc.); tyloxapol; propylene glycol; and Benzalkoniurn chloride, vitamin-TPGS and lecithins, (Exosurf®, GlaxoSmithKline), surfactant proteins. In certain embodiments, surfactants that are excluded from the present compositions and formulations include any compound or agent that lowers the surface tension of a composition.

Compositions and formulations used in the treatment of a subject having pulmonary fibrosis may further comprise purified water for injection. The amount of the water may vary depending upon, for example, a fill volume required for the particular high-efficiency nebulizer used. In certain embodiments, compositions and formulations used in the treatment of a subject having pulmonary fibrosis comprise purified water for injection in a quantum sufficiat (q.s.).

Compositions and formulations of the disclosure may be in the form of a solution having a fill volume of about 0.1 mL to about 5 mL.

Compositions and formulations of the disclosure may comprise from about 5 mg to about 80 mg of cromolyn sodium, inclusive of the endpoints. Compositions and formulations of the disclosure may comprise from about 36 mg to about 44 mg of cromolyn sodium, inclusive of the endpoints.

Nebulizers administering a composition or formulation of the disclosure may provide an aerosol having a respirable fraction ≤3.3 µm as measured by USP <1601> of at least about 30% and a respirable fraction ≤5 µm as measured by USP <1601> of at least about 65%. Nebulizers administering a composition or formulation of the disclosure may provide an aerosol having a respirable fraction ≤3.3 µm as measured by USP <1601> of at least about 45% and a respirable fraction ≤5 µm as measured by USP <1601> of at least about 75%.

Dry powder inhalers administering a composition or formulation of the disclosure may provide an aerosol having a respirable fraction ≤3.3 µm as measured by USP <601> of at least about 30% and a respirable fraction ≤5 µm as measured by USP <601> of at least about 65%. Nebulizers administering a composition or formulation of the disclosure may provide an aerosol having a respirable fraction ≤3.3 µm as measured by USP <601> of at least about 45% and a respirable fraction ≤5 µm as measured by USP <601> of at least about 75%.

According to the methods of the disclosure, administration of pharmaceutical compositions of the disclosure with a nebulizer may result in primarily lung deposition, and minimal deposition in other respiratory tracts, of the administered aerosol. In certain embodiments, sedimentation is the major mechanism of deposition of the aerosol. In certain embodiments, administration of pharmaceutical compositions of the disclosure with a nebulizer provides a lung deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25% to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the composition.

According to the methods of the disclosure, administration of pharmaceutical compositions of the disclosure with a nebulizer may produce in the subject an $AUC_{(0-\infty)}$ of the cromolyn sodium greater than about 150 ng*hr/mL, a $C_{max}$ of the cromolyn sodium greater than about 50 ng/mL, and a deposited lung dose of cromolyn sodium greater than about 4 mg. According to the methods of the disclosure, administration of pharmaceutical compositions of the disclosure with a nebulizer may produce in the subject an $AUC_{(0-\infty)}$ of the cromolyn sodium greater than about 175 ng*hr/mL, a $C_{max}$ of the cromolyn sodium greater than about 60 ng/mL, and a deposited lung dose of the cromolyn sodium greater than about 4 mg. According to the methods of the disclosure, administration of pharmaceutical compositions of the disclosure with a nebulizer may produce in the subject an $AUC_{(0-\infty)}$ of the cromolyn sodium greater than about 100 ng*hr/mL, a $C_{max}$ of the cromolyn sodium greater than about 40 ng/mL, and a deposited lung dose of the cromolyn sodium greater than about 4 mg.

According to the methods of the disclosure, administration of pharmaceutical compositions of the disclosure comprising about 40 mg of cromolyn sodium with a nebulizer may produce in a subject an $AUC_{(0-\infty)}$ of the cromolyn sodium that is between about 120 ng*hr/mL and about 350 ng*hr/mL.

According to the methods of the disclosure, administration of pharmaceutical compositions of the disclosure comprising about 40 mg of cromolyn sodium with a nebulizer may produce in a subject an $AUC_{(0-\infty)}$ of the cromolyn sodium that is within 80% to 125% of about 340 ng*hr/mL.

According to the methods of the disclosure, administration of pharmaceutical compositions of the disclosure comprising about 40 mg of cromolyn sodium with a nebulizer may produce in a subject an $AUC_{(0-6)}$ of the cromolyn sodium that is between about 120 ng*hr/mL and about 350 ng*hr/mL.

According to the methods of the disclosure, administration of pharmaceutical compositions of the disclosure comprising about 40 mg of cromolyn sodium with a nebulizer may produce in a subject an $AUC_{(0-6)}$ of the cromolyn sodium that is within 80% to 125% of about 237 ng*hr/mL.

According to the methods of the disclosure, administration of pharmaceutical compositions of the disclosure comprising about 40 mg of cromolyn sodium with a nebulizer may produce in a subject a Cmax of the cromolyn sodium of between about 40 ng/mL and about 150 ng/mL.

According to the methods of the disclosure, administration of pharmaceutical compositions of the disclosure comprising about 40 mg of cromolyn sodium with a nebulizer may produce in a subject a Cmax of the cromolyn sodium that is within 80% to 125% of about 85 ng/mL, or about 75 ng/mL, or about 82 ng/mL, or about 93 ng/mL.

According to the methods of the disclosure, administration of pharmaceutical compositions of the disclosure comprising about 60 mg of cromolyn sodium with a nebulizer may produce in a subject an $AUC_{(0-\infty)}$ of the cromolyn sodium that is between about 250 ng*hr/mL and about 1000 ng*hr/mL.

According to the methods of the disclosure, administration of pharmaceutical compositions of the disclosure comprising about 60 mg of cromolyn sodium with a nebulizer may produce in a subject an $AUC_{(0-\infty)}$ of the cromolyn sodium that is within 80% to 125% of about 542 ng*hr/mL.

According to the methods of the disclosure, administration of pharmaceutical compositions of the disclosure comprising about 60 mg of cromolyn sodium with a nebulizer may produce in a subject an $AUC_{(0-6)}$ of the cromolyn sodium that is between about 200 ng*hr/mL and about 700 ng*hr/mL.

According to the methods of the disclosure, administration of pharmaceutical compositions of the disclosure comprising about 60 mg of cromolyn sodium with a nebulizer may produce in a subject an $AUC_{(0-6)}$ of the cromolyn sodium that is within 80% to 125% of about 389 ng*hr/mL.

According to the methods of the disclosure, administration of pharmaceutical compositions of the disclosure comprising about 60 mg of cromolyn sodium with a nebulizer may produce in a subject a $C_{max}$ of the cromolyn sodium of between about 50 ng/mL and about 250 ng/mL.

According to the methods of the disclosure, administration of pharmaceutical compositions of the disclosure comprising about 60 mg of cromolyn sodium with a nebulizer may produce in a subject $C_{max}$ of the cromolyn sodium that is within 80% to 125% of about 134 ng/mL, or about 119 ng/mL, or about 148 ng/mL, or about 157 ng/mL.

According to the methods of the disclosure, administration of pharmaceutical compositions of the disclosure comprising about 80 mg of cromolyn sodium with a nebulizer may produce in a subject an $AUC_{(0-\infty)}$ of the cromolyn sodium that is between about 300 ng*hr/mL and about 800 ng*hr/mL.

According to the methods of the disclosure, administration of pharmaceutical compositions of the disclosure comprising about 80 mg of cromolyn sodium with a nebulizer may produce in a subject an $AUC_{(0-\infty)}$ of the cromolyn sodium that is within 80% to 125% of about 526 ng*hr/mL.

According to the methods of the disclosure, administration of pharmaceutical compositions of the disclosure comprising about 80 mg of cromolyn sodium with a nebulizer may produce in a subject a $C_{max}$ of the cromolyn sodium of between about 90 ng/mL and about 450 ng/mL.

According to the methods of the disclosure, administration of pharmaceutical compositions of the disclosure with a dry powder inhaler may produce in the subject an $AUC_{(0-\infty)}$ of the cromolyn sodium greater than about 150 ng*hr/mL, a Cmax of the cromolyn sodium greater than about 50 ng/mL, and a deposited lung dose of cromolyn sodium greater than about 4 mg.

According to the methods of the disclosure, administration of pharmaceutical compositions of the disclosure with a nebulizer may produce in the subject an $AUC_{(0-\infty)}$ of the cromolyn sodium greater than about 175 ng*hr/mL, a $C_{max}$ of the cromolyn sodium greater than about 60 ng/mL, and a deposited lung dose of the cromolyn sodium greater than about 4 mg.

According to the methods of the disclosure, administration of pharmaceutical compositions of the disclosure with a nebulizer may produce in the subject an $AUC_{(0-\infty)}$ of the cromolyn sodium greater than about 100 ng*hr/mL, a $C_{max}$ of the cromolyn sodium greater than about 40 ng/mL, and a deposited lung dose of the cromolyn sodium greater than about 4 mg.

According to the methods of the disclosure, administration of pharmaceutical compositions of the disclosure comprising about 40 mg of cromolyn sodium with a dry powder inhaler may produce in a subject an $AUC_{(0-\infty)}$ of the cromolyn sodium that is between about 120 ng*hr/mL and about 350 ng*hr/mL.

According to the methods of the disclosure, administration of pharmaceutical compositions of the disclosure comprising about 40 mg of cromolyn sodium with a dry powder inhaler may produce in a subject an $AUC_{(0-\infty)}$ of the cromolyn sodium that is within 80% to 125% of about 340 ng*hr/mL.

According to the methods of the disclosure, administration of pharmaceutical compositions of the disclosure comprising about 40 mg of cromolyn sodium with a dry powder inhaler may produce in a subject an $AUC_{(0-6)}$ of the cromolyn sodium that is between about 120 ng*hr/mL and about 350 ng*hr/mL.

According to the methods of the disclosure, administration of pharmaceutical compositions of the disclosure comprising about 40 mg of cromolyn sodium with a dry powder inhaler may produce in a subject an $AUC_{(0-6)}$ of the cromolyn sodium that is within 80% to 125% of about 237 ng*hr/mL.

According to the methods of the disclosure, administration of pharmaceutical compositions of the disclosure comprising about 40 mg of cromolyn sodium with a dry powder inhaler may produce in a subject a $C_{max}$ of the cromolyn sodium of between about 40 ng/mL and about 150 ng/mL.

According to the methods of the disclosure, administration of pharmaceutical compositions of the disclosure comprising about 40 mg of cromolyn sodium with a dry powder inhaler may produce in a subject a $C_{max}$ of the cromolyn sodium that is within 80% to 125% of about 85 ng/mL, or about 75 ng/mL, or about 82 ng/mL, or about 93 ng/mL.

According to the methods of the disclosure, administration of pharmaceutical compositions of the disclosure comprising about 60 mg of cromolyn sodium with a dry powder inhaler may produce in a subject an $AUC_{(0-\infty)}$ of the cromolyn sodium that is between about 250 ng*hr/mL and about 1000 ng*hr/mL.

According to the methods of the disclosure, administration of pharmaceutical compositions of the disclosure comprising about 60 mg of cromolyn sodium with a dry powder inhaler may produce in a subject an $AUC_{(0-\infty)}$ of the cromolyn sodium that is within 80% to 125% of about 542 ng*hr/mL.

According to the methods of the disclosure, administration of pharmaceutical compositions of the disclosure comprising about 60 mg of cromolyn sodium with a dry powder inhaler may produce in a subject an $AUC_{(0-6)}$ of the cromolyn sodium that is between about 200 ng*hr/mL and about 700 ng*hr/mL.

According to the methods of the disclosure, administration of pharmaceutical compositions of the disclosure comprising about 60 mg of cromolyn sodium with a dry powder inhaler may produce in a subject an $AUC_{(0-6)}$ of the cromolyn sodium that is within 80% to 125% of about 389 ng*hr/mL.

According to the methods of the disclosure, administration of pharmaceutical compositions of the disclosure comprising about 60 mg of cromolyn sodium with a dry powder inhaler may produce in a subject a $C_{max}$ of the cromolyn sodium of between about 50 ng/mL and about 250 ng/mL.

According to the methods of the disclosure, administration of pharmaceutical compositions of the disclosure comprising about 60 mg of cromolyn sodium with a dry powder inhaler may produce in a subject $C_{max}$ of the cromolyn sodium that is within 80% to 125% of about 134 ng/mL, or about 119 ng/mL, or about 148 ng/mL, or about 157 ng/mL.

According to the methods of the disclosure, administration of pharmaceutical compositions of the disclosure comprising about 80 mg of cromolyn sodium with a dry powder inhaler may produce in a subject an $AUC_{(0-\infty)}$ of the cromolyn sodium that is between about 300 ng*hr/mL and about 800 ng*hr/mL.

According to the methods of the disclosure, administration of pharmaceutical compositions of the disclosure comprising about 80 mg of cromolyn sodium with a dry powder inhaler may produce in a subject an $AUC_{(0-\infty)}$ of the cromolyn sodium that is within 80% to 125% of about 526 ng*hr/mL.

According to the methods of the disclosure, administration of pharmaceutical compositions of the disclosure comprising about 80 mg of cromolyn sodium with a dry powder inhaler may produce in a subject a $C_{max}$ of the cromolyn sodium of between about 90 ng/mL and about 450 ng/mL.

According to the methods of the disclosure, administration of pharmaceutical compositions of the disclosure comprising about 80 mg of cromolyn sodium with a dry powder inhaler may produce in a subject a $C_{max}$ of the cromolyn sodium that is within 80% to 125% of about 236 ng/mL.

According to the methods of the disclosure, in certain embodiments, the pharmaceutical composition is administered three times per day for at least 7 days. In certain embodiments, the pharmaceutical composition is administered three times per day for at least 14 days. In certain embodiments, the pharmaceutical composition is administered three times per day as a daily maintenance therapy (e.g. at least 7 or at least 14 days without a limit for the total length of treatment).

In certain embodiments, the pharmaceutical composition is administered once per day. In certain embodiments, the pharmaceutical composition is administered twice per day. In certain embodiments, the pharmaceutical composition is administered three times per day. In certain embodiments, the pharmaceutical composition is administered four times per day. In certain embodiments, the pharmaceutical composition is administered five times per day.

According to the methods of the disclosure, in certain embodiments, the pharmaceutical composition may be administered as a combination therapy with any other therapeutic composition for the treatment of pulmonary fibrosis a subject.

The disclosure provides any of the methods, uses, solutions, compositions, kits, and dosage forms described herein wherein the subject is suffering from pulmonary fibrosis. In certain embodiments, the subject is suffering from idiopathic pulmonary fibrosis.

DETAILED DESCRIPTION

Figure 1:
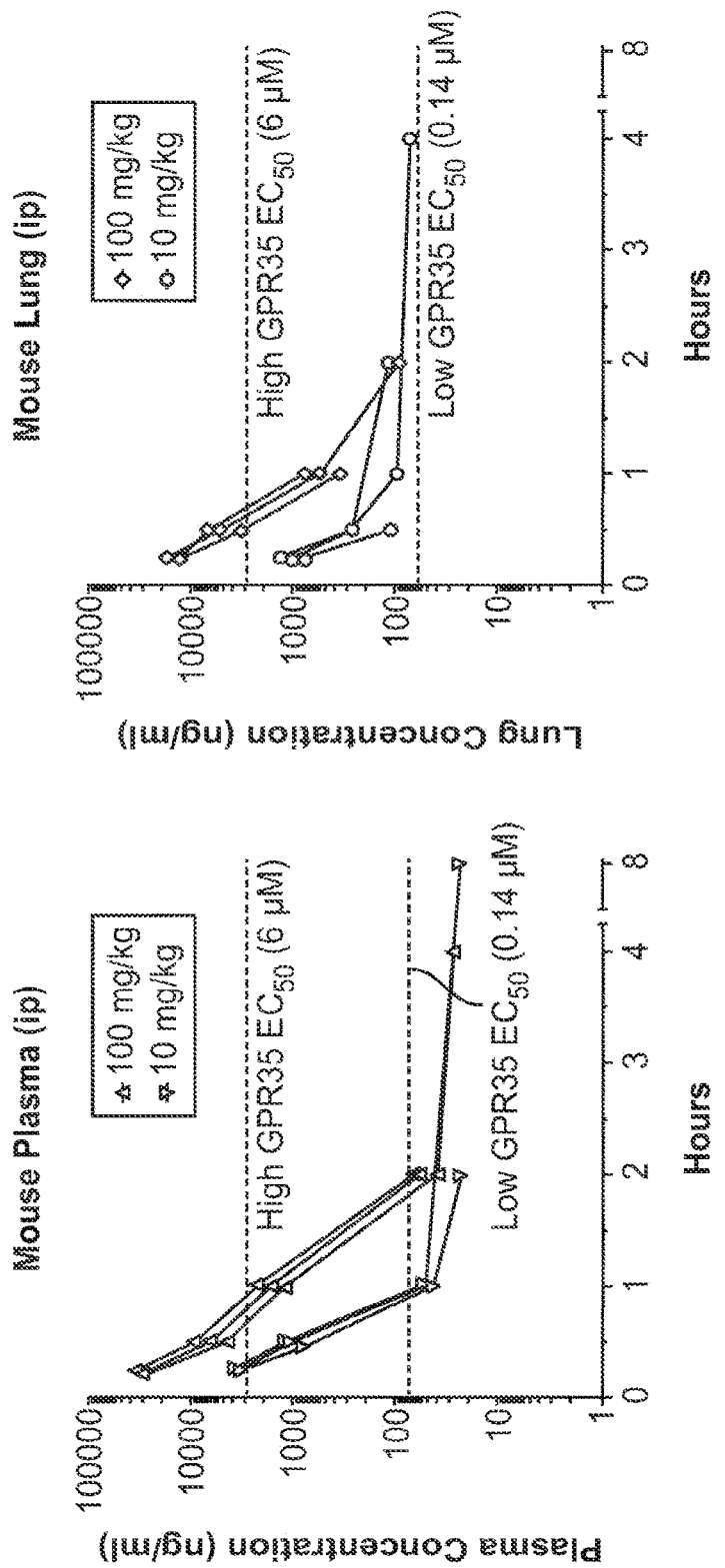
FIG. 1 is a graphic representation of the pharmacokinetic results in the plasma and lung of male BALB/c mice following a single intraperitoneal (IP) administration of cromolyn sodium at doses of 10 mg/kg and 100 mg/kg.

Unless defined otherwise, all technical and scientific terms used herein have the same meaning as commonly understood by one of skill in the art to which the inventions described herein belong. All publications, patents, and patent applications mentioned in this specification are hereby incorporated by reference to the same extent as if each individual publication, patent, or patent application was specifically and individually indicated to be incorporated by reference.

As used herein, the term "about" is used synonymously with the term "approximately." Illustratively, the use of the term "about" with regard to a certain therapeutically effective pharmaceutical dose indicates that values in a range spanning a cited value, e.g., plus or minus up to 10% of a cited value, are also effective and safe.

"$AUC_{(0-\infty)}$," as used herein refers to the total area under a blood plasma concentration curve for an active pharmaceutical ingredient (API). $AUC_{(0-\infty)}$ can be determined by methods known to those of skill in the art. For example, the $AUC_{(0-\infty)}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by liquid chromatography-tandem mass spectrometry (LC-MS/MS), plotting the concentration of API in each sample versus the time of collection after administration, and calculating the area under the curve.

"BGM" as used herein refers to biglycan degraded by MMP-2/9, as further described in Jenkins et. al., *The Lancet Respiratory Medicine*, Vol. 3, No. 6, pp. 462-472.

"Bioavailability" as used herein refers to the amount of unchanged API that reaches the systemic circulation, expressed as a percentage of the dosage of the API that is administered to a subject. By definition, the bioavailability of an intravenous solution containing the active pharmaceutical ingredient (API) is 100%. The bioavailability of an API can be determined by methods known to those of skill in the art. For example, the bioavailability of an API can be determined by collecting urine samples from a subject at various time points following administration of the API to the subject, extracting the API from the urine samples, e.g., by solid-phase extraction, quantifying the amount of the API in each urine sample, adjusting the amount of API collected from the urine by a factor based on the amount of API reaching systemic circulation that is excreted in the urine, and calculating the percentage of the API administered to the subject that reaches the systemic circulation of the subject. In a specific embodiment, the bioavailability of cromolyn sodium can be determined as described in Walker et al., 24 J. Pharm. Pharmacol. 525-31 (1972). In the case of cromolyn sodium, the amount of the compound isolated from the urine is multiplied by two to calculate the total amount reaching systemic circulation after administration because the compound is known to be excreted unmetabolized in equal parts in the urine and feces, i.e., approximately 50% of the amount of cromolyn sodium that reaches systemic circulation is excreted in the urine and approximately 50% of the amount of cromolyn sodium that reaches systemic circulation is excreted in the feces.

"Blood plasma concentration" refers to the concentration of an active pharmaceutical ingredient (API) in the plasma component of blood of a subject or subject population.

"C1M" as used herein refers to collagen 1 degraded by MMP-2/9/13, as further described in Jenkins et. al., *The Lancet Respiratory Medicine*, Vol. 3, No. 6, pp. 462-472.

"C3A" as used herein refers to collagen 3 degraded by ADAMTS-1/4/8, as further described in Jenkins et. al., *The Lancet Respiratory Medicine*, Vol. 3, No. 6, pp. 462-472.

"C3M" as used herein refers to collagen 3 degraded by MMP-9, as further described in Jenkins et. al., *The Lancet Respiratory Medicine*, Vol. 3, No. 6, pp. 462-472.

"C5M" as used herein refers to collagen 5 degraded by MMP-2/9, as further described in Jenkins et. al., *The Lancet Respiratory Medicine*, Vol. 3, No. 6, pp. 462-472.

"C6M" as used herein refers to collagen 6 degraded by MMP-2/9, as further described in Jenkins et. al., *The Lancet Respiratory Medicine*, Vol. 3, No. 6, pp. 462-472.

"$C_{max}$" as used herein refers to the maximum plasma concentration for an active pharmaceutical ingredient (API). $C_{max}$ can be determined by methods known to those of skill in the art. For example, the $C_{max}$ of an API can be determined by collecting blood samples from a subject at various time points after administration of an API to the subject, separating plasma from the blood samples, extracting the API from the separated plasma samples, e.g., by solid-phase extraction, quantifying the amount of the API extracted from each sample of separated plasma, e.g., by LC-MS/MS, plotting the concentration of API in each sample versus the time of collection after administration, and identifying the peak concentration of the API on the curve.

As used herein, the terms "comprising," "including," "such as," and "for example" (or "e.g.") are used in their open, non-limiting sense.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the invention.

"CPRM" as used herein refers to C-reactive protein degraded by MMP-1/8, as further described in Jenkins et. al., The Lancet Respiratory Medicine, Vol. 3, No. 6, pp. 462-472.

"D-dimer" as used herein refers to a specific fragment of plasmin-mediated degradation of cross-linked fibrin.

"Deposited dose" or "deposited lung dose" is the amount of cromolyn or a pharmaceutically-acceptable salt thereof deposited in the lung. The deposited dose or deposited lung dose may be expressed in absolute terms, for example in mg or µg of API deposited in the lungs. The deposited lung dose may also be expressed in relative terms, for example calculating the amount of API deposited as a percentage of the nominal dose. Lung deposition (deposited lung dose) can be determined using methods of scintigraphy or deconvolution. Since cromolyn sodium is not metabolized in the body and approximately 50% of absorbed cromolyn is excreted in urine (Auty et al, Br. J Dis. Chest Vol. 81, No. 4, 1987, 371-380), and since its oral bioavailability is very low (~1%), the deposited lung dose for cromolyn during inhalation can also be determined by measuring the cromolyn sodium content in the urine and multiplying that number by two.

"Drug absorption" or simply "absorption" typically refers to the process of movement of drug from site of delivery of a drug across a barrier into a blood vessel or the site of action, e.g., a drug being absorbed via the pulmonary capillary beds of the alveoli into the systemic circulation.

"Forced expiratory volume" (FEV) as used herein measures how much air a subject can exhale during a forced breath. The amount of air exhaled may be measured during the first (FEV1), second (FEV2), and/or third seconds (FEV3) of the forced breath. FEV can be measured by methods well known to those having ordinary skill in the art.

"Forced vital capacity" (FVC) as used herein is the total amount of air exhaled expelled by a subject during the FEV test. "% FVC" as used herein is the percent change in the FVC of a subject over a period of time. FVC and % FVC can be measured by methods well known to those having ordinary skill in the art.

"FPA" as used herein means a specific fragment of thrombin-mediated degradation of fibrinogen.

As used herein, the term "high concentration" refers to a concentration greater than 1% by weight. For example, in a specific embodiment, a "high concentration" formulation of cromolyn sodium comprises cromolyn sodium at a concentration of greater than 1% by weight.

As used herein, the term "hypotonic" refers to a formulation that has a tonicity less than 295 mOsm/kg. As used herein, the term "hypertonic" refers to a formulation that has a tonicity more than 295 mOsm/kg.

"IPF" as used herein means idiopathic pulmonary fibrosis.

As used herein, a "locally effective amount" is an amount of cromolyn or a pharmaceutically-acceptable salt thereof in a particular region of the body of a subject as a whole that is effective for the treatment or prophylactic treatment of a subject having pulmonary fibrosis, including IPF. A "locally effective amount" may be expressed, for example, as the mass of cromolyn or a pharmaceutically-acceptable salt thereof, or concentration of cromolyn or a pharmaceutically-acceptable salt thereof, in a subject's tissue. A "locally effective amount" may differ depending on the formulation of cromolyn or a pharmaceutically-acceptable salt thereof.

"Nebulizer," as used herein, refers to a device that turns medications, compositions, formulations, suspensions, and mixtures, etc. into a fine aerosol mist for delivery to the lungs.

"Nominal dose," as used herein, refers to the loaded dose, which is the amount of active pharmaceutical ingredient (API) in an inhalation device prior to administration to the subject. The volume of solution containing the nominal dose is referred to as the "fill volume."

The term "prophylaxis" refers to administration of an active pharmaceutical ingredient to a subject with the purpose of reducing the occurrence or recurrence of one or more acute symptoms associated with a disease state or a condition in the subject. In the present context, prophylaxis entails administering cromolyn or a pharmaceutically-acceptable salt thereof to a subject via any route of administration disclosed herein. Thus, prophylaxis includes reduction in the progression of pulmonary fibrosis, including IPF, in a subject.

"Substantially the same nominal dose" as used herein means that a first nominal dose of an active pharmaceutical ingredient (API) contains approximately the same number of millimoles of the cromolyn or a pharmaceutically-acceptable salt thereof as a second nominal dose of the cromolyn or a pharmaceutically-acceptable salt thereof.

"Subject" or "subject" refers to the animal (especially mammal) or human being treated.

As used herein, a "systemically effective amount" is an amount of cromolyn or a pharmaceutically-acceptable salt thereof in the body of a subject as a whole that is effective for the treatment or prophylactic treatment of a subject having pulmonary fibrosis, including IPF. A "systemically effective amount" may be expressed, for example, as the mass of cromolyn or a pharmaceutically-acceptable salt thereof, or concentration of cromolyn or a pharmaceutically-acceptable salt thereof, in a subject's plasma. A "systemically effective amount" may differ depending on the formulation of cromolyn or a pharmaceutically-acceptable salt thereof.

"$T_{max}$" as used herein refers to the amount of time necessary for an active pharmaceutical ingredient (API) to attain maximum blood plasma concentration.

The term "treat" and its grammatical variants (e.g., "to treat," "treating," and "treatment") refer to administration of an active pharmaceutical ingredient to a subject with the purpose of ameliorating or reducing the incidence of one or more symptoms of a condition or disease state in the subject. Such symptoms may be chronic or acute; and such amelioration may be partial or complete. In the present context, treatment entails administering cromolyn or a pharmaceutically-acceptable salt thereof to a subject via any route of administration disclosed herein.

As used herein, a difference is "significant" if a person skilled in the art would recognize that the difference is probably real. In certain embodiments, significance may be determined statistically, in which case two measured parameters may be referred to as statistically significant. In certain embodiments, statistical significance may be quantified in terms of a stated confidence interval (CI), e.g., greater than 90%, greater than 95%, greater than 98%, etc. In certain embodiments, statistical significance may be quantified in terms of a p value, e.g., less than 0.5, less than 0.1, less than 0.05, etc. The person skilled in the art will recognize these expressions of significance and will know how to apply them appropriately to the specific parameters that are being compared.

"VICM" as used herein refers to citrullinated vimentin degraded by MMP-2/8, as further described in Jenkins et. al., *The Lancet Respiratory Medicine*, Vol. 3, No. 6, pp. 462-472.

Compositions of the disclosure comprising cromolyn sodium and an ionic osmotic agent are safe and efficacious for the treatment of subjects having pulmonary fibrosis, including IPF.

Cromolyn, and Analogs, Derivatives, and Pharmaceutically Acceptable Salts Thereof As used herein, cromolyn refers to disodium 5,5'-(2-hydroxypropane-1,3-diyl)bis(oxy)bis(4-oxo-4H-chromene-2-carboxylate) and has the following structure:

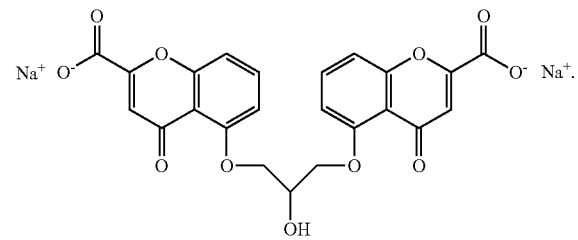

Cromolyn is also known as sodium cromolyn, cromoglicic acid, disodium cromoglicate (DSCG), sodium cromoglicate, and cromoglicate. Pharmaceutically acceptable salts of cromolyn include but are not limited to cromolyn sodium, cromolyn lysinate, ammonium cromonglycate, and magnesium cromoglycate. Cromolyn sodium is also known as disodium 5,5'-[(2-hydroxytrimethylene)dioxy]bis [4-oxo-4H-1-benzopyran-2-carboxylate].

Cromolyn and the pharmaceutically acceptable salts described herein may be prepared as prodrugs. A "prodrug" refers to an agent that is converted into the parent drug in vivo. The prodrug can be designed to alter the metabolic stability or the transport characteristics of a drug, to mask side effects or toxicity, to improve the flavor of a drug, or to alter other characteristics or properties of a drug. In certain embodiments, the prodrug has improved bioavailability relative to the parent drug. In certain embodiments, the prodrug has improved solubility in pharmaceutical compositions over the parent drug. In certain embodiments, prodrugs may be designed as reversible drug derivatives, for use as modifiers to enhance drug transport to site-specific tissues. In certain embodiments, a prodrug of cromolyn is an ester of cromolyn, which is hydrolyzed to the carboxylic acid, the parent compound. In certain embodiments, a prodrug comprises a short peptide (polyaminoacid) bonded to an acid group, wherein the peptide is metabolized in vivo to reveal the parent drug. In certain embodiments, upon in vivo administration, a prodrug is chemically converted to the biologically, pharmaceutically or therapeutically active form of cromolyn. In certain embodiments, a prodrug is enzymatically metabolized by one or more steps or processes to the parent compound. In certain embodiments, prodrug of cromolyn is used. In a specific embodiment, the prodrug of cromolyn is cromoglicate lisetil.

To produce a prodrug, a pharmaceutically active cromolyn is modified such that the active compound will be regenerated upon in vivo administration. In certain embodiments, prodrugs of cromolyn are designed by virtue of knowledge of pharmacodynamic processes and drug metabolism in vivo. See, e.g., Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006.

In certain embodiments, cromolyn and pharmaceutically acceptable salts thereof disclosed herein are isotopically-labeled compounds, which are identical to those recited herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically labeled compounds described herein, for example those with isotopes such as deuterium, i.e., $^{2}H$, can afford certain therapeutic advantages resulting from greater metabolic stability, such as, for example, increased in vivo half-life or reduced dosage requirements. In certain embodiments, isotopically labeled cromolyn is co-administered. In some, the pharmaceutically acceptable salt of cromolyn, such as cromolyn sodium, is isotopically labeled. In certain embodiments, the pharmaceutically acceptable salt of cromolyn is deuterium-labeled cromolyn sodium.

In certain embodiments, cromolyn and the pharmaceutically acceptable salt thereof described herein are pegylated, wherein one or more polyethylene glycol (PEG) polymers are covalently attached to cromolyn or the pharmaceutically acceptable salt thereof. In certain embodiments, pegylation increases the half-life of the pegylated compound in the body. In certain embodiments, pegylation increases the hydrodynamic size of the pegylated compound and reduces renal clearance. In certain embodiments, pegylation increases the solubility of the pegylated compound. In certain embodiments, protects the pegylated compound from proteolytic degradation.

Cromolyn and pharmaceutically acceptable salts, prodrugs, and adducts thereof, may be prepared by methods known in the art.

Cromolyn or a pharmaceutically acceptable salt thereof may be administered in the methods disclosed herein in a suitable dose or nominal dose as determined by one of ordinary skill in the art. In certain embodiments, cromolyn or a pharmaceutically acceptable salt thereof is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, about 30 mg/dose to about 50 mg/dose, or greater than about 100 mg/dose. In certain embodiments, cromolyn or a pharmaceutically acceptable salt thereof is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In certain embodiments, cromolyn or a pharmaceutically acceptable salt thereof is administered in about 10 mg. In certain embodiments, cromolyn or a pharmaceutically acceptable salt thereof is administered in about 20 mg. In certain embodiments, cromolyn or a pharmaceutically acceptable salt thereof is administered in about 30 mg. In certain embodiments, cromolyn or a pharmaceutically acceptable salt thereof is administered in about 40 mg. In certain embodiments, cromolyn or a pharmaceutically acceptable salt thereof is administered in about 50 mg. In certain embodiments, cromolyn or a pharmaceutically acceptable salt thereof is administered in about 60 mg. In certain embodiments, cromolyn or a pharmaceutically acceptable salt thereof is administered in about 70 mg. In certain embodiments, cromolyn or a pharmaceutically acceptable salt thereof is administered in about 80 mg.

In certain embodiments of the methods disclosed herein, cromolyn sodium is administered at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, or about 30 mg/dose to about 50 mg/dose, or greater than about 100 mg/dose. In other embodiments, cromolyn sodium is administered in less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In certain embodiments, cromolyn or a pharmaceutically acceptable salt thereof is administered in about 30 mg. In certain embodiments, cromolyn or a pharmaceutically acceptable salt thereof is administered in about 40 mg. In certain embodiments, cromolyn or a pharmaceutically acceptable salt thereof is administered in about 50 mg. In certain embodiments, cromolyn or a pharmaceutically acceptable salt thereof is administered in about 60 mg. In certain embodiments, cromolyn or a pharmaceutically acceptable salt thereof is administered in about 70 mg. In certain embodiments, cromolyn or a pharmaceutically acceptable salt thereof is administered in about 80 mg.

Formulations

DSCG has a long history of use for its anti-allergy, anti-inflammatory, and immune-modulating properties as well as its exceptional safety profile. However, the available formulations of DSCG (that do not include the compositions of the disclosure) are not suitable for use in the treatment of subjects having pulmonary fibrosis, including IPF, because the available formulations of DSCG are too limited by poor delivery efficiency and very low bioavailability (approximately 1%).

The compositions and formulations of the disclosure enhance bioavailability and provide efficacious treatment of the debilitating symptoms of pulmonary fibrosis, including IPF. The compositions and formulations of the disclosure achieve significantly higher lung and peripheral distribution than currently available formulations, parameters that are both required for efficacy in treatment of subjects having pulmonary fibrosis, including IPF.

Table A provides exemplary, nonlimiting, formulations of the compositions of the disclosure, wherein the amounts of each component of the formulations are expressed as weight percent of the total weight of the formulation.

TABEL A

| Component | Function | PA101 (wt %) | PA101B (wt %) | PA101B (wt %) | PA101B (wt %) |
|---|---|---|---|---|---|
| Cromolyn | Active Substance | 4 | 2 OR 4 OR 6 | 4 | 6 |
| Sodium Chloride | Osmotic Agent | 0.2 | 0.0 | 0.2 | 0.2 |
| EDTA | Chelating Agent | 0.02 | 0.02 | 0.02 | 0.02 |
| Mannitol | Non-ionic Osmotic Agent | 1.25 | 0.0 | 0 | 0 |
| Water for Injection (WFI) | Quantum sufficiat (q.s.) | q.s. | qs | q.s. | q.s. |
| Osmolality (mOsm/kg) | Tonicity | 200 | 42 OR 75 OR 105 | 125 | 135 |

Table B provides further exemplary, nonlimiting, formulations of the compositions of the disclosure, wherein the amounts of each component of the formulations are expressed as weight percent of the total weight of the formulation.

TABLE B

| Formulation | Cromolyn sodium (%) | Mannitol (%) | Sodium chloride (%) | EDTA (%) | Osmolality (mOsm/kg) |
|---|---|---|---|---|---|
| 1 | 2 | 0 | 0 | 0.02 | 42 |
| 2 | 2 | 0 | 0.2 | 0.02 | 106 |
| 3 | 2 | 0 | 0.4 | 0.02 | 170 |
| 4 | 2 | 0 | 0.6 | 0.02 | 235 |
| 5 | 2 | 0 | 0.8 | 0.02 | 299 |
| 6 | 4 | 0 | 0 | 0.02 | 75 |
| 7 | 4 | 1.25 | 0.2 | 0.02 | 199 |
| 8 | 4 | 1 | 0.2 | 0.02 | 183 |
| 9 | 4 | 0.75 | 0.2 | 0.02 | 169 |
| 10 | 4 | 0.5 | 0.2 | 0.02 | 154 |
| 11 | 4 | 0.25 | 0.2 | 0.02 | 139 |
| 12 | 4 | 0 | 0.2 | 0.02 | 125 |
| 13 | 5 | 0 | 0 | 0.02 | 95 |
| 14 | 5 | 1.25 | 0.2 | 0.02 | 207 |
| 15 | 5 | 0 | 0.2 | 0.02 | 131 |
| 16 | 5 | 0 | 0.25 | 0.02 | 147 |
| 17 | 6 | 0 | 0 | 0.02 | 105 |
| 18 | 6 | 1.25 | 0.2 | 0.02 | 214 |
| 19 | 6 | 0 | 0.2 | 0.02 | 138 |
| 20 | 6 | 0 | 0.25 | 0.02 | 154 |

PA101B formulations 4% by weight and 6% by weight, are each highly concentrated, well-tolerated, room-temperature stable formulations of disodium cromoglycate optimized for delivery via an electronic nebulizer.

In certain embodiments, compositions of the disclosure may comprise an ionic osmolarity or osmolality adjusting agent but, do not comprise a non-ionic osmolarity or osmolality adjusting agent. Ionic osmolarity or osmolality adjusting agents can be selected from, for example, alkali metal salts, such as sodium and potassium salts. Examples of such salts include, hut are not limited to, sodium chloride, sodium gluconate, sodium pyruvate, and potassium chloride. It is possible to use a single ionic tonicity-adjusting agent, such as sodium chloride, or a mixture of such agents. The salts may be either added or formed in situ due to a salt formation process. In a particular embodiment of the disclosure, however, the non-ionic osmolarity or osmolality adjusting agent is mannitol. The non-ionic osmolarity or osmolality adjusting agent can be selected from, for example, the group of carbohydrates. Examples of carbohydrates that can be used for isotonisation include, but are not limited to, sugars such as glucose, lactose, sucrose and trehalose, and sugar alcohols such as mannitol, xylitol, sorbitol, and isomaltol. In a particular embodiment of the disclosure, however, the non-ionic osmolarity or osmolality adjusting agent is not propylene glycol, a cyclodextrin or mannitol.

In certain embodiments, formulations administered in the methods disclosed herein produce in a subject $AUC_{(0-\infty)}$ of cromolyn or a pharmaceutically acceptable salt thereof greater than about 100 ng*hr./mL, greater than about 110 ng*hr./mL, greater than about 120 ng*hr./mL, greater than about 130 ng*hr./mL, greater than about 140 ng*hr./mL, greater than about 150 ng*hr./mL, greater than about 160 ng*hr./mL, greater than about 170 ng*hr./mL, greater than about 180 ng*hr./mL, greater than about 190 ng*hr./mL, greater than about 200 ng*hr./mL, greater than about 225 ng*hr./mL, greater than about 250 ng*hr./mL, greater than about 275 ng*hr./mL, greater than about 300 ng*hr./mL, greater than about 325 ng*hr./mL, greater than about 350 ng*hr./mL, greater than about 375 ng*hr./mL, greater than about 400 ng*hr./mL, greater than about 425 ng*hr./mL, greater than about 450 ng*hr./mL, greater than about 475 ng*hr./mL, greater than about 500 ng*hr./mL, greater than about 525 ng*hr./mL, greater than about 550 ng*hr./mL, greater than about 575 ng*hr./mL, greater than about 600 ng*hr./mL, greater than about 625 ng*hr./mL, greater than about 650 ng*hr./mL, greater than about 675 ng*hr./mL, greater than about 700 ng*hr./mL, greater than about 725 ng*hr./mL, greater than about 750 ng*hr./mL, greater than about 775 ng*hr./mL, greater than about 800 ng*hr./mL, greater than about 825 ng*hr./mL, greater than about 850 ng*hr./mL, greater than about 875 ng*hr./mL, greater than about 900 ng*hr./mL, greater than about 925 ng*hr./mL, greater than about 950 ng*hr./mL, greater than about 975 ng*hr./mL, or greater than about 1000 ng*hr./mL after administration of the formulation to the subject. In certain embodiments, formulations administered in the methods disclosed herein produce in a subject an $AUC_{(0-\infty)}$ of cromolyn or a pharmaceutically-acceptable salt thereof greater than about 100 ng*hr./mL, greater than about 110 ng*hr./mL, greater than about 120 ng*hr./mL, greater than about 130 ng*hr./mL, greater than about 140 ng*hr./mL, greater than about 150 ng*hr./mL, greater than about 160 ng*hr./mL, greater than about 170 ng*hr./mL, greater than about 180 ng*hr./mL, greater than about 190 ng*hr./mL, greater than about 200 ng*hr./mL, greater than about 225 ng*hr./mL, greater than about 250 ng*hr./mL, greater than about 275 ng*hr./mL, greater than about 300 ng*hr./mL, greater than about 325 ng*hr./mL, greater than about 350 ng*hr./mL, greater than about 375 ng*hr./mL, greater than about 400 ng*hr./mL, greater than about 425 ng*hr./mL, greater than about 450 ng*hr./mL, greater than about 475 ng*hr./mL, greater than about 500 ng*hr./mL, greater than about 525 ng*hr./mL, greater than about 550 ng*hr./mL, greater than about 575 ng*hr./mL, greater than about 600 ng*hr./mL, greater than about 625 ng*hr./mL, greater than about 650 ng*hr./mL, greater than about 675 ng*hr./mL, greater than about 700 ng*hr./mL, greater than about 725 ng*hr./mL, greater than about 750 ng*hr./mL, greater than about 775 ng*hr./mL, greater than about 800 ng*hr./mL, greater than about 825 ng*hr./mL, greater than about 850 ng*hr./mL, greater than about 875 ng*hr./mL, greater than about 900 ng*hr./mL, greater than about 925 ng*hr./mL, greater than about 950 ng*hr./mL, greater than about 975 ng*hr./mL, or greater than about 1000 ng*hr./mL after administration of the formulation to the subject or subject.

In certain embodiments, formulations administered in the methods disclosed herein produce in a subject $AUC_{(0-\infty)}$ of cromolyn or a pharmaceutically-acceptable salt thereof of about 100 ng*hr./mL, about 110 ng*hr./mL, about 120 ng*hr./mL, about 130 ng*hr./mL, about 140 ng*hr./mL, about 150 ng*hr./mL, about 160 ng*hr./mL, about 170 ng*hr./mL, about 180 ng*hr./mL, about 190 ng*hr./mL, about 200 ng*hr./mL, about 225 ng*hr./mL, about 250 ng*hr./mL, about 275 ng*hr./mL, about 300 ng*hr./mL, about 325 ng*hr./mL, about 350 ng*hr./mL, about 375 ng*hr./mL, about 400 ng*hr./mL, about 425 ng*hr./mL, about 450 ng*hr./mL, about 475 ng*hr./mL, about 500 ng*hr./mL, about 525 ng*hr./mL, about 550 ng*hr./mL, about 575 ng*hr./mL, about 600 ng*hr./mL, about 625 ng*hr./mL, about 650 ng*hr./mL, about 675 ng*hr./mL, about 700 ng*hr./mL, about 725 ng*hr./mL, about 750 ng*hr./mL, about 775 ng*hr./mL, about 800 ng*hr./mL, about 825 ng*hr./mL, about 850 ng*hr./mL, about 875 ng*hr./mL, about 900 ng*hr./mL, about 925 ng*hr./mL, about 950 ng*hr./mL, about 975 ng*hr./mL, or about 1000 ng*hr./mL after administration of the formulation to the subject. In certain embodiments, formulations administered in the methods disclosed herein produce in a subject an $AUC_{(0-\infty)}$ of cromolyn or a pharmaceutically-acceptable salt thereof of about 100 ng*hr./mL, about 110 ng*hr./mL, about 120 ng*hr./mL, about 130 ng*hr./mL, about 140 ng*hr./mL, about 150 ng*hr./mL, about 160 ng*hr./mL, about 170 ng*hr./mL, about 180 ng*hr./mL, about 190 ng*hr./mL, about 200 ng*hr./mL, about 225 ng*hr./mL, about 250 ng*hr./mL, about 275 ng*hr./mL, about 300 ng*hr./mL, about 325 ng*hr./mL, about 350 ng*hr./mL, about 375 ng*hr./mL, about 400 ng*hr./mL, about 425 ng*hr./mL, about 450 ng*hr./mL, about 475 ng*hr./mL, about 500 ng*hr./mL, about 525 ng*hr./mL, about 550 ng*hr./mL, about 575 ng*hr./mL, about 600 ng*hr./mL, about 625 ng*hr./mL, about 650 ng*hr./mL, about 675 ng*hr./mL, about 700 ng*hr./mL, about 725 ng*hr./mL, about 750 ng*hr./mL, about 775 ng*hr./mL, about 800 ng*hr./mL, about 825 ng*hr./mL, about 850 ng*hr./mL, about 875 ng*hr./mL, about 900 ng*hr./mL, about 925 ng*hr./mL, about 950 ng*hr./mL, about 975 ng*hr./mL, or about 1000 ng*hr./mL after administration of the formulation to the subject or subject.

In certain embodiments, formulations administered in the methods disclosed herein produce in a subject an $AUC_{(0-\infty)}$ of cromolyn sodium greater than about 100 ng*hr./mL, greater than about 110 ng*hr./mL, greater than about 120 ng*hr./mL, greater than about 130 ng*hr./mL, greater than about 140 ng*hr./mL, greater than about 150 ng*hr./mL, greater than about 160 ng*hr./mL, greater than about 170 ng*hr./mL, greater than about 180 ng*hr./mL, greater than about 190 ng*hr./mL, greater than about 200 ng*hr./mL, greater than about 225 ng*hr./mL, greater than about 250 ng*hr./mL, greater than about 275 ng*hr./mL, greater than about 300 ng*hr./mL, greater than about 325 ng*hr./mL, greater than about 350 ng*hr./mL, greater than about 375 ng*hr./mL, greater than about 400 ng*hr./mL, greater than about 425 ng*hr./mL, greater than about 450 ng*hr./mL, greater than about 475 ng*hr./mL, greater than about 500 ng*hr./mL, greater than about 525 ng*hr./mL, greater than about 550 ng*hr./mL, greater than about 575 ng*hr./mL, greater than about 600 ng*hr./mL, greater than about 625 ng*hr./mL, greater than about 650 ng*hr./mL, greater than about 675 ng*hr./mL, greater than about 700 ng*hr./mL, greater than about 725 ng*hr./mL, greater than about 750 ng*hr./mL, greater than about 775 ng*hr./mL, greater than about 800 ng*hr./mL, greater than about 825 ng*hr./mL, greater than about 850 ng*hr./mL, greater than about 875 ng*hr./mL, greater than about 900 ng*hr./mL, greater than about 925 ng*hr./mL, greater than about 950 ng*hr./mL, greater than about 975 ng*hr./mL, or greater than about 1000 ng*hr./mL after administration of the formulation to the subject. In certain embodiments, formulations administered in the methods disclosed herein produce in a subject an $AUC_{(0-\infty)}$ of cromolyn sodium greater than about 100 ng*hr./mL, greater than about 110 ng*hr./mL, greater than about 120 ng*hr./mL, greater than about 130 ng*hr./mL, greater than about 140 ng*hr./mL, greater than about 150 ng*hr./mL, greater than about 160 ng*hr./mL, greater than about 170 ng*hr./mL, greater than about 180 ng*hr./mL, greater than about 190 ng*hr./mL, greater than about 200 ng*hr./mL, greater than about 225 ng*hr./mL, greater than about 250 ng*hr./mL, greater than about 275 ng*hr./mL, greater than about 300 ng*hr./mL, greater than about 325 ng*hr./mL, greater than about 350 ng*hr./mL, greater than about 375 ng*hr./mL, greater than about 400 ng*hr./mL, greater than about 425 ng*hr./mL, greater than about 450 ng*hr./mL, greater than about 475 ng*hr./mL, greater than about 500 ng*hr./mL, greater than about 525 ng*hr./mL, greater than about 550 ng*hr./mL, greater than about 575 ng*hr./mL, greater than about 600 ng*hr./mL, greater than about 625 ng*hr./mL, greater than about 650 ng*hr./mL, greater than about 675 ng*hr./mL, greater than about 700 ng*hr./mL, greater than about 725 ng*hr./mL, greater than about 750 ng*hr./mL, greater than about 775 ng*hr./mL, greater than about 800 ng*hr./mL, greater than about 825 ng*hr./mL, greater than about 850 ng*hr./mL, greater than about 875 ng*hr./mL, greater than about 900 ng*hr./mL, greater than about 925 ng*hr./mL, greater than about 950 ng*hr./mL, greater than about 975 ng*hr./mL, or greater than about 1000 ng*hr./mL after administration of the formulation to the subject or subject.

In certain embodiments, formulations administered in the methods disclosed herein produce in a subject an $AUC_{(0-\infty)}$ of cromolyn sodium of about 100 ng*hr./mL, about 110 ng*hr./mL, about 120 ng*hr./mL, about 130 ng*hr./mL, about 140 ng*hr./mL, about 150 ng*hr./mL, about 160 ng*hr./mL, about 170 ng*hr./mL, about 180 ng*hr./mL, about 190 ng*hr./mL, about 200 ng*hr./mL, about 225 ng*hr./mL, about 250 ng*hr./mL, about 275 ng*hr./mL, about 300 ng*hr./mL, about 325 ng*hr./mL, about 350 ng*hr./mL, about 375 ng*hr./mL, about 400 ng*hr./mL, about 425 ng*hr./mL, about 450 ng*hr./mL, about 475 ng*hr./mL, about 500 ng*hr./mL, about 525 ng*hr./mL, about 550 ng*hr./mL, about 575 ng*hr./mL, about 600 ng*hr./mL, about 625 ng*hr./mL, about 650 ng*hr./mL, about 675 ng*hr./mL, about 700 ng*hr./mL, about 725 ng*hr./mL, about 750 ng*hr./mL, about 775 ng*hr./mL, about 800 ng*hr./mL, about 825 ng*hr./mL, about 850 ng*hr./mL, about 875 ng*hr./mL, about 900 ng*hr./mL, about 925 ng*hr./mL, about 950 ng*hr./mL, about 975 ng*hr./mL, or about 1000 ng*hr./mL after administration of the formulation to the subject. In certain embodiments, formulations administered in the methods disclosed herein produce in a subject an $AUC_{(0-\infty)}$ of cromolyn sodium of about 100 ng*hr./mL, about 110 ng*hr./mL, about 120 ng*hr./mL, about 130 ng*hr./mL, about 140 ng*hr./mL, about 150 ng*hr./mL, about 160 ng*hr./mL, about 170 ng*hr./mL, about 180 ng*hr./mL, about 190 ng*hr./mL, about 200 ng*hr./mL, about 225 ng*hr./mL, about 250 ng*hr./mL, about 275 ng*hr./mL, about 300 ng*hr./mL, about 325 ng*hr./mL, about 350 ng*hr./mL, about 375 ng*hr./mL, about 400 ng*hr./mL, about 425 ng*hr./mL, about 450 ng*hr./mL, about 475 ng*hr./mL, about 500 ng*hr./mL, about 525 ng*hr./mL, about 550 ng*hr./mL, about 575 ng*hr./mL, about 600 ng*hr./mL, about 625 ng*hr./mL, about 650 ng*hr./mL, about 675 ng*hr./mL, about 700 ng*hr./mL, about 725 ng*hr./mL, about 750 ng*hr./mL, about 775 ng*hr./mL, about 800 ng*hr./mL, about 825 ng*hr./mL, about 850 ng*hr./mL, about 875 ng*hr./mL, about 900 ng*hr./mL, about 925 ng*hr./mL, about 950 ng*hr./mL, about 975 ng*hr./mL, or about 1000 ng*hr./mL after administration of the formulation to the subject.

In certain embodiments, formulation administered in the methods disclosed herein produce in a subject a Cmax of cromolyn or a pharmaceutically-acceptable salt thereof greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject. In certain embodiments, formulations administered in the methods disclosed herein produce in a subject a $C_{max}$ of cromolyn or a pharmaceutically-acceptable salt thereof greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject or subject.

In certain embodiments, formulations administered in the methods disclosed herein produce in a subject a Cmax of cromolyn or a pharmaceutically-acceptable salt thereof of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject. In certain embodiments, formulations administered in the methods disclosed herein produce in a subject a $C_{max}$ of cromolyn or a pharmaceutically-acceptable salt thereof of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject or subject.

In certain embodiments, formulations administered in the methods disclosed herein produce in a subject a Cmax of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject. In certain embodiments, formulations administered in the methods disclosed herein produce in a subject a $C_{max}$ of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject or subject.

In certain embodiments, formulations administered in the methods disclosed herein produce in a subject a Cmax of cromolyn sodium of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject. In certain embodiments, formulations administered in the methods disclosed herein produce in a subject a $C_{max}$ of cromolyn sodium of about 50 mg/mL, about 60 ng/mL, about 70 ng/mL, about 80 ng/mL, 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject or subject.

Cromolyn or a pharmaceutically acceptable salt thereof may be administered to a subject in the methods disclosed herein with an inhalation device, e.g., a nebulizer.

Cromolyn or a pharmaceutically acceptable salt thereof may be formulated into any suitable dosage form, including but not limited to aerosols, aqueous oral dispersions, self-emulsifying dispersions, liposomal dispersions, pegylated liposomes, liquids, elixirs, suspensions, aerosols, controlled release formulations, lyophilized formulations, powders, delayed release formulations, extended release formulations, multiparticulate formulations or mixed immediate release formulations. Such formulations may be manufactured in a conventional manner, such as, by way of example only, conventional mixing, dissolving, or granulating processes.

In certain embodiments, the formulations disclosed herein may include one or more inactive ingredients or pharmaceutical excipients that provide suitable properties of the formulation. Such inactive ingredients may include one or more of the following classes.

"Albumin" refers to a family of globular proteins, the most common of which is serum albumin. Albumins are commonly found in blood plasma and function to regulate colloidal osmotic pressure of the blood. Albumin proteins found in the plasma bind some pharmaceutical compounds to form complexes. Complexation of albumin with pharmaceutical compounds, e.g., cromolyn or a pharmaceutical salt thereof, can influence the pharmaceutical compounds' plasma half-life and/or biological half-life in the body by preventing metabolism and/or excretion of the complexed compounds. In certain embodiments, compositions disclosed herein include albumin and cromolyn or a pharmaceutical salt thereof (e.g. cromolyn sodium).

"Antifoaming agents" reduce foaming during processing which can result in coagulation of aqueous dispersions, bubbles in the finished film, or generally impair processing. Exemplary anti-foaming agents include silicon emulsions or sorbitan sesquoleate "Antioxidants" include, for example, butylated hydroxytoluene (BHT), sodium ascorbate, ascorbic acid, sodium metabisulfite and tocopherol. In certain embodiments, antioxidants enhance chemical stability where required.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidine (e.g., Polyvidone® CL, Kollidon® CL, Polyplasdone® XL-10), larch arabogalactan, Veegum®, polyethylene glycol, waxes, sodium alginate, and the like.

"Carriers" or "carrier materials" include any commonly used excipients in pharmaceutics and should be selected on the basis of compatibility with cromolyn or a pharmaceutically acceptable salt thereof and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy, Nineteenth Ed* (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Dispersing agents" and/or "viscosity modulating agents" include materials that control the diffusion and homogeneity of a drug through liquid media or a granulation method or blend method. In certain embodiments, these agents also facilitate the effectiveness of a coating or eroding matrix. Exemplary diffusion facilitators/dispersing agents include, e.g., hydrophilic polymers, electrolytes, Tween® 60 or 80, PEG, Tyloxapol, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidylcholine, natural phosphatidyl choline from eggs, natural phosphatidyl glycerol from eggs, cholesterol and isopropyl myristate.

"Diluent" refers to chemical compounds that are used to dilute the compound of interest (i.e. cromolyn or a pharmaceutically acceptable salt thereof) prior to delivery. Diluents can also be used to stabilize compounds because they can provide a more stable environment. Salts dissolved in buffered solutions, including, but not limited to, a phosphate buffered saline solution, are utilized as diluents in the art, and can also provide pH control or maintenance. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dentomint, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In certain embodiments, plasticizers can also function as dispersing agents or wetting agents.

In certain embodiments, compositions provided herein may also include one or more preservatives to inhibit microbial activity. Suitable preservatives include mercury-containing substances such as merfen and thiomersal; stabilized chlorine dioxide; octinidine; and quaternary ammonium compounds such as benzalkonium chloride, cetyltrimethylammonium bromide and cetylpyridinium chloride.

"Solubilizers" include compounds such as triacetin, triethylcitrate, ethyl oleate, ethyl caprylate, sodium lauryl sulfate, sodium doccusate, vitamin E TPGS, polysorbates (Tweens) dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, e.g., citric acid, EDTA and pharmaceutically acceptable salts thereof, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In certain embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans, and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Compositions and formulations of the disclosure may have a surface tension effective for deposition, penetration or retention of the composition primarily in the peripheral lung regions, including the bronchioles and alveoli. In certain embodiments, the compositions and formulations of the disclosure may have a surface tension in the range similar to that or water or higher. In certain embodiments, the compositions and formulations according to the present disclosure has a surface tension of at least about 30 mN/m, or at least about 40 mN/m, or at least about 50 mN/m, or at least about 60 mN/m, or at leat about 70 mN/m. In some embodiments, the compositions and formulations has a surface tension in the range of about 30 mN/m to about 75 mN/m, or about 50 mN/m to about 75 mN/m, or about 70 mN/m to about 75 mN/m.

Compositions and formulations of the disclosure may exclude, or, may not comprise a surfactant. In certain embodiments, compositions of the disclosure may not comprise any dispersing agent, solubilizing agent, or spreading agent. Some examples of surfactants that are excluded from the present compositions and formulations include: PEG (polyethylene glycol) 400; Sodium lauryl sulfate sorbitan laurate, sorbitan palmitate, sorbitan stearate available under the tradename Spans® (20-40-60 etc.); polyoxyethylene (20) sorbitan monolaurate, polyoxyethylene (20) sorbitan monopalmitate, polyoxyethylene (20) sorbitan monostearate available under the tradename Tweense (polysorbates, 20-40-60 etc.); tyloxapol; propylene glycol; and Benzalkonium chloride, vitamin-TPGS and lecithins, (Exosurf®, GlaxoSmithKline), surfactant proteins. In certain embodiments, surfactants that are excluded from the present compositions and formulations include any compound or agent that lowers the surface tension of a composition.

It should be appreciated that there is considerable overlap between classes of inactive ingredients. Thus, the above-listed ingredients should be taken as merely exemplary, and not limiting, of the types of inactive ingredients that can be included in formulations described herein. The amounts of such inactive ingredients can be readily determined by one skilled in the art, according to the particular properties desired.

Liquid Oral Formulations

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., *Encyclopedia of Pharmaceutical Technology, 2nd Ed.*, pp. 754-757 (2002). In addition to the particles of cromolyn or a pharmaceutically-acceptable salt thereof, the liquid dosage forms may include additives, such as: (a) disintegrating agents; (b) dispersing agents; (c) wetting agents; (d) at least one preservative, (e) viscosity enhancing agents, (0 at least one sweetening agent, and (g) at least one flavoring agent. In certain embodiments, the aqueous dispersions can further include a crystalline inhibitor. In certain embodiments, systemically effective amounts of cromolyn or a pharmaceutically-acceptable salt thereof are achieved with liquid oral formulations by including permeation enhancers in the liquid oral formulations.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In certain embodiments, the dispersing agents suitable for the aqueous suspensions and dispersions described herein include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Inhalation Therapy

An "inhalation device," as used herein, refers to any device that is capable of administering a drug formulation to the respiratory airways of a subject. Inhalation devices include conventional inhalation devices such as nebulizers, metered dose inhalers (MDIs), dry powder inhalers (DPIs), jet nebulizers, ultrasonic wave nebulizers, heat vaporizers, and soft mist inhalers. Inhalation devices also include nebulizers. Nebulizers, metered dose inhalers, and soft mist inhalers deliver pharmaceuticals by forming an aerosol which includes droplet sizes that can easily be inhaled. The aerosol can be used by a subject within the bounds of an inhalation therapy, whereby the cromolyn or a pharmaceutically-acceptable salt thereof reaches the subject's respiratory tract upon inhalation. In certain embodiments, the methods disclosed herein comprise administering to a subject a nominal dose of cromolyn or a pharmaceutically-acceptable salt thereof by an inhalation device, such as a nebulizer. In certain embodiments of the methods disclosed herein, an inhalation device is not a bronchoscope.

In certain embodiments of the methods disclosed herein, administration of a composition comprising cromolyn or a pharmaceutically acceptable salt thereof, e.g., cromolyn sodium, to a subject with an inhalation device, e.g., a nebulizer, a dry powder inhaler, a metered dose inhaler, a thermal aerosol inhaler, or an electrohydrodynamic-based solution misting inhaler, is effective for the treatment or prophylaxis of pulmonary fibrosis in a subject having pulmonary fibrosis, including IPF, because both a systemically effective amount of the cromolyn or a pharmaceutically acceptable salt thereof and a high deposited lung dose of the cromolyn or a pharmaceutically acceptable salt thereof is achieved in the subject. Thus, in certain embodiments of the methods disclosed herein, administration of a composition comprising cromolyn or a pharmaceutically acceptable salt thereof, e.g., cromolyn sodium, to a subject with an inhalation device, e.g., a nebulizer, a dry powder inhaler, a metered dose inhaler, a thermal aerosol inhaler, or an electrohydrodynamic-based solution misting inhaler, is effective for the treatment or prophylaxis of pulmonary fibrosis in a subject, including IPF, that may not be believed to be susceptible to treatment or prophylaxis with cromolyn or a pharmaceutically acceptable salt thereof because both a systemically effective amount of the cromolyn or a pharmaceutically acceptable salt thereof and a high deposited lung dose of the cromolyn or a pharmaceutically acceptable salt thereof are achieved in the subject. Furthermore, in certain embodiments where cromolyn or a pharmaceutically acceptable salt thereof is administered with an inhalation device, e.g., a nebulizer, a dry powder inhaler, a metered dose inhaler, a thermal aerosol inhaler, or an electrohydrodynamic-based solution misting inhaler, the methods disclosed herein provide improved efficacy for the treatment or prophylaxis of pulmonary fibrosis, including IPF, in a subject relative to administration of a systemically effective amount of the cromolyn or a pharmaceutically acceptable salt thereof by a different route of administration, e.g., parenterally or orally, because administration of the cromolyn or a pharmaceutically acceptable salt thereof with an inhalation device, e.g., a nebulizer, a dry powder inhaler, a metered dose inhaler, a thermal aerosol inhaler, or an electrohydrodynamic-based solution misting inhaler, provides both a systemically effective amount of the cromolyn or a pharmaceutically acceptable salt thereof and a high deposited lung dose of the cromolyn or a pharmaceutically acceptable salt thereof in the subject. In certain embodiments, a systemically effective amount of cromolyn or a pharmaceutically acceptable salt thereof is achieved by delivering the cromolyn or a pharmaceutically acceptable salt thereof in an aerosol generated by a vibrating mesh nebulizer that produces droplets with a MMD of 3.0-4.0 μm and a GSD of 1.5-1.8. In certain embodiments of the methods disclosed herein, an aerosol is administered through a mouthpiece of a nebulizer using normal tidal breathing.

Characterization of Inhalation Devices

The efficiency of a particular inhalation device can be characterized in many different ways, including by pharmacokinetic properties, lung deposition (deposited lung dose), respirable dose (RD), delivered dose (DD), respirable fraction (RF), respirable drug delivery rate (RDDR), volumetric or mass median diameter (VMD or MMD), mass median aerodynamic diameter (MMAD) in combination with the geometric standard deviation (GSD), and total output rate (TOR), among others. The MMAD and GSD can be measured using a cascade impactor as described in United States Pharmacopeia (USP <1601> or USP <601>). The DD can be measured by using breath simulation apparatus as described in USP<1601> or USP <601>. The RF is derived from measuring the amount of drug deposited on the cascade impactor plates with a particular cut-off particle size, and expressing that as a fraction of the total amount deposited on the cascade impactor plates, the induction port and the filter. The RD is calculated by multiplying the DD by the RF. The TOR is measured by the difference in weight of a nebulizer before and after completion of nebulization divided by the duration of nebulization. VMD or MMD can be measured with a standard laser light scattering apparatus such as the Malvern Spraytec.

The RF is derived from measuring the amount of drug deposited on the cascade impactor plates with a particular cut-off particle size, and expressing that as a fraction of the total amount deposited on the cascade impactor plates, the induction port and the filter. Thus, RF refers to a distribution of particles of an aerosol indicative of the percentages of the total mass or volume of the aerosol that are contained in particles of certain sizes. Such a mass/volume distribution expressed as the resipirable fraction (RF) is different from a distribution based on the percentages of the total number of particles in the aerosol that have certain particle sizes.

Since it takes fewer large particles to equal the mass or volume of a large number of small particles, a number distribution of particles contained in an aerosol can be markedly different from a mass distribution of the same particles in the same aerosol. As a simplified numerical example, consider an aerosol containing in total 9 particles: three 1 μm particles, three 2 μm particles, and three 3 μm particles, in size (diameter). Building a number distribution for these particles will generate a distribution where each particle size accounts for one third of the total. Yet, building a mass distribution for the same particles will generate a distribution, where 75% of the total mass/volume of the aerosol comes from the 3 μm particles, and less than 3% comes from the 1 μm particles. This is determined as follows: the volume of a spherical particle of diameter d is 4/3*π*(d/2)3. The volumes of the 1 μm, 2 μm and 3 μm particles would therefore be 0.52μ3, 4.2μ3, and 14.13μ3. Assuming unit density for all particles, these numbers would also represent the mass of the particles. Thus, the 3 μm particles would constitute 100*14.13/(0.52+4.2+14.13) =74.96% of the total mass. Likewise, the 2 μm particles will constitute 22.3% of the total mass and the 1 μm particles will be 2.8% of the total mass.

Pharmacokinetics is concerned with the uptake, distribution, metabolism and excretion of a drug substance in a subject. A pharmacokinetic profile comprises one or more biological measurements designed to measure the absorption, distribution, metabolism and excretion of a drug substance in a subject. One way of visualizing a pharmacokinetic profile is by means of a blood plasma concentration curve, which is a graph depicting mean active ingredient blood plasma concentration in a subject on the Y-axis and time (usually in hours) on the X-axis. Some pharmacokinetic parameters that may be visualized by means of a blood plasma concentration curve include $AUC_{last}$, $AUC_{(0-\infty)}$, $C_{max}$, $T_{1/2}$, and $T_{max}$. An enhanced pharmacokinetic profile in a subject can be indicated by increased $AUC_{last}$, $AUC_{(0-\infty)}$, $C_{max}$, or $T_{1/2}$, a decreased $T_{max}$, or an increased $T_{max}$. Enhanced levels of cromolyn or a pharmaceutically-acceptable salt thereof in the blood plasma of a subject may result in better control of or improved symptoms in a subject having pulmonary fibrosis, including IPF.

The deposited lung dose may be expressed as a percentage of the nominal dose that is deposited in the lung of a subject. For example, a lung deposition of 30% means 30% of the nominal dose is deposited in the lung of a subject. Likewise, a lung deposition of 60% means 60% of the nominal dose is deposited in the lung of a subject, and so forth. Lung deposition (deposited lung dose) can be determined using methods of scintigraphy or deconvolution.

RF, DD, RD, and RDDR are calculated parameters based on in vitro data that provide technical dimensions for the efficiency of an inhalation device. RF represents the percentage of the delivered aerosol, or inhaled mass, that penetrates into the gas-exchange region of the lungs. RF may be measured with a cascade impactor or laser diffraction apparatus. RF is expressed herein as the percentage of an aerosol delivered with an inhalation device that has a particular particle diameter or range of particle diameters. For example, the term "RF (≤3.3 μm)" as used herein refers to the percentage of an aerosol delivered with an inhalation device that has a particle diameter less than or equal to 3.3 μm. Similarly, the terms "RF (≤1-5 μm)" and "RF (≤5 μm)" as used herein refer to the percentage of an aerosol delivered with an inhalation device that has a particle diameter in the range of 1 μm to 5 μm, or less than 5 μm, respectively. DD is the portion or percentage of the nominal dose that is actually emitted from the mouthpiece of the device. The difference between the nominal dose and the DD is the amount of drug lost primarily as residues, i.e., the amount of drug remaining in the inhalation device after administration or lost in aerosol form during exhalation. RD is an expression of the delivered mass of drug contained within droplets or particles having a certain diameter emitted from an inhalation device, such as a DPI, MDI, or nebulizer, that are small enough to penetrate into the lung of a subject. The RD is determined by multiplying the DD by the RF. RDDR is the speed at which a respirable dose of the drug is delivered to a subject's lungs. RDDR, measured as a function of g/min or mg/min, is determined by dividing the RD by the amount of time necessary for inhalation. The amount of time necessary for inhalation is measured as the amount of time from the first moment of administration of the emitted droplet or powder from the nebulizer, DPI, or MDI until the emitted or delivered droplet or powder of a respirable diameter is delivered to the lung.

Aerosol particle/droplet size is one factor determining the deposition of aerosol drugs in the airways. The distribution of aerosol particle/droplet size can be expressed in terms of one or more of VMD/MMAD and GSD. GSD is a dimensionless measure of a droplet size distribution curve relevant for characterizing terms such as VMD, MMD, and MMAD. In general, the smaller the GSD for a particular particle size distribution, the narrower the distribution curve.

Inhalation Devices

Inhalation devices may be mechanical or electrical, and include, for example, jet nebulizers, and ultrasonic nebulizers. Jet nebulizers generally utilize compressors to generate compressed air, which breaks the liquid medication into small breathable droplets, which form an aerosolized (atomized) mist. In certain embodiments, when the subject breathes in, a valve at the top opens, which then allows air into the apparatus, thereby speeding up the mist generation; when the subject breathes out, the top valve closes, thereby slowing down the mist generation while simultaneously permitting the subject to breathe out through the opening of a mouthpiece flap. Some nebulizers may provide the aerosol in a continuous mode (e.g., the eFlow from PARI Pharma Starnberg), by a breath enhanced mode (e.g., the PART LC Plus or Sprint from PARI Starnberg), by breath actuated mode dependent on the breathing pattern of the subject (e.g., the AeroEclipse from Trudell, Canada or the I-Neb from Philips Respironics), or according to given inhalation profile (e.g., the Akita from Activaero, Gmuenden, Germany).

Some conventional inhalation devices are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety. Commercial conventional inhalation devices are available from: PARI (Germany) under the trade names PARI LC Plus®, LC Star®, and PARI-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

In certain embodiments of the methods disclosed herein, compositions comprising cromolyn or a pharmaceutically-acceptable salt thereof are administered with a dry powder inhaler. In certain embodiments of the methods disclosed herein, compositions administered with dry powder inhalers comprise one or more of nanoparticles, spray dried materials, engineered porous particles with low mass median diameter but a high geometric diameter, liposomes, and stealth (or PEGylated) liposomes. In certain embodiments, compositions administered by dry powder inhalers administered in the methods disclosed herein comprise nanoparticle clusters that aggregate into micrometer sized particles at neutral or basic pH but dissociate into nanoparticles at the pH encountered in the lung. In certain embodiments the nanoparticle clusters comprise fumaryl diketopiperazine. In certain embodiments, compositions administered with dry powder inhalers comprise lactose. In certain embodiments, compositions administered with dry powder inhalers do not comprise lactose. In certain embodiments, compositions administered with a dry powder inhaler have a MMAD between 2 and 4 µm, a GSD between 1.5 and 2.5 µm, and an RF (≤5 μm) between 30% and 80%. In certain embodiments, a dry powder inhaler used to administer an inhalation formulation in the methods disclosed herein comprises a pre-metered dose, such as Plastiape Monodose inhaler, which comprises a capsule pre-filled with a powder. In certain embodiments, a dry powder inhaler used to administer an inhalation formulation in the methods disclosed herein has a device-metered system such as Twisthaler, sold by Schering Plough, which comprises a reservoir to store a powder and a twisting top to dispense each dose. Inhalation formulations for administration with a dry powder inhaler may be prepared by blending cromolyn or a pharmaceutically acceptable salt thereof, e.g., cromolyn sodium, with lactose, or spray drying cromolyn or a pharmaceutically acceptable salt thereof, e.g., cromolyn sodium, or by pelletizing cromolyn or a pharmaceutically acceptable salt thereof, e.g., cromolyn sodium, to form free-flowing spherical agglomerates.

In certain embodiments of the methods disclosed herein, compositions comprising cromolyn or a pharmaceutically acceptable salt thereof are administered with a metered dose inhaler. In certain embodiments, a composition administered with a metered dose inhaler in the methods disclosed herein comprises one or more of nanoparticles, spray dried materials, engineered porous particles with low mass median diameter but a high geometric diameter, liposomes, and stealth (or PEGylated) liposomes.

In certain embodiments of the methods disclosed herein, compositions comprising cromolyn or a pharmaceutically acceptable salt thereof are administered with a thermal aerosol inhaler. In certain embodiments, the aerosol in a thermal aerosol inhaler is generated by directly heating and vaporizing a thin solid film of the cromolyn or a pharmaceutically acceptable salt thereof, e.g., cromolyn sodium, or by heating and vaporizing a solution of cromolyn or a pharmaceutically acceptable salt thereof, e.g., cromolyn sodium in solvents such as propylene glycol and/or glycerol and water.

In certain embodiments of the methods disclosed herein, compositions comprising cromolyn or a pharmaceutically acceptable salt thereof are administered with an electrohydrodynamic-based solution misting inhaler. In certain embodiments, the aerosol in the electrohydrodynamic-based solution-misting inhaler is generated by subjecting a solution of cromolyn or a pharmaceutically acceptable salt thereof, e.g., cromolyn sodium, or a liposome or pegylated liposome comprising cromolyn or a pharmaceutically acceptable salt thereof, e.g., cromolyn sodium, to electrohydrodynamic forces through electrostatic energy.

Nebulizers

Nebulizers are inhalation devices that comprise a microperforated membrane through which a liquid solution is converted through electrical or mechanical means into aerosol droplets suitable for inhalation. Nebulizers can deliver a large fraction of a loaded dose to a subject. In certain embodiments, the nebulizer also utilizes one or more actively or passively vibrating microperforated membranes. In certain embodiments, the nebulizer contains one or more oscillating membranes. In certain embodiments, the nebulizer contains a vibrating mesh or plate with multiple apertures and optionally a vibration generator with an aerosol mixing chamber. In some such embodiments, the mixing chamber functions to collect (or stage) the aerosol from the aerosol generator. In certain embodiments, an inhalation valve is also used to allow an inflow of ambient air into the mixing chamber during an inhalation phase and is closed to prevent escape of the aerosol from the mixing chamber during an exhalation phase. In some such embodiments, the exhalation valve is arranged at a mouthpiece which is removably mounted at the mixing chamber and through which the subject inhales the aerosol from the mixing chamber. Still yet, in certain embodiments, the nebulizer contains a pulsating membrane. In certain embodiments, the nebulizer is continuously operating.

In certain embodiments, the nebulizer contains a vibrating micro-perforated membrane of tapered nozzles that generates a plume of droplets without the need for compressed gas. In these embodiments, a solution in the micro-perforated membrane nebulizer is in contact with a membrane, the opposite side of which is open to the air. The membrane is perforated by a large number of nozzle orifices of an atomizing head. An aerosol is created when alternating acoustic pressure in the solution is built up in the vicinity of the membrane causing the fluid on the liquid side of the membrane to be emitted through the nozzles as uniformly sized droplets.

Certain embodiments of nebulizers use passive nozzle membranes and a separate piezoelectric transducer that stimulates the membrane. In contrast, some nebulizers employ an active nozzle membrane, which use the acoustic pressure in the nebulizer to generate very fine droplets of solution via the high frequency vibration of the nozzle membrane.

Some nebulizers contain a resonant system. In some such nebulizers, the membrane is driven by a frequency for which the amplitude of the vibrational movement at the center of the membrane is particularly large, resulting in a focused acoustic pressure in the vicinity of the nozzle; the resonant frequency may be about 100 kHz. A flexible mounting is used to keep unwanted loss of vibrational energy to the mechanical surroundings of the atomizing head to a minimum. In certain embodiments, the vibrating membrane of the nebulizer may be made stainless steel, or of a nickel-palladium alloy by electroforming.

In certain embodiments, a nebulizer may be adapted or adaptable to operate in conjunction with a unit dosage form, such as an ampule or vial, which contains a single dose of composition comprising cromolyn or a pharmaceutically-acceptable salt thereof for the treatment of a subject having pulmonary fibrosis, including IPF. The unit dosage form comprises a container that contains an inhalation formulation comprising the cromolyn or a pharmaceutically-acceptable salt thereof, such as cromolyn sodium. The container is adapted to cooperate with the nebulizer device in such a way as to permit administration of the nominal dose of the inhalation formulation to a subject. In certain embodiments, the nebulizer and the unit dosage form are configured so that they are useable together, but not with other devices or dosage forms. In some particular embodiments, the unit dosage form is configured such that it fits into a keyhole-like structure in the nebulizer, but will not operate with other nebulizer devices. In such embodiments, the nebulizer is configured such that it will accept and properly operate with the unit dosage form containing the cromolyn or a pharmaceutically-acceptable salt thereof, but not with other dosage forms.

Commercial high efficiency nebulizers are available from: PARI (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name Micro-Air®; Activaero (Germany) under the trade name Akita®, and AerovectRx (Atlanta, Ga.) under the trade name AerovectRx®.

In certain embodiments, the methods disclosed herein comprise administration to a subject a nominal dose of cromolyn or a pharmaceutically-acceptable salt thereof with a nebulizer, wherein administration of the nominal dose of the cromolyn or a pharmaceutically-acceptable salt thereof to the subject provides one or more of the following advantages: (1) an enhanced pharmacokinetic profile as compared to administration of an oral solution; (2) an enhanced therapeutic effect as compared to administration of an oral solution; (3) an enhanced lung deposition (deposited lung dose) as compared with some inhalation devices used with other cromolyn sodium compositions evidenced by scintigraphy or deconvolution, or derived from suitable in vitro indicators such as enhanced RD, RDDR, RF, and lower GSDs, as compared to administration with some inhalation devices used with other cromolyn sodium compositions; (4) reduced administration times, periods, and/or volumes as compared to administration with some other formulations and inhalation devices; (5) a reduction in adverse side effects associated with oral formulations of cromolyn or a pharmaceutically-acceptable salt thereof, such as gastrointestinal irritation; and (6) a longer duration of therapeutic effect as compared to administration of an oral solution or an inhaled formulations using other formulations of cromolyn sodium with other inhalation devices.

In certain embodiments, the DD expressed as the percentage of the nominal dose of cromolyn or a pharmaceutically-acceptable salt thereof administered with a nebulizer in the methods disclosed herein is at least about 30%, at least about 35%, at least about 40%, at least about 45%, at least about 50%, at least about 55%, at least about 60%, at least about 65%, about 65%, about 70%, about 30% to about 90%, about 40% to about 80%, about 45% to about 75%, about 50% to about 70%, about 30% to about 75%, about 40% to about 70%, about 45% to about 60%, or about 60% to about 70%.

TOR is the speed at which the liquid containing cromolyn or a pharmaceutically-acceptable salt thereof is administered from the inhalation device. In certain embodiments, administration of the cromolyn or a pharmaceutically-acceptable salt thereof with the nebulizer provides a TOR of at least about 2 times, 3 times or 4 times the TOR achievable with a conventional inhalation device, such as a nebulizer. For example, in certain embodiments the TOR is at least about at least about 150 mg/min, at least about 200 mg/min, at least about 250 mg/min, at least 300 mg/min, at least 350 mg/min, at least 400 mg/min, at least 500 mg/min, or from 200 to about 700 mg/min.

In certain embodiments, use of a nebulizer in the methods disclosed herein provides an aerosol of a solution comprising cromolyn or a pharmaceutically-acceptable salt thereof, wherein the aerosol exhibits an RF (≤3.3 µm) of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In certain embodiments, use of a nebulizer in the methods disclosed herein provides an aerosol of a solution comprising cromolyn or a pharmaceutically-acceptable salt thereof, wherein the aerosol exhibits an RF (≤3.3 µm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 40% to about 50%, about 35% to about 45%, about 35% to about 50%, about 30% to about 50%, about 44%, or about 36%. In certain embodiments, the solution comprises an osmotic agent comprising sodium chloride. In certain embodiments, the solution comprises an osmotic agent consisting of sodium chloride. In certain embodiments, the osmolality of the solution is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the solution is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments, use of a nebulizer in the methods disclosed herein provides an aerosol of a solution comprising cromolyn or a pharmaceutically-acceptable salt thereof, wherein the aerosol exhibits an RF (1-5 µm) of cromolyn or a pharmaceutically-acceptable salt thereof of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In certain embodiments, use of a nebulizer in the methods disclosed herein provides an aerosol of a solution comprising cromolyn or a pharmaceutically-acceptable salt thereof, wherein the aerosol exhibits an RF (1-5 µm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, or about 55% to about 90%. In certain embodiments, the solution comprises an osmotic agent comprising sodium chloride. In certain embodiments, the solution comprises an osmotic agent consisting of sodium chloride. In certain embodiments, the solution comprises an osmotic agent comprising sodium chloride. In certain embodiments, the solution comprises an osmotic agent consisting of sodium chloride. In certain embodiments, the osmolality of the solution is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the solution is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments, use of a nebulizer in the methods disclosed herein provides an aerosol of a solution comprising cromolyn or a pharmaceutically-acceptable salt thereof, wherein the aerosol exhibits an RF (≤5 µm) of an cromolyn or a pharmaceutically-acceptable salt thereof of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, or about 75%. In certain embodiments, use of a nebulizer in the methods disclosed herein provides an aerosol of a solution comprising cromolyn or a pharmaceutically-acceptable salt thereof, wherein the aerosol exhibits an RF (≤5 µm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, about 65% to about 75%, about 65% to about 80%, about 60% to about 80%, about 66%, or about 75%. In certain embodiments, the solution comprises an osmotic agent comprising sodium chloride. In certain embodiments, the solution comprises an osmotic agent consisting of sodium chloride. In certain embodiments, the osmolality of the solution is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the solution is about 120 mOsm/kg, about 125 mOsm/kg, about 130 mOsm/kg, about 135 mOsm/kg, about 140 mOsm/kg, about 145 mOsm/kg, or about 150 mOsm/kg.

The disclosure provides a pharmaceutically acceptable solution, comprising from about 1% to about 10% by weight of cromolyn sodium an osmotic agent, wherein the osmotic agent consists of sodium chloride, wherein an aerosol created from the pharmaceutically acceptable solution is suitable for inhalation by a subject having pulmonary fibrosis, including IPF. In certain embodiments, the aerosol has a respirable fraction (≤3.3 µm) as measured by USP <1601> of at least about 30%. In certain embodiments, the aerosol has a respirable fraction (≤3.3 µm) as measured by USP <1601> of at least about 30% and a respirable fraction (≤5 µm) as measured by USP <1601> of at least about 75%. In certain embodiments, the pharmaceutically acceptable solution comprises about 1%, or about 2%, or about 3%, or about 4%, or about 5%, or about 6%, or about 7%, or about 8%, or about 9%, or about 10% by weight of cromolyn sodium. In certain embodiments, the osmotic agent comprises an ionic osmotic agent and excludes any non-ionic osmotic agent. In certain embodiments, the osmotic agent consists of sodium chloride. In certain embodiments, the osmolality of the solution is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the solution is about 120 mOsm/kg, about 125 mOsm/kg, about 130 mOsm/kg, about 135 mOsm/kg, about 140 mOsm/kg, about 145 mOsm/kg, or about 150 mOsm/kg.

The disclosure provides any of the methods or pharmaceutically acceptable solutions disclosed herein wherein the pharmaceutically acceptable solution has an osmolality of less than about 250 mOsm/kg, or less than about 225 mOsm/kg, or less than about 200 mOsm/kg, or less than about 190 mOsm/kg, or less than about 180 mOsm/kg, or less than about 175 mOsm/kg, or less than about 170 mOsm/kg, or less than about 165 mOsm/kg, or less than about 160 mOsm/kg, or less than about 155 mOsm/kg, or less than about 150 mOsm/kg, or less than about 145 mOsm/kg, or less than about 140 mOsm/kg, or less than about 135 mOsm/kg, or less than about 130 mOsm/kg, or less than about 125 mOsm/kg, or less than about 120 mOsm/kg, or less than about 115 mOsm/kg, or less than about 110 mOsm/kg, or less than about 105 mOsm/kg, or less than about 100 mOsm/kg. In certain embodiments, the pharmaceutically acceptable solution has an osmolality of between about 70 mOsm/kg and about 200 mOsm/kg, or between about 70 mOsm/kg and about 190 mOsm/kg, or between about 70 and about 180 mOsm/kg, or between about 70 mOsm/kg and about 170 mOsm/kg, or between about 70 mOsm/kg and about 160 mOsm/kg, or between about 70 mOsm/kg and about 150 mOsm/kg, or between about 70 mOsm/kg and about 140 mOsm/kg, or between about 80 mOsm/kg and about 200 mOsm/kg, or between about 80 mOsm/kg and about 190 mOsm/kg, or between about 90 mOsm/kg and about 180 mOsm/kg, or between about 90 mOsm/kg and about 175 mOsm/kg, or between about 90 mOsm/kg and about 170 mOsm/kg, or between about 90 mOsm/kg and about 160 mOsm/kg, or between about 100 mOsm/kg and about 150 mOsm/kg, or between about 110 mOsm/kg and about 160 mOsm/kg, or between about 100 mOsm/kg and about 160 mOsm/kg, or between about 110 mOsm/kg and about 145 mOsm/kg, or between about 110 mOsm/kg and about 140 mOsm/kg, or between about 110 mOsm/kg and about 135 mOsm/kg, or between about 120 mOsm/kg and about 140 mOsm/kg. In certain embodiments, the osmolality of the pharmaceutically acceptable solution is about 100 mOsm/kg, or about 110 mOsm/kg, or about 115 mOsm/kg, or about 120 mOsm/kg, or about 125 mOsm/kg, or about 130 mOsm/kg, or about 135 mOsm/kg, or about 140 mOsm/kg, or about 145 mOsm/kg, or about 150 mOsm/kg, or about 155 mOsm/kg, or about 160 mOsm/kg, or about 165 mOsm/kg, or about 170 mOsm/kg, or about 175 mOsm/kg, or about 180 mOsm/kg, or about 185 mOsm/kg, or about 190 mOsm/kg, or about 195 mOsm/kg, or about 200 mOsm/kg.

The disclosure provides a pharmaceutically acceptable solution, comprising from about 2% to about 6% by weight of cromolyn sodium and an osmolarity adjusting agent consisting of sodium chloride, wherein an aerosol created from the pharmaceutically acceptable solution is suitable for inhalation by a subject in need thereof. In certain embodiments, the aerosol exhibits an RF ($\leq 3.3$ μm) as measured by USP <1601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF ($\leq 5$ μm) as measured by USP <1601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%.

The disclosure provides a pharmaceutically acceptable aerosol, comprising droplets of a solution comprising from about 1% to about 10% by weight of cromolyn sodium and an osmolarity adjusting agent consisting of sodium chloride. In certain embodiments, the aerosol exhibits an RF ($\leq 3.3$ μm) as measured by USP <1601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF ($\leq 5$ μm) as measured by USP <1601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%. In certain embodiments, the osmolality of the solution is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the solution is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments, the solution of the disclosure may exclude, or, may not comprise a surfactant. In certain embodiments, the solution of the disclosure may not comprise any dispersing agent, solubilizing agent, or spreading agent. Some examples of surfactants that are excluded from the present compositions and formulations include: PEG (polyethylene glycol) 400; Sodium lauryl sulfate sorbitan laurate, sorbitan palmitate, sorbitan stearate available under the tradename Span® (20-40-60 etc.); polyoxyethylene (20) sorbitan monolaurate, polyoxyethylene (20) sorbitan monopalmitate, polyoxyethylene (20) sorbitan monostearate available under the tradename Tween (polysorbates, 20-40-60 etc.); tyloxapol; propylene glycol; and Benzalkonium chloride, vitamin-TPGS and lecithins, (Exosurf®, GlaxoSmithKline), surfactant proteins. In certain embodiments, surfactants that are excluded from the present solution include any compound or agent that lowers the surface tension of a composition.

In certain embodiments, use of a nebulizer in the methods disclosed herein provides an aerosol that comprises particles having a surface tension suitable for deposition, penetration or retention of the composition primarily in the peripheral lung regions, including the bronchioles and alveoli. In certain embodiments, use of a nebulizer in the methods disclosed herein provides an aerosol of a solution that comprises particles having a surface tension in the range similar to that or water or higher. In certain embodiments, use of a nebulizer in the methods disclosed herein provides an aerosol of a solution that comprises particles having a surface tension of at least about 30 mN/m, or at least about 40 mN/m, or at least about 50 mN/m, or at least about 60 mN/m, or at leat about 70 mN/m. In some embodiments, use of a nebulizer in the methods disclosed herein provides an aerosol of a solution that comprises particles having a surface tension in the range of about 30 mN/m to about 75 mN/m, or about 50 mN/m to about 75 mN/m, or about 70 mN/m to about 75 mN/m.

The disclosure provides a method of administering a therapeutically effective amount of cromolyn sodium to a subject in need thereof, comprising administering to the subject a pharmaceutical composition comprising from about 2% to about 6% by weight of cromolyn sodium and an osmotic agent consisting of sodium chloride, wherein the pharmaceutical composition is administered to the subject by inhalation in the form of an aerosol exhibiting an RF (≤5 µm) as measured by USP <1601> of at least about 60%. In certain embodiments, the aerosol exhibits an RF (≤3.3 μm) as measured by USP <1601> of at least about 30%. In certain embodiments, the aerosol exhibits an RF (≤3.3 μm) as measured by USP <1601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF (≤5 μm) as measured by USP <1601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%. In certain embodiments, the osmolality of the pharmaceutical composition is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the pharmaceutical composition is about 120 mOsm/kg, about 125 mOsm/kg, about 130 mOsm/kg, about 135 mOsm/kg, about 140 mOsm/kg, about 145 mOsm/kg, or about 150 mOsm/kg.

The disclosure provides a dosage form, comprising (a) a pharmaceutical composition comprising from about 2% by weight to about 99% by weight of cromolyn sodium; and (b) an inhalation device for the administration of the pharmaceutical composition to a subject, wherein said dosage form is suitable for the treatment of a subject having pulmonary fibrosis. In certain embodiments, the pharmaceutical composition comprises from about 2% by weight to about 6% by weight of cromolyn sodium and an ionic osmotic agent and the inhalation device is a nebulizer. In certain embodiments, the nebulizer is a high-efficiency nebulizer. In certain embodiments, the pharmaceutical composition comprises from about 2% by weight to about 99% by weight of cromolyn sodium and the inhalation device is a dry-powder inhaler.

The disclosure provides a dosage form comprising: (a) a pharmaceutical composition comprising from about 1% to about 99% by weight of cromolyn sodium; and (b) an inhalation device that forms an aerosol of the pharmaceutical composition, the aerosol exhibiting a respirable fraction of the pharmaceutical composition (≤5 μm) as measured by USP <1601> or USP <601> of at least about 60%. In certain embodiments, the aerosol exhibits an RF (≤3.3 μm) as measured by USP <1601> or USP <601> of at least about 30%. In certain embodiments, the aerosol exhibits an RF (≤3.3 μm) as measured by USP <1601> or USP <601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF (≤5 μm) as measured by USP <1601> or USP <601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%.

The disclosure provides a dosage form, comprising (a) a pharmaceutical composition comprising from about 1% by weight to about 99% by weight of cromolyn sodium; and (b) a means for administering the pharmaceutical composition to a subject having pulmonary fibrosis in the form of an aerosol, wherein said aerosol has a respirable fraction (≤3.3 μm) as measured by USP <1601> or USP <601> of at least about 30%.

The disclosure provides a dosage form, comprising (a) a pharmaceutical composition comprising from about 1% by weight to about 99% by weight of cromolyn sodium; and (b) a means for administering the pharmaceutical composition to a subject having pulmonary fibrosis in the form of an aerosol, wherein said aerosol has a respirable fraction (≤3.3 μm) as measured by USP <1601> or USP <601> of at least about 30% and a respirable fraction (≤5 μm) as measured by USP <1601> or USP <601> of at least about 75%.

The disclosure provides a dosage form, comprising (a) a pharmaceutical composition comprising from about 2% by weight to about 6% by weight of cromolyn sodium; and (b) a means for administering the pharmaceutical composition to a subject having pulmonary fibrosis in the form of an aerosol, wherein said aerosol has a respirable fraction (≤3.3 μm) as measured by USP <1601> of at least about 30%.

The disclosure provides a dosage form, comprising (a) a pharmaceutical composition comprising from about 2% by weight to about 6% by weight of cromolyn sodium; and (b) a means for administering the pharmaceutical composition to a subject having pulmonary fibrosis in the form of an aerosol, wherein said aerosol has a respirable fraction (≤3.3 μm) as measured by USP <1601> of at least about 30% and a respirable fraction (≤5 μm) as measured by USP <1601> of at least about 75%.

In certain embodiments, the disclosure provides any of the dosage forms disclosed herein, comprising from about 5 mg to about 80 mg of cromolyn sodium. In certain embodiments, the dosage forms disclosed herein comprise cromolyn or a pharmaceutically acceptable salt thereof at a dosage or nominal dosage of less than about 1 mg/dose, about 1 mg/dose to about 100 mg/dose, about 1 mg/dose to about 120 mg/dose, about 5 mg/dose to about 80 mg/dose, about 20 mg/dose to about 60 mg/dose, about 30 mg/dose to about 50 mg/dose, or greater than about 100 mg/dose. In certain embodiments, the dosage forms disclosed herein comprise cromolyn or a pharmaceutically acceptable salt thereof at a dosage or nominal dosage less than about 1 mg, about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In certain embodiments, the dosage forms disclosed herein comprise cromolyn or a pharmaceutically acceptable salt thereof at a dosage or nominal dosage of about 10 mg. In certain embodiments, the dosage forms disclosed herein comprise cromolyn or a pharmaceutically acceptable salt thereof at a dosage or nominal dosage of about 20 mg. In certain embodiments, the dosage forms disclosed herein comprise cromolyn or a pharmaceutically acceptable salt thereof at a dosage or nominal dosage of about 30 mg. In certain embodiments, the dosage forms disclosed herein comprise cromolyn or a pharmaceutically acceptable salt thereof at a dosage or nominal dosage of about 40 mg. In certain embodiments, the dosage forms disclosed herein comprise cromolyn or a pharmaceutically acceptable salt thereof at a dosage or nominal dosage of about 50 mg. In certain embodiments, the dosage forms disclosed herein comprise cromolyn or a pharmaceutically acceptable salt thereof at a dosage or nominal dosage of about 60 mg. In certain embodiments, the dosage forms disclosed herein comprise cromolyn or a pharmaceutically acceptable salt thereof at a dosage or nominal dosage of about 70 mg. In certain embodiments, the dosage forms disclosed herein comprise cromolyn or a pharmaceutically acceptable salt thereof at a dosage or nominal dosage of about 80 mg.

In certain embodiments, the disclosure provides any of the dosage forms disclosed herein, comprising: (a) a pharmaceutical composition comprising from about 2% to about 6% by weight of cromolyn sodium, and an osmolarity adjusting agent consisting of sodium chloride; and (b) an inhalation device that forms an aerosol of the pharmaceutical composition, the aerosol exhibiting a respirable fraction of the pharmaceutical composition (<5 μm) as measured by USP <1601> of at least about 60%. In certain embodiments, the aerosol exhibits an RF (≤3.3 μm) as measured by USP <1601> of at least about 30%. In certain embodiments, the aerosol exhibits an RF (≤3.3 μm) as measured by USP <1601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF (≤5 μm) as measured by USP <1601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%. In certain embodiments, the osmolality of the pharmaceutical composition is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the pharmaceutical composition is about 120 mOsm/kg, about 125 mOsm/kg, about 130 mOsm/kg, about 135 mOsm/kg, about 140 mOsm/kg, about 145 mOsm/kg, or about 150 mOsm/kg.

The disclosure provides a dosage form comprising: (a) a pharmaceutical composition comprising from about 2% to about 6% by weight of cromolyn sodium, and an osmolarity adjusting agent consisting of sodium chloride; and (b) a means for producing an aerosol of the pharmaceutical composition, the aerosol exhibiting a respirable fraction of the pharmaceutical composition (≤5 μm) as measured by USP <1601> of at least about 60%. In certain embodiments, the aerosol exhibits an RF (≤3.3 μm) as measured by USP <1601> of at least about 30%. In certain embodiments, the aerosol exhibits an RF (≤3.3 μm) as measured by USP <1601> of at least about 30%, at least about 35%, at least about 40%, at least about 45%, at least about 50%, at least about 55%, at least about 60%, at least about 65%, at least about 70%, at least about 75%, or at least about 80%. In certain embodiments, the aerosol exhibits and RF (≤5 μm) as measured by USP <1601> of at least about 30%, or at least about 35%, or at least about 40%, or at least about 45%, or at least about 50%, or at least about 55%, or at least about 60%, or at least about 65%, or at least about 75%, or at least about 80%, or at least about 85%, or at least about 90%, or at least about 95%. In certain embodiments, the osmolality of the pharmaceutical composition is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the pharmaceutical composition is about 120 mOsm/kg, about 125 mOsm/kg, about 130 mOsm/kg, about 135 mOsm/kg, about 140 mOsm/kg, about 145 mOsm/kg, or about 150 mOsm/kg.

The disclosure provides any of the dosage forms disclosed herein, wherein administration of the pharmaceutical composition to the subject produces in the subject an AUC(0-∞) of the cromolyn sodium greater than about 200 ng*hr/mL, and a Cmax of the cromolyn sodium greater than about 80 ng/mL. In certain embodiments, administration of the pharmaceutical composition to the subject produces in the subject an AUC(0-∞) of the cromolyn sodium greater than about 330 ng*hr/mL, and a Cmax of the cromolyn sodium greater than about 150 ng/mL. In certain embodiments, administration of the pharmaceutical composition to the subject produces in the subject an AUC(0-∞) of the cromolyn sodium greater than about 100 ng*hr/mL, and a Cmax of the cromolyn sodium greater than about 40 ng/mL. In certain embodiments, administration of the pharmaceutical composition comprising about 40 mg of cromolyn sodium to the subject produces in the subject an AUC(0-∞) of the cromolyn sodium that is between about 120 ng*hr/mL and about 500 ng*hr/mL. In certain embodiments, administration of the pharmaceutical composition comprising about 40 mg of cromolyn sodium to the subject produces in the subject an AUC(0-∞) of the cromolyn sodium that is within 80% to 125% of about 340 ng*hr/mL. In certain embodiments, administration of the pharmaceutical composition comprising about 40 mg of cromolyn sodium to the subject produces in the subject an AUC(0-6) of the cromolyn sodium that is between about 120 ng*hr/mL and about 350 ng*hr/mL. In certain embodiments, administration of the pharmaceutical composition comprising about 40 mg of cromolyn sodium to the subject produces in the subject an AUC(0-6) of the cromolyn sodium that is within 80% to 125% of about 237 ng*hr/mL. In certain embodiments, administration of the pharmaceutical composition comprising about 40 mg of cromolyn sodium to the subject produces in the subject a Cmax of the cromolyn sodium of between about 40 ng/mL and about 150 ng/mL. In certain embodiments, administration of the pharmaceutical composition comprising about 40 mg of cromolyn sodium to the subject produces in the subject a Cmax of the cromolyn sodium that is within 80% to 125% of about 75 ng/mL, or about 82 ng/mL, or about 85 ng/mL, or about 93 ng/mL. In certain embodiments, administration of the pharmaceutical composition comprising about 60 mg of cromolyn sodium to the subject produces in the subject an AUC(0-∞) of the cromolyn sodium that is between about 250 ng*hr/mL and about 1000 ng*hr/mL. In certain embodiments, administration of the pharmaceutical composition comprising about 60 mg of cromolyn sodium to the subject produces in the subject an AUC(0-∞) of the cromolyn sodium that is within 80% to 125% of about 542 ng*hr/mL. In certain embodiments, administration of the pharmaceutical composition comprising about 60 mg of cromolyn sodium to the subject produces in the subject an AUC(0-6) of the cromolyn sodium that is between about 200 ng*hr/mL and about 700 ng*hr/mL. In certain embodiments, administration of the pharmaceutical composition comprising about 60 mg of cromolyn sodium to the subject produces in the subject an AUC(0-6) of the cromolyn sodium that is within 80% to 125% of about 389 ng*hr/mL. In certain embodiments, administration of the pharmaceutical composition comprising about 60 mg of cromolyn sodium to the subject produces in the subject a Cmax of the cromolyn sodium of between about 50 ng/mL and about 250 ng/mL. In certain embodiments, administration of the pharmaceutical composition comprising about 60 mg of cromolyn sodium to the subject produces in the subject a Cmax of the cromolyn sodium that is within 80% to 125% of about 119 ng/mL, or about 148 ng/mL, or about 157 ng/mL. In certain embodiments, administration of the pharmaceutical composition comprising about 80 mg of cromolyn sodium to the subject produces in the subject an AUC(0-∞) of the cromolyn sodium that is between about 300 ng*hr/mL and about 800 ng*hr/mL. In certain embodiments, administration of the pharmaceutical composition comprising about 80 mg of cromolyn sodium to the subject produces in the subject an AUC(0-∞) of the cromolyn sodium that is within 80% to 125% of about 526 ng*hr/mL. In certain embodiments, administration of the pharmaceutical composition comprising about 80 mg of cromolyn sodium to the subject produces in the subject a Cmax of the cromolyn sodium of between about 90 ng/mL and about 450 ng/mL.

In certain embodiments, use of a nebulizer in the methods disclosed herein provides a RDDR of at least about 2 times, at least about 3 times or at least about 4 times the RDDR achievable with a conventional inhalation device. For example, where the cromolyn or a pharmaceutically-acceptable salt thereof is cromolyn sodium, in certain embodiments the RDDR is at least about 5 mg/min, at least about 10 mg/min, at least about 15 mg/min, at least about 20 mg/min, at least about 25 mg/min, at least about 30 mg/min, at least about 35 mg/min, at least about 40 mg/min, at least about 45 mg/min, at least about 50 mg/min, at least about 55 mg/min, or at least about 60 mg/min.

In certain embodiments, administration of cromolyn or a pharmaceutically-acceptable salt thereof with a nebulizer in the methods disclosed herein provides a GSD of emitted droplet size distribution of about 1.1 to about 2.1, about 1.2 to about 2.0, about 1.3 to about 1.9, less than about 2, at least about 1.4 to about 1.8, at least about 1.5 to about 1.7, about 1.4, about 1.5, about 1.6, or about 1.7. In certain embodiments, administration of cromolyn or a pharmaceutically-acceptable salt thereof with a nebulizer in the methods disclosed herein provides a MMAD of droplet size of about 1 µm to about 5 µm, about 2 to about 4 µm, about 3 to about 4 µm, about 3.5 to about 4.5 µm, or about 3.5 µm. In some particular embodiments, administration of cromolyn or a pharmaceutically-acceptable salt thereof in the methods disclosed herein provides droplets having a particular combination of MMAD and GSD, for example: an MMAD of less than about 5 µm and a GSD of about 1.1 to about 2.1; an MMAD of less than about 4.5 µm and a GSD of about 1.1 to about 2.1; an MMAD of about 1 µm to about 5 µm and a GSD of about 1.1 to about 2.1; an MMAD of about 1.5 to about 4.5 µm and a GSD of about 1.1 to about 2.1; an MMAD of less than about 5 µm and a GSD of about 1.1 to about 2.0; an MMAD of less than about 4.5 µm and a GSD of about 1.1 to about 2.0; an MMAD of about 1 µm to about 5 µm and a GSD of about 1.1 to about 2.0; an MMAD of about 1.5 to about 4.5 µm and a GSD of about 1.1 to about 2.0; an MMAD of less than about 5 µm and a GSD of about 1.1 to about 1.9; an MMAD of less than about 4.5 µm and a GSD of about 1.1 to about 1.9; an MMAD of about 1 µm to about 5 µm and a GSD of about 1.1 to about 1.9; an MMAD of about 1.5 to about 4.5 µm and a GSD of about 1.1 to about 1.9; an MMAD of less than about 5 µm and a GSD of about 1.1 to about 1.8; an MMAD of less than about 4.5 µm and a GSD of about 1.1 to about 1.8; an MMAD of about 1 µm to about 5 µm and a GSD of about 1.1 to about 1.8; an MMAD of about 1.5 to about 4.5 µm and a GSD of about 1.1 to about 1.8; an MMAD of about 3.5 µm or less and a GSD of about 1.7; an MMAD of about 4.1 µm or less and a GSD of about 1.7; an MMAD of about 3.5 µm and a GSD of about 1.7; or an MMAD of about 4.1 µm and a GSD of about 1.7.

In certain embodiments, the median particle size of cromolyn or a pharmaceutically-acceptable salt thereof aerosol administered with a nebulizer is between about 1 µm and about 6 µm, between about 2 µm and about 5 µm, between about 3 µm and about 5 between about 3 µm and about 4 µm, about 1 µm, about 2 µm, about 3 about 4 µm, about 5 µm, or about 6 µm. In certain embodiments, the median particle size of cromolyn sodium aerosol administered with a nebulizer is between about 1 µm and about 6 µm, between about 2 µm and about 5 between about 3 µm and about 5 µm, between about 3 µm and about 4 µm, about 1 µm, about 2 µm, about 3 µm, about 4 µm, about 5 µm, or about 6 µm.

Inhalation Formulations

In certain embodiments disclosed herein are provided formulations comprising from about 2% to about 10% by weight cromolyn sodium and an osmotic agent consisting of sodium chloride, wherein the formulation is stable when stored at 25° C. for at least 4 weeks, or at least 6 weeks, or at least 8 weeks, or at least 10 weeks, or at least 12 weeks, or at least 6 months, or at least 8 months, or at least 10 months, or at least 12 months, or at least 14 months, or at least 16 months, or at least 18 months, or at least 20 months, or at least 24 months. In certain embodiments, the formulations remain clear solutions when stored at 25° C. for these same time periods. In certain embodiments, the formulations exhibit less than 1% by weight total impurities when stored at 25° C. for these same time periods. In certain embodiments, the formulation comprises about 4% by weight of cromolyn sodium. In certain embodiments, the formulation comprises about 6% by weight of cromolyn sodium. In certain embodiments, the osmolality of the formulation is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the formulation is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments disclosed herein are provided formulations comprising from about 2% to about 10% by weight cromolyn sodium and an osmotic agent consisting of sodium chloride, wherein the formulation is stable when stored at 40° C. for at least 4 weeks, or at least 6 weeks, or at least 8 weeks, or at least 10 weeks, or at least 12 weeks, or at least 6 months, or at least 8 months, or at least 10 months, or at least 12 months, or at least 14 months, or at least 16 months, or at least 18 months, or at least 20 months, or at least 24 months. In certain embodiments, the formulations remain clear solutions when stored at 40° C. for these same time periods. In certain embodiments, the formulations exhibit less than 1% by weight total impurities when stored at 40° C. for these same time periods. In certain embodiments, the formulation comprises about 4% by weight of cromolyn sodium. In certain embodiments, the formulation comprises about 6% by weight of cromolyn sodium In certain embodiments, the osmolality of the formulation is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the formulation is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments of the methods disclosed herein, inhalation formulations are administered by an inhalation device, e.g., a nebulizer, a high-efficiency nebulizer or a dry-powder inhaler, to provide a systemically effective amount of cromolyn or a pharmaceutically-acceptable salt thereof for the treatment of a subject having pulmonary fibrosis, including IPF. In certain embodiments, the methods disclosed herein comprise administering a nominal dose of cromolyn or a pharmaceutically-acceptable salt thereof in an aqueous inhalation solution to the subject with an inhalation device, e.g., a nebulizer.

In certain embodiments of the methods disclosed herein, an inhalation formulation administered with an inhalation device, e.g., a nebulizer, a high-efficiency nebulizer or a dry-powder inhaler, produces in a subject an AUC(0-∞) of cromolyn or a pharmaceutically-acceptable salt thereof greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the subject.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof of about 100 ng*hr/mL, about 110 ng*hr/mL, about 120 ng*hr/ mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 100 ng*hr/mL, greater than about 110 ng*hr/mL, greater than about 120 ng*hr/mL, greater than about 130 ng*hr/mL, greater than about 140 ng*hr/mL, greater than about 150 ng*hr/mL, greater than about 160 ng*hr/mL, greater than about 170 ng*hr/mL, greater than about 180 ng*hr/mL, greater than about 190 ng*hr/mL, greater than about 200 ng*hr/mL, greater than about 225 ng*hr/mL, greater than about 250 ng*hr/mL, greater than about 275 ng*hr/mL, greater than about 300 ng*hr/mL, greater than about 325 ng*hr/mL, greater than about 350 ng*hr/mL, greater than about 375 ng*hr/mL, greater than about 400 ng*hr/mL, greater than about 425 ng*hr/mL, greater than about 450 ng*hr/mL, greater than about 475 ng*hr/mL, greater than about 500 ng*hr/mL, greater than about 525 ng*hr/mL, greater than about 550 ng*hr/mL, greater than about 575 ng*hr/mL, greater than about 600 ng*hr/mL, greater than about 625 ng*hr/mL, greater than about 650 ng*hr/mL, greater than about 675 ng*hr/mL, greater than about 700 ng*hr/mL, greater than about 725 ng*hr/mL, greater than about 750 ng*hr/mL, greater than about 775 ng*hr/mL, greater than about 800 ng*hr/mL, greater than about 825 ng*hr/mL, greater than about 850 ng*hr/mL, greater than about 875 ng*hr/mL, greater than about 900 ng*hr/mL, greater than about 925 ng*hr/mL, greater than about 950 ng*hr/mL, greater than about 975 ng*hr/mL, or greater than about 1000 ng*hr/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 100 ng*hr/mL, about 110 ng*hr/mL, about 120 ng*hr/mL, about 130 ng*hr/mL, about 140 ng*hr/mL, about 150 ng*hr/mL, about 160 ng*hr/mL, about 170 ng*hr/mL, about 180 ng*hr/mL, about 190 ng*hr/mL, about 200 ng*hr/mL, about 225 ng*hr/mL, about 250 ng*hr/mL, ng*hr/mL, about 275 ng*hr/mL, about 300 ng*hr/mL, about 325 ng*hr/mL, about 350 ng*hr/mL, about 375 ng*hr/mL, about 400 ng*hr/mL, about 425 ng*hr/mL, about 450 ng*hr/mL, about 475 ng*hr/mL, about 500 ng*hr/mL, about 525 ng*hr/mL, about 550 ng*hr/mL, about 575 ng*hr/mL, about 600 ng*hr/mL, about 625 ng*hr/mL, about 650 ng*hr/mL, about 675 ng*hr/mL, about 700 ng*hr/mL, about 725 ng*hr/mL, about 750 ng*hr/mL, about 775 ng*hr/mL, about 800 ng*hr/mL, about 825 ng*hr/mL, about 850 ng*hr/mL, about 875 ng*hr/mL, about 900 ng*hr/mL, about 925 ng*hr/mL, about 950 ng*hr/mL, about 975 ng*hr/mL, or about 1000 ng*hr/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject a Cmax of cromolyn or a pharmaceutically-acceptable salt thereof greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject a Cmax of cromolyn or a pharmaceutically-acceptable salt thereof greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject a Cmax of cromolyn or a pharmaceutically-acceptable salt thereof of about 50 mg/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, about 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject a Cmax of cromolyn or a pharmaceutically-acceptable salt thereof of about 50 mg/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, about 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject a Cmax of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject a Cmax of cromolyn sodium greater than about 40 ng/mL, greater than about 50 ng/mL, greater than about 60 ng/mL, greater than about 70 ng/mL, greater than about 80 ng/mL, greater than about 90 ng/mL, greater than about 100 ng/mL, greater than about 110 ng/mL, greater than about 120 ng/mL, greater than about 130 ng/mL, greater than about 140 ng/mL, greater than about 150 ng/mL, greater than about 160 ng/mL, greater than about 170 ng/mL, greater than about 180 ng/mL, greater than about 190 ng/mL, greater than about 200 ng/mL, greater than about 210 ng/mL, greater than about 220 ng/mL, greater than about 230 ng/mL, greater than about 240 ng/mL, greater than about 250 ng/mL, greater than about 260 ng/mL, greater than about 270 ng/mL, greater than about 280 ng/mL, greater than about 290 ng/mL, greater than about 300 ng/mL, greater than about 310 ng/mL, greater than about 320 ng/mL, greater than about 330 ng/mL, greater than about 340 ng/mL, greater than about 350 ng/mL, greater than about 360 ng/mL, greater than about 370 ng/mL, greater than about 380 ng/mL, greater than about 390 ng/mL, or greater than about 400 ng/mL after administration of the formulation to the subject or subject.

In certain embodiments of the methods disclosed herein, an inhalation formulation administered with an inhalation device, e.g., a nebulizer, a high-efficiency nebulizer or a dry-powder inhaler, produces in a subject a Cmax of cromolyn sodium of about 50 mg/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, about 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject. In certain embodiments of the methods disclosed herein, an inhalation formulation administered with an inhalation device, e.g., a nebulizer, a high-efficiency nebulizer or a dry-powder inhaler, produces in a subject a Cmax of cromolyn sodium of about 50 mg/mL, about 60 ng/mL, about 70 ng/mL, about 80 ng/mL, about 90 ng/mL, about 100 ng/mL, about 110 ng/mL, about 120 ng/mL, about 130 ng/mL, about 140 ng/mL, about 150 ng/mL, about 160 ng/mL, about 170 ng/mL, about 180 ng/mL, about 190 ng/mL, about 200 ng/mL, about 210 ng/mL, about 220 ng/mL, about 230 ng/mL, about 240 ng/mL, about 250 ng/mL, about 260 ng/mL, about 270 ng/mL, about 280 ng/mL, about 290 ng/mL, about 300 ng/mL, about 310 ng/mL, about 320 ng/mL, about 330 ng/mL, about 340 ng/mL, about 350 ng/mL, about 360 ng/mL, about 370 ng/mL, about 380 ng/mL, about 390 ng/mL, or about 400 ng/mL after administration of the formulation to the subject.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 120 ng*hr/mL and/or an average Cmax of the cromolyn or a pharmaceutically-acceptable salt thereof greater than about 55 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 120 ng*hr/mL and/or a Cmax of the cromolyn or a pharmaceutically-acceptable salt thereof greater than about 55 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 200 ng*hr/mL and an average Cmax of the cromolyn or a pharmaceutically-acceptable salt thereof greater than about 80 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 200 ng*hr/mL and a Cmax of the cromolyn or a pharmaceutically-acceptable salt thereof greater than about 80 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 330 ng*hr/mL and an average Cmax of the cromolyn or a pharmaceutically-acceptable salt thereof greater than about 150 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 330 ng*hr/mL and a Cmax of the cromolyn or a pharmaceutically-acceptable salt thereof greater than about 150 ng/mL.

In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 525 ng*hr/mL and an average Cmax of the cromolyn or a pharmaceutically-acceptable salt thereof greater than about 230 ng/mL. In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn or a pharmaceutically-acceptable salt thereof greater than about 525 ng*hr/mL and a Cmax of the cromolyn or a pharmaceutically-acceptable salt thereof greater than about 230 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 120 ng*hr/mL and/or an average Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 120 ng*hr/mL and/or a Cmax of cromolyn sodium greater than about 55 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 120 ng*hr/mL and an average Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 120 ng*hr/mL and a Cmax of cromolyn sodium greater than about 55 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 200 ng*hr/mL and an average Cmax of cromolyn sodium greater than about 80 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 200 ng*hr/mL and a $C_{max}$ of cromolyn sodium greater than about 80 ng/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 330 ng*hr/mL and an average Cmax of cromolyn sodium greater than about 150 ng/mL. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 330 ng*hr/mL and a Cmax of cromolyn sodium greater than about 150 ng/mL.

In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 525 ng*hr/mL and an average Cmax of cromolyn sodium greater than about 230 ng/mL. In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium greater than about 525 ng*hr/mL and a Cmax of cromolyn sodium greater than about 230 ng/mL.

In certain embodiments of the methods disclosed herein, the administration of a formulation comprising about 40 mg of cromolyn sodium, or a pharmaceutically acceptable salt thereof, to a subject by means of an inhalation device affords a Cmax or average Cmax of cromolyn sodium in the subject of from about from 30 ng/mL to about 120 ng/mL, or from about 40 ng/mL to about 120 ng/mL, or from about 40 ng/mL to about 110 ng/mL. In certain embodiments, the administration of a formulation comprising about 40 mg of cromolyn sodium, or a pharmaceutically acceptable salt thereof, to a subject by means of an inhalation device affords an $AUC_{(0-\infty)}$ of cromolyn sodium in the subject of between about 100 ng*hr/mL and about 350 ng*hr/mL, or between about 100 ng*hr/mL and about 325 ng*hr/mL, or between about 115 ng*hr/mL and about 325 ng*hr/mL, or between about 120 ng*hr/mL and about 320 ng*hr/mL, or between about 125 ng*hr/mL and about 300 ng*hr/mL. In certain embodiments, the formulation comprises between 1% and 10% by weight cromolyn sodium, or between about 4% by weight and 6% by weight cromolyn sodium. In certain embodiments, the formulation comprises 4% by weight cromolyn sodium. In certain embodiments, the formulation comprises 6% by weight cromolyn sodium. In certain embodiments, use of a nebulizer to administer the formulation provides an aerosol of the formulation comprising cromolyn or a pharmaceutically-acceptable salt thereof, wherein the aerosol exhibits an RF (≤5 µm) of an cromolyn or a pharmaceutically-acceptable salt thereof of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, or about 75%. In certain embodiments, use of a nebulizer in the methods disclosed herein provides an aerosol of a solution comprising cromolyn or a pharmaceutically-acceptable salt thereof, wherein the aerosol exhibits an RF (≤5 µm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, about 65% to about 75%, about 65% to about 80%, about 60% to about 80%, about 66%, or about 75%. In certain embodiments, the formulation comprises an osmotic agent comprising sodium chloride. In certain embodiments, the formulation comprises an osmotic agent consisting of sodium chloride. In certain embodiments, the osmolality of the formulation is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the formulation is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments of the methods disclosed herein, the administration of a formulation comprising about 60 mg of cromolyn sodium, or a pharmaceutically acceptable salt thereof, to a subject by means of an inhalation device affords a Cmax or average Cmax of cromolyn sodium in the subject of from about from 50 ng/mL to about 175 ng/mL, or from about 60 ng/mL to about 175 ng/mL, or from about 60 ng/mL to about 170 ng/mL, or from about 60 ng/mL to about 165 ng/mL, or from about 70 ng/mL to about 165 ng/mL. In certain embodiments, the administration of a formulation comprising about 60 mg of cromolyn sodium, or a pharmaceutically acceptable salt thereof, to a subject by means of an inhalation device affords an $AUC(0-\infty)$ of cromolyn sodium in the subject of between about 200 ng*hr/mL and about 600 ng*hr/mL, or between about 200 ng*hr/mL and about 575 ng*hr/mL, or between about 200 ng*hr/mL and about 550 ng*hr/mL, or between about 200 ng*hr/mL and about 525 ng*hr/mL, or between about 210 ng*hr/mL and about 525 ng*hr/mL, or between about 215 ng*hr/mL and about 515 ng*hr/mL, or between about 175 ng*hr/mL and about 500 ng*hr/mL, or between about 195 ng*hr/mL and about 515 ng*hr/mL, or between about 200 ng*hr/mL and about 500 ng*hr/mL. In certain embodiments, the formulation comprises between 1% and 10% by weight cromolyn sodium, or between about 4% by weight and 6% by weight cromolyn sodium. In certain embodiments, the formulation comprises 4% by weight cromolyn sodium. In certain embodiments, the formulation comprises 6% by weight cromolyn sodium. In certain embodiments, use of a nebulizer to administer the formulation provides an aerosol of the formulation comprising cromolyn or a pharmaceutically-acceptable salt thereof, wherein the aerosol exhibits an RF (≤5 µm) of an cromolyn or a pharmaceutically-acceptable salt thereof of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, or about 75%. In certain embodiments, use of a nebulizer in the methods disclosed herein provides an aerosol of a solution comprising cromolyn or a pharmaceutically-acceptable salt thereof, wherein the aerosol exhibits an RF (≤5 µm) of cromolyn sodium of at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, about 20% to about 95%, about 35% to about 90%, or about 40% to about 80%, about 40% to about 90%, about 40% to about 95%, about 45% to about 90%, about 45% to about 95%, about 50% to about 90%, about 65% to about 90%, about 60% to about 95%, about 65% to about 95%, about 70% to about 90%, about 55% to about 90%, about 70% to about 80%, about 65% to about 75%, about 65% to about 80%, about 60% to about 80%, about 66%, or about 75%. In certain embodiments, the formulation comprises an osmotic agent comprising sodium chloride. In certain embodiments, the formulation comprises an osmotic agent consisting of sodium chloride. In certain embodiments, the osmolality of the formulation is between about 100 mOsm/kg and about 175 mOsm/kg, or between about 100 mOsm/kg and about 170 mOsm/kg, or between about 100 mOsm/kg and about 165 mOsm/kg, or between about 100 mOsm/kg and about 160 mOsm/kg, or between about 100 mOsm/kg and about 150 mOsm/kg, or between about 110 mOsm/kg and about 150 mOsm/kg, or between about 110 mOsm/kg and about 140 mOsm/kg, or between about 115 mOsm/kg and about 140 mOsm/kg, or between about 120 mOsm/kg and about 140 mOsm/kg, or between about 120 mOsm/kg and about 130 mOsm/kg. In certain embodiments, the osmolality of the formulation is about 120 mOsm/kg, about 125 mOsm/kg, about 130 mOsm/kg, about 135 mOsm/kg, about 140 mOsm/kg, about 145 mOsm/kg, or about 150 mOsm/kg.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 330 ng*hr/mL and an average Cmax of cromolyn sodium of about 150 ng/mL when a nominal dose of 40 mg of cromolyn sodium is administered with the inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 330 ng*hr/mL and a Cmax of cromolyn sodium of about 150 ng/mL when a nominal dose of 40 mg of cromolyn sodium is administered with the inhalation device.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 525 ng*hr/mL and an average Cmax of cromolyn sodium of about 230 ng/mL when a nominal dose of 80 mg of cromolyn sodium is administered with the inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 525 ng*hr/mL and a Cmax of cromolyn sodium of about 230 ng/mL when a nominal dose of 80 mg of cromolyn sodium is administered with the inhalation device.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 180 ng*hr/mL to about 220 ng*hr/mL and an average Cmax of cromolyn sodium of about 70 ng/mL to about 90 ng/mL when a nominal dose of 40 mg of cromolyn sodium is administered with the inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 180 ng*hr/mL to about 220 ng*hr/mL and a Cmax of cromolyn sodium of about 70 ng/mL to about 90 ng/mL when a nominal dose of 40 mg of cromolyn sodium is administered with the inhalation device.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 300 ng*hr/mL to about 360 ng*hr/mL and an average Cmax of cromolyn sodium of about 135 ng/mL to about 165 ng/mL when a nominal dose of 40 mg of cromolyn sodium is administered with the inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 300 ng*hr/mL to about 360 ng*hr/mL and a Cmax of cromolyn sodium of about 135 ng/mL to about 165 ng/mL when a nominal dose of 40 mg of cromolyn sodium is administered with the inhalation device.

In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 475 ng*hr/mL to about 575 ng*hr/mL and an average Cmax of cromolyn sodium of about 200 ng/mL to about 260 ng/mL when a nominal dose of 80 mg of cromolyn sodium is administered with the inhalation device. In certain embodiments, of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 475 ng*hr/mL to about 575 ng*hr/mL and a Cmax of cromolyn sodium of about 200 ng/mL to about 260 ng/mL when a nominal dose of 80 mg of cromolyn sodium is administered with the inhalation device.

In certain embodiments of the methods disclosed herein, an inhalation formulation administered with an inhalation device, e.g., a nebulizer, a high-efficiency nebulizer or a dry-powder inhaler, provides a lung deposition (deposited lung dose) comprising cromolyn or pharmaceutically acceptable salt thereof of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25% to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the cromolyn or a pharmaceutically-acceptable salt thereof. In certain embodiments of the methods disclosed herein, an inhalation formulation administered with an inhalation device, e.g., a nebulizer, a high-efficiency nebulizer or a dry-powder inhaler, provides cromolyn sodium deposition (deposited lung dose) of at least about 15%, at least about 20%, at least about 25%, at least about 30%, at least about 35%, at least about 40%, at least about 45%, at least about 50%, at least about 55%, at least about 60%, about 20% to about 40%, about 25% to about 35%, about 25% to about 30%, about 25% to about 75%, about 30% to about 50%, about 35% to about 90%, about 40% to about 80%, about 40% to about 60%, about 50% to about 60%, about 50% to about 70%, or about 60% to about 75% based on the nominal dose of the cromolyn sodium.

In certain embodiments of the methods disclosed herein, an inhalation formulation administered with an inhalation device, e.g., a nebulizer, a high-efficiency nebulizer or a dry-powder inhaler, provides a lung deposition (deposited lung dose) comprising cromolyn or a pharmaceutically-acceptable salt thereof of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the cromolyn or a pharmaceutically-acceptable salt thereof. In certain embodiments of the methods disclosed herein, an inhalation formulation administered with an inhalation device, e.g., a nebulizer, a high-efficiency nebulizer or a dry-powder inhaler, provides cromolyn sodium lung deposition (deposited lung dose) of about 15%, about 20%, about 25%, about 30%, about 35%, about 40%, about 45%, about 50%, about 55%, about 60%, about 65%, about 70%, about 75% about 80%, about 85%, about 90%, about 95%, or about 100% based on the nominal dose of the cromolyn sodium.

In certain embodiments of the methods disclosed herein, an inhalation formulation administered with an inhalation device, e.g., a nebulizer, a high-efficiency nebulizer or a dry-powder inhaler, provides a lung deposition (deposited lung dose) comprising cromolyn or a pharmaceutically-acceptable salt thereof of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In certain embodiments of the methods disclosed herein, an inhalation formulation administered with an inhalation device, e.g., a nebulizer, a high-efficiency nebulizer or a dry-powder inhaler, provides a lung deposition (deposited lung dose) comprising cromolyn or a pharmaceutically-acceptable salt thereof of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In certain embodiments of the methods disclosed herein, an inhalation formulation administered with an inhalation device, e.g., a nebulizer, a high-efficiency nebulizer or a dry-powder inhaler, provides cromolyn sodium lung deposition (deposited lung dose) of greater than about 0.5 mg, greater than about 1 mg, greater than about 1.5 mg, greater than about 2 mg, greater than about 2.5 mg, greater than about 3 mg, greater than about 3.5 mg, greater than about 4 mg, greater than about 5 mg, greater than about 6 mg, greater than about 7 mg, greater than about 8 mg, greater than about 9 mg, greater than about 10 mg, greater than about 11 mg, greater than about 12 mg, greater than about 13 mg, greater than about 14 mg, or greater than about 15 mg. In certain embodiments of the methods disclosed herein, an inhalation formulation administered with an inhalation device, e.g., a nebulizer, a high-efficiency nebulizer or a dry-powder inhaler, provides cromolyn sodium lung deposition (deposited lung dose) of about 0.5 mg, about 1.0 mg, about 1.5 mg, about 2.0 mg, about 2.5 mg, about 3.0 mg, about 3.5 mg, about 4.0 mg, about 5.0 mg, about 6.0 mg, about 7.0 mg, about 8.0 mg, about 9.0 mg, about 10 mg, about 11 mg, about 12 mg, about 13 mg, about 14 mg, or about 15 mg.

In certain embodiments of the methods disclosed herein, an inhalation formulation containing cromolyn or a pharmaceutically-acceptable salt thereof is administered with an inhalation device, e.g., a nebulizer, a high-efficiency nebulizer or a dry-powder inhaler, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In certain embodiments of the methods disclosed herein, an inhalation formulation containing cromolyn sodium is administered with an inhalation device, e.g., a nebulizer, a high-efficiency nebulizer or a dry-powder inhaler, at an administration of less than about 1 mg/dose, about 1 mg/dose to about 100 mg/dose, about 5 mg/dose to about 80 mg/dose, about 20 mg/dose to about 60 mg/dose, about 30 mg/dose to about 50 mg/dose, or greater than 100 mg/dose. In certain embodiments of the methods disclosed herein, cromolyn or a pharmaceutically-acceptable salt thereof is administered in an inhalation formulation with an inhalation device, e.g., a nebulizer, a high-efficiency nebulizer or a dry-powder inhaler, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses. In certain embodiments of the methods disclosed herein, cromolyn sodium is administered in an inhalation formulation with an inhalation device, e.g., a nebulizer, a high-efficiency nebulizer or a dry-powder inhaler, in about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg doses, about 135 mg, about 140 mg, about 145 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg doses.

In certain embodiments of the methods disclosed herein, an inhalation formulation administered with an inhalation device, e.g., a nebulizer, a high-efficiency nebulizer or a dry-powder inhaler provides a bioavailability of cromolyn or a pharmaceutically-acceptable salt thereof of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45%, greater than about 50%, greater than about 55%, or greater than about 60% of the nominal dose. In certain embodiments, an inhalation formulation administered with an inhalation device, e.g., a nebulizer, a high-efficiency nebulizer or a dry-powder inhaler, in the methods disclosed herein provides a bioavailability of cromolyn or a pharmaceutically-acceptable salt thereof of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, or about 60% of the nominal dose.

In certain embodiments of the methods disclosed herein, an inhalation formulation administered with an inhalation device, e.g., a nebulizer, a high-efficiency nebulizer or a dry-powder inhaler provides a bioavailability of cromolyn sodium of greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 16%, greater than about 17%, greater than about 18%, greater than about 19%, greater than about 20%, greater than about 25%, greater than about 30%, greater than about 35%, greater than about 40%, greater than about 45% or greater than about 50% of the nominal dose. In certain embodiments, an aqueous inhalation formulation administered with an inhalation device, e.g., a nebulizer, a high-efficiency nebulizer or a dry-powder inhaler, in the methods disclosed herein provides a bioavailability of cromolyn sodium of about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, or about 50% of the nominal dose.

In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 120 ng*hr/mL and/or an average Cmax of the cromolyn or a pharmaceutically-acceptable salt thereof greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 120 ng*hr/mL and/or a Cmax of the cromolyn or a pharmaceutically-acceptable salt thereof greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 120 ng*hr/mL and an average Cmax of the cromolyn or a pharmaceutically-acceptable salt thereof greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 120 ng*hr/mL and a Cmax of the cromolyn or a pharmaceutically-acceptable salt thereof greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 200 ng*hr/mL and an average Cmax of the cromolyn or a pharmaceutically-acceptable salt thereof greater than about 80 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 200 ng*hr/mL and a Cmax of the cromolyn or a pharmaceutically-acceptable salt thereof greater than about 80 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 330 ng*hr/mL and an average Cmax of the cromolyn or a pharmaceutically-acceptable salt thereof greater than about 150 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 330 ng*hr/mL and a Cmax of the cromolyn or a pharmaceutically-acceptable salt thereof greater than about 150 ng/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 525 ng*hr/mL and an average Cmax of the cromolyn or a pharmaceutically-acceptable salt thereof greater than about 230 ng/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of the cromolyn or a pharmaceutically-acceptable salt thereof greater than about 525 ng*hr/mL and a Cmax of the cromolyn or a pharmaceutically-acceptable salt thereof greater than about 230 ng/mL.

In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL and/or an average Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL and/or a Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL and an average Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL and a Cmax of cromolyn sodium greater than about 55 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL and an average Cmax of cromolyn sodium greater than about 80 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL and a Cmax of cromolyn sodium greater than about 80 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL and an average Cmax of cromolyn sodium greater than about 150 ng/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL and a Cmax of cromolyn sodium greater than about 150 ng/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL and an average Cmax of cromolyn sodium greater than about 230 ng/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL and a Cmax of cromolyn sodium greater than about 230 ng/mL.

In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 120 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 120 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 200 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 200 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 330 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 330 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 525 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn or a pharmaceutically-acceptable salt thereof greater than about 5% and produces in a subject an $AUC_{(0-\infty)}$ of cromolyn or a pharmaceutically-acceptable salt thereof greater than about 525 ng*hr/mL.

In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 120 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL. In certain embodiments of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL. In certain embodiments, of the methods disclosed herein, an inhalation formulation administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL.

In certain embodiments of the methods disclosed herein, an inhalation formulation comprising 40 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL. In certain embodiments of the methods disclosed herein, an inhalation formulation comprising 40 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 200 ng*hr/mL. In certain embodiments of the methods disclosed herein, an inhalation formulation comprising 40 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL. In certain embodiments of the methods disclosed herein, an inhalation formulation comprising 40 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 330 ng*hr/mL. In certain embodiments, of the methods disclosed herein, an inhalation formulation comprising 80 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL. In certain embodiments, of the methods disclosed herein, an inhalation formulation comprising 80 mg cromolyn sodium administered with an inhalation device, e.g., a nebulizer, a high-efficiency nebulizer or a dry-powder inhaler, provides a bioavailability of cromolyn sodium greater than about 5% and produces in a subject an $AUC_{(0-\infty)}$ of cromolyn sodium greater than about 525 ng*hr/mL.

In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn or a pharmaceutically-acceptable salt thereof greater than about 120 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn or a pharmaceutically-acceptable salt thereof greater than about 120 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn or a pharmaceutically-acceptable salt thereof greater than about 200 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn or a pharmaceutically-acceptable salt thereof greater than about 200 ng*hr/mL. In certain embodiments of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn or a pharmaceutically-acceptable salt thereof greater than about 330 ng*hr/mL. In certain embodiments of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn or a pharmaceutically-acceptable salt thereof greater than about 330 ng*hr/mL. In certain embodiments, of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn or a pharmaceutically-acceptable salt thereof greater than about 525 ng*hr/mL. In certain embodiments of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn or a pharmaceutically-acceptable salt thereof greater than about 525 ng*hr/mL.

In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn sodium greater than about 120 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn sodium greater than about 120 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn sodium greater than about 200 ng*hr/mL. In certain embodiments of the methods disclosed herein, an inhalation formulation administered with an inhalation device, e.g., a nebulizer, has an RF (≤3.3 μm) of at least about 30% and produces in a subject an $AUC_{(0-\infty)}$ of cromolyn sodium greater than about 200 ng*hr/mL. In certain embodiments of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn sodium greater than about 330 ng*hr/mL. In certain embodiments of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn sodium greater than about 330 ng*hr/mL. In certain embodiments, of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn sodium greater than about 525 ng*hr/mL. In certain embodiments, of the methods disclosed herein, an inhalation formulation administered with an inhalation device, e.g., a nebulizer, has an RF (≤3.3 μm) of at least about 40% and produces in a subject an $AUC_{(0-\infty)}$ of cromolyn sodium greater than about 525 ng*hr/mL.

In certain embodiments of the methods disclosed herein, an inhalation formulation comprising 40 mg cromolyn sodium administered with an inhalation device, e.g., a nebulizer, has an RF (≤3.3 μm) of at least about 30% and produces in a subject an $AUC_{(0-\infty)}$ of cromolyn sodium greater than about 200 ng*hr/mL. In certain embodiments of the methods disclosed herein, an inhalation formulation comprising 40 mg cromolyn sodium administered with an inhalation device, e.g., a nebulizer, has an RF (≤3.3 μm) of at least about 30% and produces in a subject an $AUC_{(0-\infty)}$ of cromolyn sodium greater than about 200 ng*hr/mL. In certain embodiments of the methods disclosed herein, an inhalation formulation comprising 40 mg cromolyn sodium administered with an inhalation device, e.g., a nebulizer, has an RF (≤3.3 μm) of at least about 40% and produces in a subject an $AUC_{(0-\infty)}$ of cromolyn sodium greater than about 330 ng*hr/mL. In certain embodiments of the methods disclosed herein, an inhalation formulation comprising 40 mg cromolyn sodium administered with an inhalation device, e.g., a nebulizer, has an RF (≤3.3 μm) of at least about 40% and produces in a subject an $AUC_{(0-\infty)}$ of cromolyn sodium greater than about 330 ng*hr/mL. In certain embodiments of the methods disclosed herein, an inhalation formulation comprising 80 mg cromolyn sodium administered with an inhalation device, e.g., a nebulizer, has an RF (≤3.3 μm) of at least about 40% and produces in a subject an $AUC_{(0-\infty)}$ of cromolyn sodium greater than about 525 ng*hr/mL. In certain embodiments of the methods disclosed herein, an inhalation formulation comprising 80 mg cromolyn sodium administered with an inhalation device, e.g., a nebulizer, has an RF (≤3.3 μm) of at least about 40% and produces in a subject an $AUC_{(0-\infty)}$ of cromolyn sodium greater than about 525 ng*hr/mL.

In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 8.5 ng*hr/mL per mg of cromolyn sodium, and an average Cmax of cromolyn sodium of about 3.9 ng/mL per mg of cromolyn sodium when a nominal dose of 40 mg cromolyn sodium is administered to the subject with an inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 8.5 ng*hr/mL per mg of cromolyn sodium, and an average Cmax of cromolyn sodium of about 1.9 ng/mL per mg of cromolyn sodium when a nominal dose of 40 mg cromolyn sodium is administered to the subject with an inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 9 ng*hr/mL and a Cmax of cromolyn sodium of about 2.6 ng/mL per mg of cromolyn sodium when a nominal dose of 60 mg of cromolyn sodium administered to the subject with the inhalation device. In certain embodiments of the methods disclosed herein, an inhalation formulation administered with an inhalation device, e.g., a nebulizer, a high-efficiency nebulizer or a dry-powder inhaler, produces in a subject an $AUC_{(0-\infty)}$ of cromolyn sodium of about 6.6 ng*hr/mL and an average Cmax of cromolyn sodium of about 2.95 ng/mL per mg of cromolyn sodium when a nominal dose of 80 mg of cromolyn sodium is administered to the subject with the inhalation device.

In certain embodiments of the methods disclosed herein, an inhalation formulation containing cromolyn or a pharmaceutically-acceptable salt thereof such as cromolyn sodium is administered with an inhalation device, e.g., a nebulizer, at a fill volume of less than about 0.25 mL, less than about 0.5 mL, at least about 0.5 mL to about 1.5 mL, at least about 0.5 mL to about 1.8 mL, at least about 1.5 mL, or at least about 2.0 mL. In certain embodiments, an inhalation formulation is administered with an inhalation device, e.g., a nebulizer, at a fill volume about 0.1 mL to about 5.0 mL, about 0.25 mL to about 2.0 mL, about 0.5 mL to about 1.8 mL, about 0.5 mL to about 2 mL, about 0.5 mL to about 1.5 mL, about 0.5 mL to about 1.0 mL, about 0.5 mL or less, about 1 mL or less, about 1.5 mL or less, about 2.0 mL or less, about 2.5 mL or less, about 3.0 mL or less, about 3.5 mL or less, about 4.0 mL or less, about 4.5 mL or less, or about 5.0 mL or less. In certain embodiments, an inhalation formulation is administered with an inhalation device, e.g., a nebulizer, at a fill volume of about 0.5 mL, about 1.0 mL, about 1.5 mL, about 1.8 mL, about 2.0 mL, about 2.5 mL, about 3.0 mL, about 3.5 mL, about 4.0 mL, about 4.5 mL, or about 5.0 mL. In certain embodiments, an inhalation formulation is administered with an inhalation device, e.g., a nebulizer, which provides for a residual volume of cromolyn or a pharmaceutically-acceptable salt thereof after administration of the cromolyn or a pharmaceutically-acceptable salt thereof of less than about 10%, less than about 5%, or less than about 3% of the nominal dose. In certain embodiments of the methods disclosed herein, an inhalation formulation containing cromolyn or a pharmaceutically-acceptable salt thereof is administered with an inhalation device, e.g., a nebulizer, wherein the concentration of the cromolyn or a pharmaceutically-acceptable salt thereof is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight. In certain embodiments of the methods disclosed herein, an inhalation formulation containing cromolyn or a pharmaceutically-acceptable salt thereof is administered with an inhalation device, e.g., a nebulizer, wherein the concentration of the cromolyn or a pharmaceutically-acceptable salt thereof is from about 1% by weight to about 10% by weight, from about 2% by weight to about 8% by weight, from about 2% by weight to about 6% by weight, or from about 3% by weight to about 5% by weight. In certain embodiments of the methods disclosed herein, an inhalation formulation containing cromolyn or a pharmaceutically-acceptable salt thereof is administered with an inhalation device, e.g., a nebulizer, wherein the concentration of the cromolyn or a pharmaceutically-acceptable salt thereof is about 1% by weight, about 2% by weight, about 3% by weight, about 4% by weight, about 5% by weight, about 6% by weight, about 7% by weight, about 8% by weight, about 9% by weight, or about 10% by weight.

In certain embodiments of the methods disclosed herein, an inhalation formulation containing cromolyn sodium is administered with an inhalation device, e.g., a nebulizer, wherein the concentration of the cromolyn sodium is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight. In certain embodiments of the methods disclosed herein, an inhalation formulation containing cromolyn sodium is administered with an inhalation device, e.g., a nebulizer, wherein the concentration of the cromolyn sodium is from about 1% by weight to about 10% by weight, from about 2% by weight to about 8% by weight, from about 2% by weight to about 6% by weight, or from about 3% by weight to about 5% by weight. In certain embodiments of the methods disclosed herein, an inhalation formulation containing cromolyn sodium is administered with an inhalation device, e.g., a nebulizer, wherein the concentration of the cromolyn sodium is about 1% by weight, about 2% by weight, about 3% by weight, about 4% by weight, about 5% by weight, about 6% by weight, about 7% by weight, about 8% by weight, about 9% by weight, or about 10% by weight.

In certain embodiments of the methods disclosed herein, an inhalation formulation containing cromolyn sodium is administered with an inhalation device, e.g., dry-powder inhaler, wherein the concentration of the cromolyn sodium is greater than about 1% by weight, greater than about 2% by weight, greater than about 3% by weight, greater than about 4% by weight, greater than about 5% by weight, greater than about 6% by weight, greater than about 7% by weight, greater than about 8% by weight, greater than about 9% by weight, or greater than about 10% by weight, greater than about 20% by weight, greater than about 30% by weight, greater than about 40% by weight, greater than about 50% by weight, greater than about 60% by weight, greater than about 70% by weight, greater than about 80% by weight, or greater than about 90% by weight. In certain embodiments of the methods disclosed herein, an inhalation formulation containing cromolyn sodium is administered with an inhalation device, e.g., dry-powder inhaler, wherein the concentration of the cromolyn sodium is from about 1% by weight to about 99% by weight, from about 2% by weight to about 99% by weight, from about 2% by weight to about 80% by weight, from about 3% by weight to about 80% by weight, from about 5% by weight to about 80% by weight, from about 10% by weight to about 80% by weight, from about 20% by weight to about 90% by weight, from about 20% by weight to about 80% by weight, from about 30% by weight to about 99% by weight, from about 40% by weight to about 99% by weight, from about 50% by weight to about 99% by weight, from about 60% by weight to about 99% by weight, from about 70% by weight to about 99% by weight, from about 80% by weight to about 99% by weight, from about 1% by weight to about 50% by weight, from about 10% by weight to about 50% by weight, about 10% by weight to about 40% by weight, from about 10% by weight to about 30% by weight, from about 5% by weight to about 25% by weight, from about 5% by weight to about 20% by weight, from about 20% by weight to about 75% by weight, from about 25% by weight to about 75% by weight, or from about 25% by weight to about 50% by weight. In certain embodiments of the methods disclosed herein, an inhalation formulation containing cromolyn sodium is administered with an inhalation device, e.g., a dry-powder inhaler, wherein the concentration of the cromolyn sodium is about 1% by weight, about 2% by weight, about 3% by weight, about 4% by weight, about 5% by weight, about 6% by weight, about 7% by weight, about 8% by weight, about 9% by weight, about 10% by weight, about 20% by weight, about 25% by weight, about 30% by weight, about 40% by weight, about 50% by weight, about 60% by weight, about 70% by weight, about 75% by weight, about 80% by weight, about 90% by weight, about 95% by weight, or about 99% by weight.

In certain embodiments, an inhalation formulation containing cromolyn or a pharmaceutically-acceptable salt thereof is administered with an inhalation device, e.g., a nebulizer, a high-efficiency nebulizer or a dry-powder inhaler, in about 0.25 to about 10 minutes, about 0.50 to about 8 minutes, less than about 8 minutes, less than about 7 minutes, less than about 6 minutes, less than about 5 minutes, less than about 4 minutes, less than about 3 minutes, less than about 2 minutes, less than about 1.8 minutes, less than about 1.5 minutes, or less than 1 minute. In certain embodiments, the inhalation formulation is administered in about 3 minutes or less. In certain embodiments, the inhalation formulation is administered in about 1 minute, about 2 minutes, about 3 minutes, about 4 minutes, about 5 minutes, about 6 minutes, about 7 minutes, about 8 minutes, about 9 minutes, or about 10 minutes.

In certain embodiments of the methods disclosed herein, administration of cromolyn or a pharmaceutically-acceptable salt thereof with a nebulizer provides at least about a 1.5-fold, at least about a 1.8-fold, at least about a two-fold, at least about a three-fold, at least about a four-fold, or at least about a five-fold increase in one or more of AUClast, $AUC_{(0-\infty)}$, or $C_{max}$ as compared to the same or lower nominal dose of the cromolyn or a pharmaceutically-acceptable salt thereof administered with a conventional inhalation device or an oral formulation, e.g., a liquid oral formulation, tablet, or capsule.

In certain embodiments of the methods disclosed herein, inhalation formulations administered with a nebulizer are substantially free of a preservative, such as benzyl alcohol. In certain embodiments of the methods disclosed herein, inhalation formulations administered with a nebulizer further comprise at least one excipient. In certain embodiments, the excipient is selected from the group consisting of stabilizers and antioxidants (such as citric acid, ascorbic acid, ethylenediamine tetra acetic acid (EDTA), sodium metabisulfite, or a salt of any thereof), an osmolarity adjusting agent (such as sodium chloride, mannitol, or sorbitol), a surfactant (such as polysorbate 80, vitamin E, tocopherol polyethylene glycol, and Tyloxapol), or a pH buffer.

In certain embodiments of the methods disclosed herein, inhalation formulations administered with an inhalation device, e.g., a nebulizer, are hypotonic. In certain embodiments of the methods disclosed herein, inhalation formulations administered with an inhalation device, e.g., a nebulizer, are sub-isotonic. In certain embodiments of the methods disclosed herein, inhalation formulations administered with an inhalation device, e.g., a nebulizer, have an osmolality greater than about 70 mOsm/kg. In certain embodiments of the methods disclosed herein, inhalation formulations administered with an inhalation device, e.g., nebulizer, have an osmolality of at least about 100 mOsm/kg. In certain embodiments of the methods disclosed herein, inhalation formulations administered with an inhalation device, e.g., nebulizer, have an osmolality of at least about 150 mOsm/kg.

Combination Therapies

In certain embodiments of the methods disclosed herein, the formulations comprising from about 2% to about 90% by weight of cromolyn sodium are administered to a subject in need thereof by an inhalation device in combination with an additional agent used to treat IPF. In certain embodiments, the additional agent is selected from pirfenidone, an inhibitor of platelet-derived growth factor receptor (PDGFR) a, platelet-derived growth factor receptor (PDGFR) (3, an inhibitor of fibroblast growth factor receptor (FGFR) 1-3, an inhibitor of vascular endothelial growth factor receptor (VEGFR) 1-3, and an inhibitor of Fms-like tyrosine kinase-3 (FLT3). In certain embodiments, the additional agent is pirfenadone or nintedanib esylate. In certain embodiments, the additional agent is pifenadone. In certain embodiments, the additional agent is nintedanib esylate. In certain embodiments, the inhalation device is a nebulizer. In certain embodiments, the nebulizer is a high-efficiency nebulizer. In certain embodiments, the formulation administered to the subject using a nebulizer comprises an osmotic agent consisting of sodium chloride.

In certain embodiments are disclosed methods of treating of a subject having pulmonary fibrosis, including IPF, comprising administering to the subject a combination of (a) a pharmaceutical composition comprising from about 2% to about 99% by weight of cromolyn sodium and an osmotic agent consisting of sodium chloride, and (b) an additional agent. In certain embodiments, the additional agent is selected from pirfenidone, an inhibitor of platelet-derived growth factor receptor (PDGFR) a, platelet-derived growth factor receptor (PDGFR) β, an inhibitor of fibroblast growth factor receptor (FGFR) 1-3, an inhibitor of vascular endothelial growth factor receptor (VEGFR) 1-3, and an inhibitor of Fms-like tyrosine kinase-3 (FLT3). In certain embodiments, the additional agent is pirfenadone or nintedanib esylate. In certain embodiments, the additional agent is pifenadone. In certain embodiments, the additional agent is nintedanib esylate. In certain embodiments, the pharmaceutical composition comprises from about 2% by weight to about 6% by weight of cromolyn sodium and an ionic osmotic agent, and the inhalation device is a nebulizer. In certain embodiments, the nebulizer is a high-efficiency nebulizer. In certain embodiments, the pharmaceutical composition comprises from about 2% by weight to about 99% by weight of cromolyn sodium and the inhalation device is a dry-powder inhaler.

In certain embodiments of the methods disclosed herein, one or more different formulations of cromolyn or a pharmaceutically-acceptable salt thereof are co-administered by different routes of administration to provide systemically effective amounts of the cromolyn or a pharmaceutically-acceptable salt thereof. For example, in certain embodiments, a composition comprising cromolyn or a pharmaceutically-acceptable salt thereof, e.g., cromolyn sodium, is administered with a dry powder inhaler and a different composition comprising cromolyn or a pharmaceutically-acceptable salt thereof, e.g., cromolyn sodium, is co-administered in a liquid oral formulation for the treatment of a subject having pulmonary fibrosis, including IPF. In certain embodiments, a composition comprising cromolyn or a pharmaceutically-acceptable salt thereof, e.g., cromolyn sodium, is administered with a metered dose inhaler and a different composition comprising cromolyn or a pharmaceutically-acceptable salt thereof, e.g., cromolyn sodium, is co-administered in a liquid oral formulation for the treatment of a subject having pulmonary fibrosis, including IPF. In certain embodiments, a composition comprising cromolyn or a pharmaceutically-acceptable salt thereof, e.g., cromolyn sodium, is administered with a dry powder inhaler and a different composition comprising cromolyn or a pharmaceutically-acceptable salt thereof, e.g., cromolyn sodium, is co-administered with a metered dose inhaler to treatment of a subject having pulmonary fibrosis, including IPF. In certain embodiments, a composition comprising cromolyn or a pharmaceutically-acceptable salt thereof, e.g., cromolyn sodium, is administered with a dry powder inhaler and a different composition comprising cromolyn or a pharmaceutically-acceptable salt thereof, e.g., cromolyn sodium, is co-administered with a metered dose inhaler for the treatment of a subject having pulmonary fibrosis, including IPF. In certain embodiments, a composition comprising cromolyn or a pharmaceutically-acceptable salt thereof, e.g., cromolyn sodium, is administered with a nebulizer and a different composition comprising cromolyn or a pharmaceutically-acceptable salt thereof, e.g., cromolyn sodium, is co-administered in a liquid oral formulation for the treatment of a subject having pulmonary fibrosis, including IPF. In certain embodiments, a composition comprising cromolyn or a pharmaceutically-acceptable salt thereof, e.g., cromolyn sodium, is administered with a jet nebulizer and a different composition comprising cromolyn or a pharmaceutically-acceptable salt thereof, e.g., cromolyn sodium, is co-administered in a liquid oral formulation for the treatment of a subject having pulmonary fibrosis, including IPF.

EXAMPLES

Example 1: Pharmacokinetics of Cromolyn Sodium in Male BALB/c Mice

A pharmacokinetic analysis of cromolyn sodium in male BALB/c mice was undertaken wherein the concentration of cromolyn sodium in the plasma and lung of the mice was determined following a single intraperitoneal (IP) injection of cromolyn sodium.

BALB/c male mice, weighing 22±2 g, were provided by BioLasco Taiwan. All animals were maintained in a well-controlled temperature (20-24° C.) and humidity (30%-70%) environment with 12 hours light/dark cycles. The mice were given free access to a standard lab diet [MFG (Oriental Yeast Co., Ltd., Japan)] and autoclaved tap water.

Cromolyn sodium was formulated in 0.5% methylcellulose (MC)/0.2% Tween 80 to afford a homogenous solution. The solution was administered to the mice by IP injection at concentrations of 10 mg/kg and 100 mg/kg. The dosing volume for both dose strengths was 5 mL/kg.

The mice were sedated under general inhalant anesthesia (3% isoflurane) for blood collection by cardiac puncture. Blood aliquots (300-400 μL) were collected in tubes coated with lithium heparin and gently mixed, and then kept on ice and centrifuged at 2,500×g for 15 minutes at 4° C., within 1 hour after collection. The plasma was then harvested and kept frozen at −70° C. until receiving further processing. Immediately after the blood sampling, animals were decapitated and the lungs were removed, rinsed with cold saline (0.9% NaCl, g/mL), blotted with dry gauze, weighed, and kept frozen at −70° C. until receiving further processing within 1 hour of collection.

The plasma samples were processed using acetonitrile (ACN) precipitation and analyzed by LC-MS/MS. A plasma calibration curve was generated. Aliquots of drug-free plasma were spiked with the test substance at the specified concentration levels. The spiked plasma samples were processed together with the unknown plasma samples using the same procedure. The processed plasma samples were stored at −70° C. until receiving LC-MS/MS analysis, at which time peak areas were recorded, and the concentrations of the test substance in the unknown plasma samples were determined using the respective calibration curve. The reportable linear range of the assay was determined, along with the lower limit of quantitation (LLQ).

Each lung was homogenized in 1.5 mL cold phosphate-buffered saline (PBS) at pH 7.4 for 10 seconds on ice. The lung homogenate was centrifuged at 5,400×g for 15 minutes at 4° C., and the supernatant was subsequently processed using ACN precipitation and analyzed by LC-MS/MS. A lung calibration curve was generated. Aliquots of drug-free lung homogenate were spiked with the test substance at the specified concentration levels. The spiked lung homogenate samples were processed together with the unknown lung homogenate samples using the same procedure. The processed lung samples were stored at −70° C. until receiving LC-MS/MS analysis, at which time peak areas were recorded, and the concentrations of the test substance in the unknown lung samples were determined using the respective calibration curve. The reportable linear range of the assay was determined, along with the lower limit of quantitation (LLQ).

Plots of plasma and lung concentrations of compound versus time were constructed. The fundamental pharmacokinetic parameters of compound after IP dosing ($AUC_{last}$, $AUC_{INF}$, half life ($T_{1/2}$), clearance (Cl), Vz, Vss, Tmax, and Cmax) were obtained from the non-compartmental analysis (NCA) of the plasma data using WinNonlin. The plasma to lung ratios were calculated.

Significant exposure of cromolyn sodium in the plasma and lungs of the subject animals was achieved following a single intraperitoneal (IP) injection of cromolyn sodium in the mice.

The results of the PK study are shown in FIG. 1.

Example 2: Study of the Effect of Cromolyn Sodium in a Bleomycin Model of Pulmonary Fibrosis in Mice A study of the effect of the administration of cromolyn sodium to mice having pulmonary fibrosis was undertaken. Bleomycin is widely used to induce pulmonary fibrosis in rodents in order to study potential novel therapies for fibrosis. This study was designed to evaluate the therapeutic efficacy of a formulation of cromolyn sodium in a 21-day model of bleomycin induced pulmonary fibrosis in mice.

The cromolyn formulations tested in the study are described in Table 1:

TABLE 1

| Dosing Cohort | Dosing Schedule | Concentration of cromolyn sodium in dosing solution (mg/mL) |
| --- | --- | --- |
| 3 | 10 mg/kg BID | 2 |
| 4 | 30 mg/kg BID | 6 |
| 5 | 100 mg/kg BID | 20 |
| 6 | 30 mg/kg TID | 10 |

Animals were housed in a temperature-controlled room with a 12-hour light/dark cycle, with ad libitum access to water and irradiated laboratory chow throughout the study. Animals were individually identified by ear tags and were isolated in individual cages on evidence of aggression or cannibalism. A total of ninety C57B/L6 mice were included in the study and were divided into the six groups as described below and in Table 2.

Animals in groups 2 to 6 were administered 2 U/kg amounts of Blenoxane (Blenoxane, catalog number NDC 0703-3154-01 TEVA Pharmaceutical Works Ltd, Hungary) via oropharyngeal route as described in the article entitled "Mouse models of bleomycin induced pulmonary fibrosis" in *Current Protocols in Pharmacology*, Section 5.46.1. The animals in Group 1 were administered normal saline via oropharyngeal route.

Animals in Group 1 were administered vehicle via intraperitoneal (IP) route twice a day beginning from day 7 post-bleomycin until day 20, and once on day 21-post bleomycin administration. Volume=100 μL/dose. Total daily dose: 200 μL/day. N=15.

Bleomycin administered animals in Group 2 were administered vehicle via intraperitoneal (IP) route twice a day beginning from day 7 post-bleomycin until day 20, and once on day 21 post-bleomycin administration. Volume=100 μL/dose. Total daily dose: 200 μL/day. N=15.

Bleomycin administered animals in Group 3 were administered PA101B at a dose of 10 mg/kg/dose via intraperitoneal (IP) route twice a day beginning 7 post-bleomycin until day 20, and once on day 21 post-bleomycin administration. Volume=100 μL/dose. Total daily dose: 200 μL/day. N=15.

Bleomycin administered animals in Group 4 were administered PA101B at a dose of 30 mg/kg/dose via intraperitoneal (IP) route twice a day beginning from 7 post-bleomycin until day 20, and once on day 21 post-bleomycin administration Volume=100 μL/dose. Total daily dose: 200 μL/day. N=15.

Bleomycin administered animals in Group 5 were administered PA101B at a dose of 100 mg/kg/dose via intraperitoneal (IP) route twice a day beginning from 7 post-bleomycin until day 20, and once on day 21 post-bleomycin administration. Volume=100 μL/dose. Total daily dose: 200 μL/day. N=15.

Bleomycin administered animals in Group 6 were administered PA101B at a dose of 30 mg/kg/dose via intraperitoneal (IP) route three times a day beginning from 7 post-bleomycin until day 20, and once on day 21 post-bleomycin administration. Volume=70 μL/dose. Total daily dose: 210 μL/day. N=15.

The final dose of PA101B in groups 3 to 6 was provided on the morning of day 21 and animals were harvested between 2 to 4 hrs post dosing.

TABLE 2

Study design for Example 2.

| Group | #Mice | Dose of bleomycin— Day 0 | Treatment— Days 7 to 21 | Termination Day Post- Bleomycin Dose |
|---|---|---|---|---|
| 1 | 15 | None/saline | Vehicle BID | Day 21 |
| 2 | 15 | 2 U/kg Blenoxane | Vehicle BID | Day 21 |
| 3 | 15 | 2 U/kg Blenoxane | PA101B 10 mg/kg/dose—BID | Day 21 |
| 4 | 15 | 2 U/kg Blenoxane | PA101B 30 mg/kg/dose—BID | Day 21 |
| 5 | 15 | 2 U/kg Blenoxane | PA101B 100 mg/kg/dose—BID | Day 21 |
| 6 | 15 | 2 U/kg Blenoxane | PA101B 30 mg/kg/dose—TID | Day 21 |

All surviving animals were euthanized 21 days following the start of the study. Immediately after euthanization, blood was collected from each animal by terminal cardiac bleed into EDTA tubes and placed on ice. Blood was collected in EDTA coated tubes, centrifuged and plasma prepared. Plasma was stored frozen at −80° C. until analysis.

Lungs were harvested from five animals from each group and weighed. The lungs were then snap frozen and stored at −80° C. until used for the analysis of hydroxyproline levels and collagen levels using commercial kits produced for this purpose.

Lungs from the remaining animals from each group were harvested, weighed and bronchoalveolar lavage fluid (also known as "BAL," or "bronchoalveolar washing") was collected from the lungs of the animals by lavaging the lungs twice with 0.5 mL of Hanks balanced salt solution. The lungs were then inflated by use of 0.3 mL of 10% NBF for histopathological analysis.

The BAL fluid was centrifuged at 1,000 rpm at 4° C. for 5 minutes to produce a BAL cell pellet and supernatant fluid. The supernatant fluid was transferred to several labeled tubes (100 μL, 100 μL and remaining), frozen and stored at −80° C. until further use. The BAL cell pellet was suspended in 2 mL of 1× Pharmalyse buffer (BD Bioscience) to lyse the red blood cells (RBCs). PBS+2% fetal bovine serum (FBS) was added to stop the lysis reaction and cells were again centrifuged. Leukocytes remaining in the cell pellet were counted using a hemocytometer and the trypan blue exclusion method. A portion of the BAL cells were used to make cytospins and were stained with Geimsa stain. Differential counts were then performed.

The resulting BAL fluid was analyzed for histamine levels and tryptase levels using commercial ELISA kits according to the instructions provided by the manufacturer.

Figure 2:
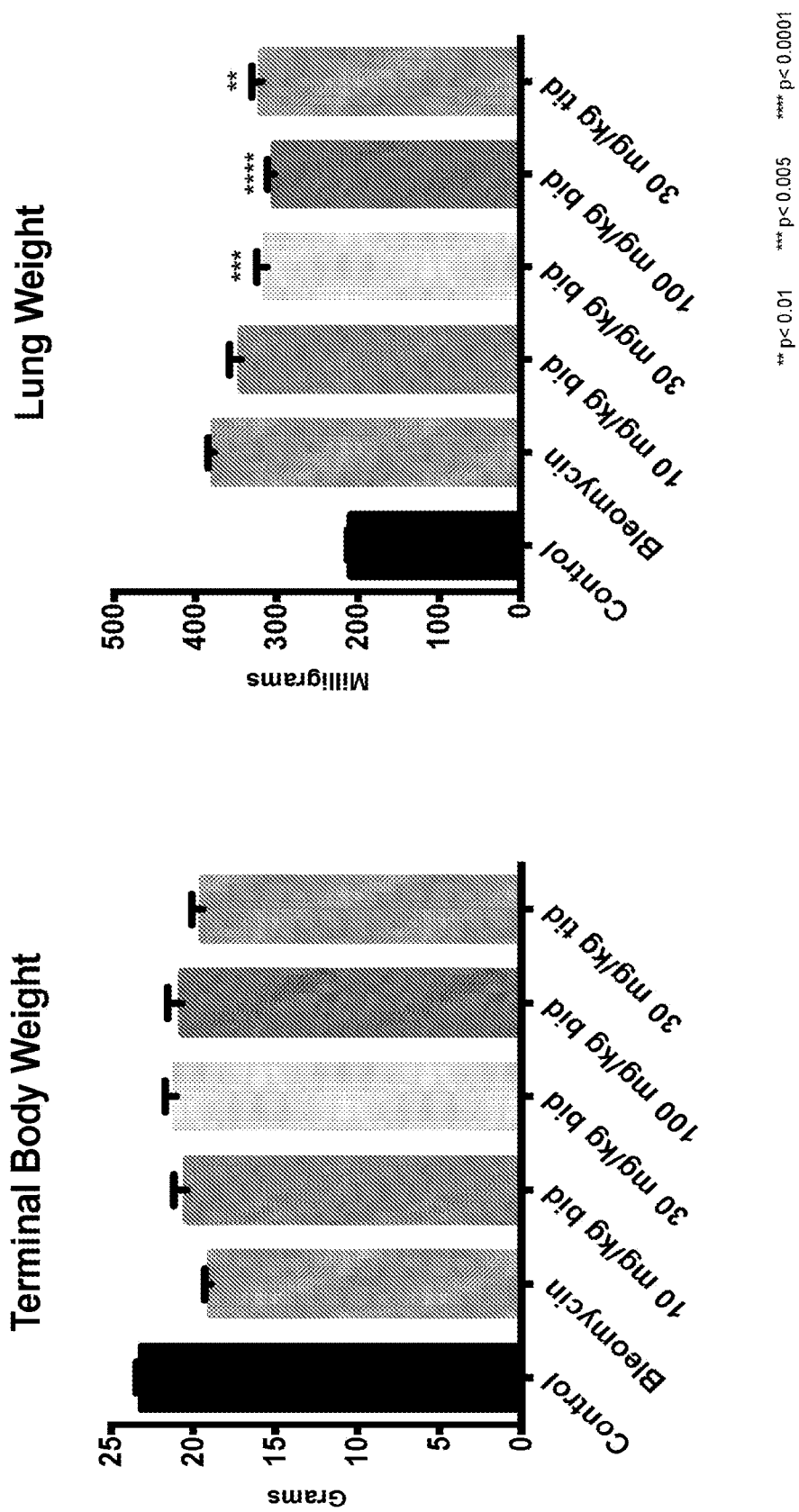
FIG. 2 is a graphic representation of the total body weight and lung weights in the animals from Example 2.

The terminal body weights and lung weights for animals from each of groups 1 to 6 are shown in FIG. 2. With respect to the lung of the bleomycin-administered animals, there was a statistically significant difference in the lung weights between the animals in group 2 (bleomycin-administered, but no treatment with PA101B), and the animals in groups 4 ($p<0.01$), 5 ($p<0.005$), and 6 ($p<0.0001$) that were treated with the PA101B cromolyn sodium pharmaceutical composition, indicating that treatment of the animals in those groups with PA101B had a statistically significant effect on reducing edema and inflammation in the lungs of the animals compared to the animals that did not receive such treatment.

The animals in group 2 (bleomycin-administered, but not receiving treatment with PA101B) exhibited fold-increases in the average total number of cells, average number of neutrophils, and average number of macrophages in BAL fluid compared to the averages in the animals of control group 1 of 5.3, 28.3, and 7.2, respectively. The summary of the percentage change in the average total number of cells, the average number of neutrophils and the average number of macrophages in the BAL fluid of the animals in groups 3, 4, 5, and 6 as compared to the animals in group 2 is found in Table 3 below.

TABLE 3

| Group | Average Total Cells in BAL Fluid (% change relative to Group 2) | Average Neutrophils in BAL Fluid (% change relative to Group 2) | Average Macrophages in BAL Fluid (% change relative to Group 2) |
|---|---|---|---|
| 3 | −5.5 | −32.9 | −24.7 |
| 4 | −29.3 | −84.6 | −53.0 |
| 5 | −32.1 | −75.8 | −61.8 |
| 6 | −10.8 | −79.3 | −40.4 |

Figure 3:
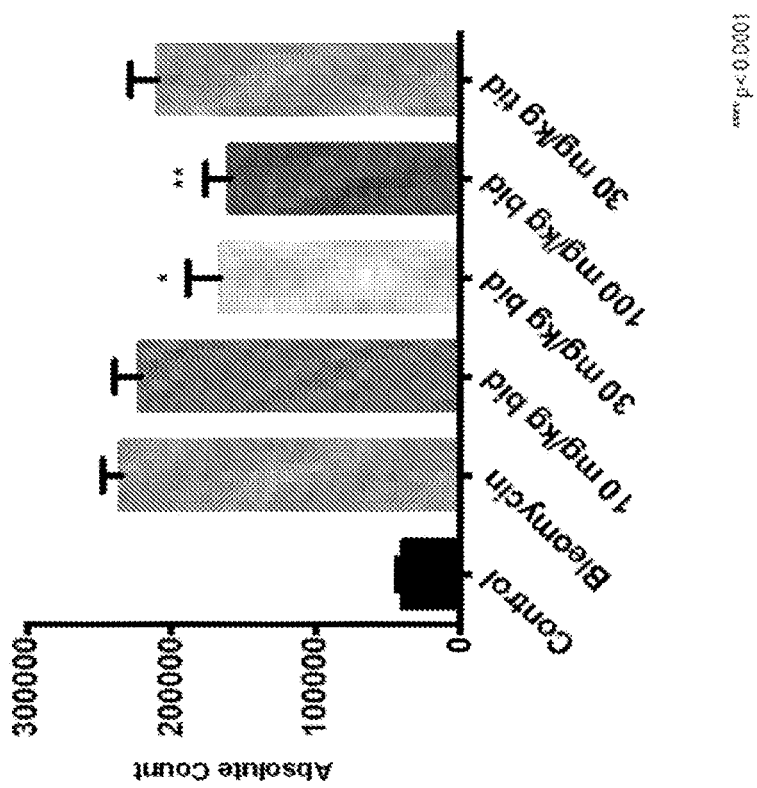
FIG. 3 is a graphic representation of the total number of cells in the BAL fluid from the animals in Example 2.

The average total cells in the BAL fluid of the animals in each of groups 1 to 6 is shown in FIG. 3. There was a statistically significant reduction in the total cells in the BAL fluid of animals in treatment groups 4 and 5 compared to the bleoymycin-treated animals in group 2 that did not receive treatment with PA101B.

Figure 4:
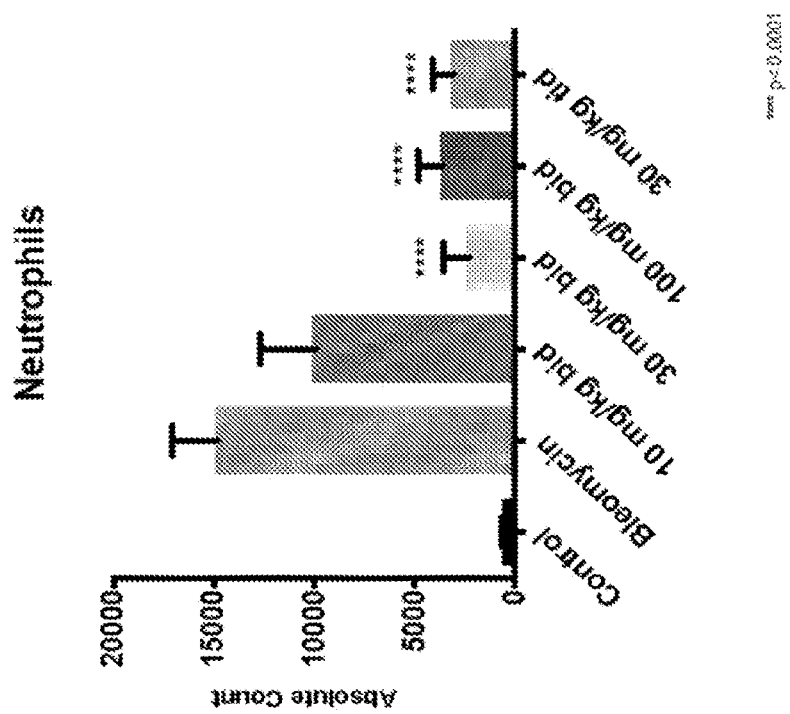
FIG. 4 is a graphic representation of the number of neutrophils in the BAL fluid from the animals in Example 2.

The average number of neutrophils in the BAL fluid from the animals in each of groups 1 to 6 is shown in FIG. 4. There was a statistically significant reduction in the number of neutrophils in the BAL fluid of animals from treatment groups 4, 5, and 6 (p<0.001) compared to the bleomycin-administered animals in group 2 that did not receive treatment with PA101B.

Figure 5:
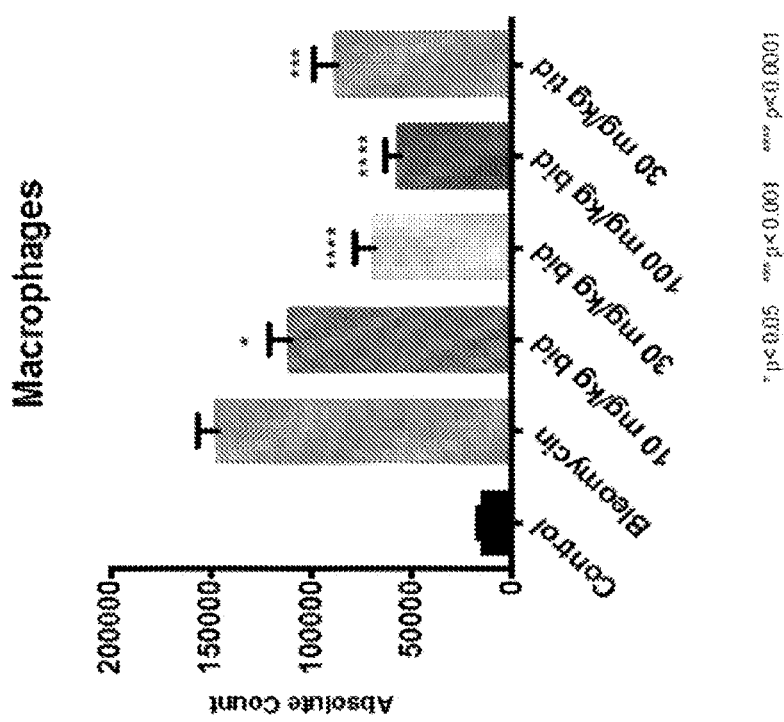
FIG. 5 is a graphic representation of the number of macrophages in the BAL fluid from the animals in Example 2.

The average number of macrophages in the BAL fluid from the animals in each of groups 1 to 6 is shown in FIG. 5. There was a statistically significant reduction in the number of macrophages in the BAL fluid of animals from treatment groups 3 (p<0.05), 4 (p<0.0001), 5 (p<0.0001), and 6 (p<0.001) compared to the bleomycin-administered animals in group 2 that did not receive treatment with PA101B.

Figure 6:
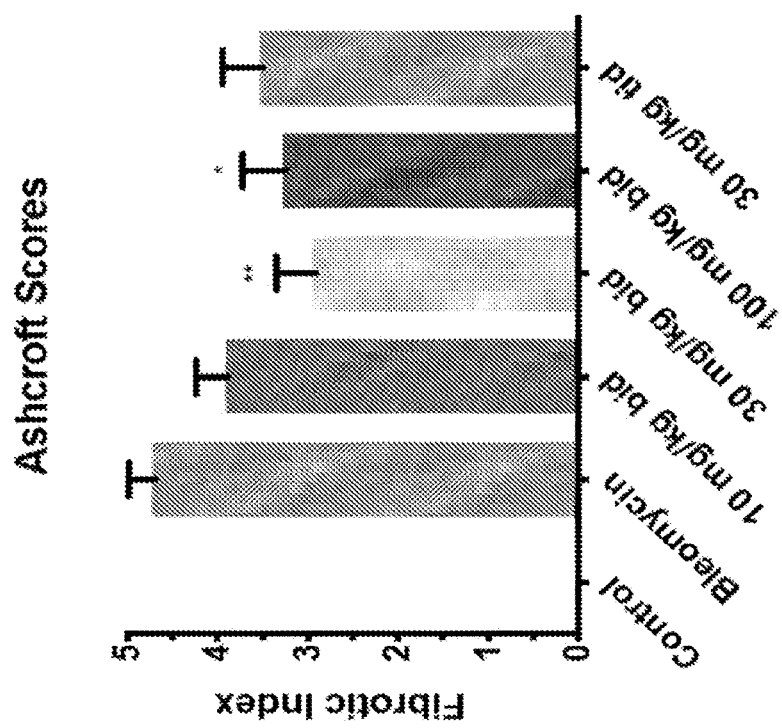
FIG. 6 is a graphic representation of the Ashcroft scores derived from the animals in Example 2.

The Ashcroft scores of the lungs of the animals in groups 2 to 6 is shown in FIG. 6. The Ashcroft scores were determined according to procedures known to those having ordinary skill in the art (see, for example, Ashcroft, T., J. M. Simpson, and V. Timbrell. 1988. Simple method of estimating severity of pulmonary fibrosis on a numerical scale. J. Clin. Pathol. 41:467-470; Hubner, R. H., Gitter, W., El Mokhtari, N. E., Mathiak, M., Both, M., Bolte, H., Bewig, B. (2008). Standardized quantification of pulmonary fibrosis in histological samples. BioTechniques, 44(4), 507-517.). There was a statistically significant difference in the Ashcroft scores between the animals in groups 4 and 5, and the animals in group 2.

Figure 7:
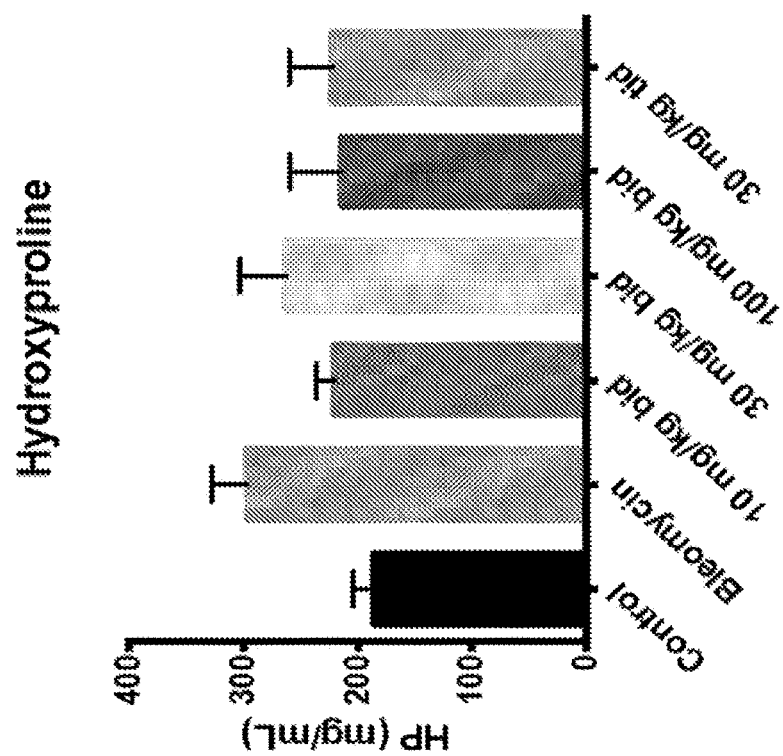
FIG. 7 is a graphic representation of the hydroxyproline content in the lungs derived from the animals in Example 2.

The hydroxyproline content of the lung tissue in the animals (measured in mg/mL) from groups 1 to 6 is shown in FIG. 7.

Figure 8:
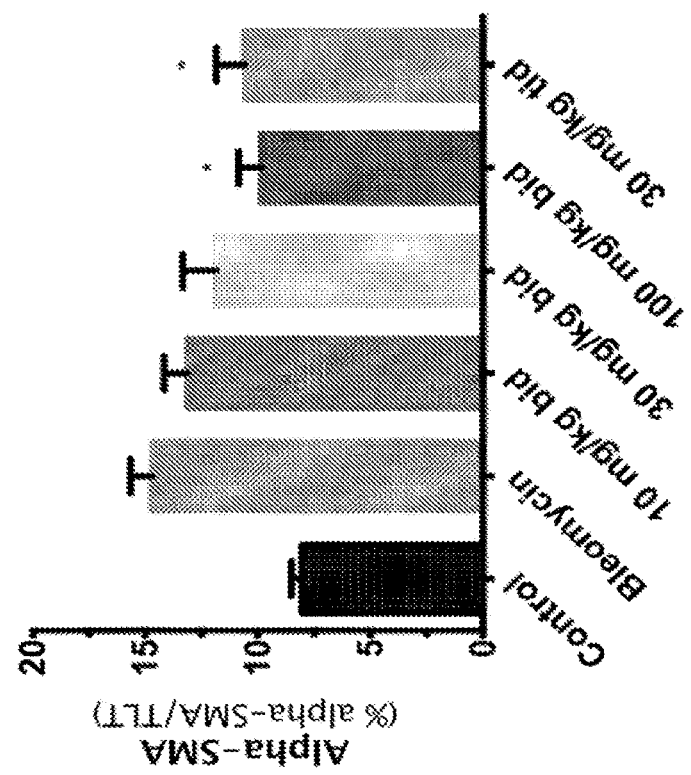
FIG. 8 is a graphic representation of the amount of alpha-smooth muscle actin (alpha-SMA) in the lungs derived from the animals in Example 2, wherein the dosing regimen is represented on the X-axis and the Y-axis represents the expression of alpha-SMA and is expressed as % alpha-SMA/total lung tissue area (TLT).

The expression of alpha-smooth muscle actin (alpha-SMA) in the lung tissue of animals of groups 1 to 6 is shown in FIG. 8. There was a statistically significant difference between expression of alpha-SMA in the animals of treatment groups 5 and 6 compared to the animals in group 2.

In summary, animals receiving a dose of bleomycin and subsequently treated with a range of doses of a pharmaceutical composition PA101B, which comprises cromolyn sodium, generally exhibited a reduction in markers related to inflammation, a reduction of collagen content in the lung, a reduction in myofibroblast formation in the lung, and a dose-dependent reduction in lung fibrosis compared to animals that received a dose of bleomycin and did not receive treatment with PA101B.

Example 3: Stability of Cromolyn Sodium Formulations

The compositions and formulations of the disclosure are both physically and chemically stable.

As shown by the physical appearance, Table 4 demonstrates that each formulation remains clear, and, therefore, free of any precipitate, from manufacture through the 24-month time point (i.e. for at least 24 months) when the formulations are stored at 25° C. As shown by the physical appearance, Table 4 demonstrates that each formulation remains clear, and, therefore, free of any precipitate, from manufacture through the 24-month time point (i.e. for at least 24 months) when the formulations are stored at 40° C.

As shown by the chemical measures of pH and osmolality, Table 4a demonstrates that each formulation maintains consistent appearance, pH and osmolality, assay and related substances from manufacture through the 24-month time point (i.e. for at least 24 months) when the formulations are stored at 25° C. As shown by the chemical measures of pH and osmolality, Table 4b demonstrates that each formulation maintains consistent appearance, pH and osmolality, assay and related substances from manufacture through the 6-month time point (i.e. for at least 6 months) when the formulations are stored at 40° C.

TABLE 4a

Stability data at 25° C.

| | | | | | Stability Duration | | | | |
|---|---|---|---|---|---|---|---|---|---|
| | | T0 | 3 months | 6 months | 9 months | 12 months | 18 months | 24 months |
| Appearance | PA101, 20 mg/mL | Clear | Clear | Clear | | Clear | | Clear |
| | PA101, 40 mg/mL | Clear | Clear | Clear | | Clear | Clear | Clear |
| | PA101B, 10 mg/mL | Clear | Clear | Clear | Clear | Clear | Clear | |
| | PA101B, 20 mg/mL | Clear | Clear | Clear | Clear | Clear | Clear | |
| | PA101B, 40 mg/mL | Clear | Clear | Clear | Clear | Clear | Clear | Clear |
| | PA101B, 60 mg/mL | Clear | Clear | Clear | Clear | Clear | | Clear |
| | KM104, 60 mg/mL | Clear | Clear | | | Clear | Clear | Clear |
| pH | PA101, 20 mg/mL | 5.3 | 5.6 | 5.5 | | 5.8 | | 5.8 |
| | PA101, 40 mg/mL | 5.4 | 5.7 | 5.5 | | 5.9 | 5.7 | 5.8 |
| | PA101B, 10 mg/mL | 5.5 | 6.1 | 5.9 | 5.7 | 5.4 | 6.2 | |
| | PA101B, 20 mg/mL | 5.7 | 6.2 | 5.7 | 5.8 | 5.4 | 6 | |
| | PA101B, 40 mg/mL | 5.5 | 6 | 6 | 5.8 | 5.9 | 6.32 | 5.94 |
| | PA101B, 60 mg/mL | 5.2 | 5.3 | 5.4 | 5.5 | 5.6 | | 5.6 |
| | KM104, 60 mg/mL | 5.6 | 5.6 | | | 5.8 | 5.9 | 5.8 |
| Osmolality (mOsm/kg) | PA101, 20 mg/mL | 195 | 192 | 194 | | 196 | | 1 95 |
| | PA101, 40 mg/mL | 204 | 202 | 203 | | 206 | 205 | 204 |
| | PA101B, 10 mg/mL | 106 | 108 | 105 | 106 | 105 | 110 | |
| | PA101B, 20 mg/mL | 117 | 114 | 117 | 117 | 116 | 124 | |
| | PA101B, 40 mg/mL | 126 | 126 | 127 | 126 | 128 | 125 | 126 |
| | PA101B, 60 mg/mL | 138 | 138 | 138 | 142 | N/A | | 144 |
| | KM104, 60 mg/mL | 294 | 288 | | | 291 | 289 | 291 |
| Assay (% Label claim) | PA101, 20 mg/mL | 101.8 | 103.6 | 102.6 | | 102.6 | | 104.6 |
| | PA101, 40 mg/mL | 102.4 | 102.6 | 101.8 | | 96.9 | 100.6 | 104.3 |
| | PA101B, 10 mg/mL | 98.9 | 102.2 | 102.2 | 100.8 | 101.2 | 96.7 | |
| | PA101B, 20 mg/mL | 98.1 | 101.7 | 98.7 | 100.2 | 99.1 | 96.6 | |
| | PA101B, 40 mg/mL | 97.3 | 99.2 | 101.1 | 103.7 | 100.7 | 98.9 | 101.6 |
| | PA101B, 60 mg/mL | 98.7 | 100.8 | 100.7 | 101.8 | 99.9 | | 102.2 |
| | KM104, 60 mg/mL | 100 | 100.4 | | | 98.7 | 101.1 | 100.8 |

TABLE 4a-continued

Stability data at 25° C.

| | | | Stability Duration | | | | | |
|---|---|---|---|---|---|---|---|---|
| | | T0 | 3 months | 6 months | 9 months | 12 months | 18 months | 24 months |
| Related substance (% total) | PA101, 20 mg/mL | 0.11 | 0.11 | 0.11 | | 0.11 | | <LOD |
| | PA101, 40 mg/mL | 0.11 | 0.11 | 0.11 | | 0.11 | <LOD | <LOD |
| | PA101B, 10 mg/mL | 0.11 | <LOD | N/A | <LOD | <LOD | <LOD | |
| | PA101B, 20 mg/mL | 0.11 | <LOD | <LOD | <LOD | <LOD | <LOD | |
| | PA101B, 40 mg/mL | 0.11 | 0.11 | <LOD | <LOD | <LOD | <LOD | <LOD |
| | PA101B, 60 mg/mL | 0.1 | 0.1 | 0.1 | 0.1 | 0.1 | | 0.1 |
| | KM104, 60 mg/mL | 0.1 | 0.1 | | | 0.1 | 0.2 | <LOD |

* LOD: Limit of detection

TABLE 4b

Stability data at 40° C.

| | | | Stability Duration | | | |
|---|---|---|---|---|---|---|
| | | T0 | 1 month | 2 months | 3 months | 6 months |
| Appearance | PA101, 20 mg/mL | Clear | | | Clear | Clear |
| | PA101, 40 mg/mL | Clear | Clear | Clear | | |
| | PA101B, 10 mg/mL | Clear | Clear | Clear | Clear | Clear |
| | PA101B, 20 mg/mL | Clear | Clear | Clear | Clear | Clear |
| | PA101B, 40 mg/mL | Clear | Clear | Clear | Clear | Clear |
| | KM104, 60 mg/mL | Clear | Clear | | Clear | Clear* |
| pH | PA101, 20 mg/mL | 5.3 | 5.6 | | 5.8 | 5.6 |
| | PA101, 40 mg/mL | 5.4 | 5.6 | | 5.8 | 5.7 |
| | PA101B, 10 mg/mL | 5.5 | 5.9 | 6.4 | 6.1 | 5.6 |
| | PA101B, 20 mg/mL | 5.7 | 5.9 | 5.8 | 6.3 | 5.9 |
| | PA101B, 40 mg/mL | 5.5 | 6.0 | 5.9 | 5.8 | 5.9 |
| | KM104, 60 mg/mL | 5.6 | 5.5 | | 5.6 | 5.7* |
| Osmolality mOsm/kg | PA101, 20 mg/mL | 195 | 206 | | 193 | 192 |
| | PA101, 40 mg/mL | 204 | 206 | | 203 | 205 |
| | PA101B, 10 mg/mL | 106 | 108 | 107 | 109 | 105 |
| | PA101B, 20 mg/mL | 117 | 117 | 117 | 118 | 117 |
| | PA101B, 40 mg/mL | 126 | 127 | 128 | 126 | 128 |
| | KM104, 60 mg/mL | 294 | 293 | | 288 | 292* |
| Assay (% Label claim) | PA101, 20 mg/mL | 101.8 | 102.9 | | 102.9 | 102.7 |
| | PA101, 40 mg/mL | 102.4 | 102.9 | | 102.5 | 101.4 |
| | PA101B, 10 mg/mL | 98.9 | 98.9 | 98.9 | 100.3 | 103.6 |
| | PA101B, 20 mg/mL | 98.1 | 98.5 | 98.8 | 100.2 | 98.1 |
| | PA101B, 40 mg/mL | 97.3 | 98.0 | 98.9 | 99.2 | 101.8 |
| | KM104, 60 mg/mL | 100 | 100.1 | | 99.8 | 99.5 |
| Related substance (% total) | PA101, 20 mg/mL | 0.11 | 0.11 | | 0.11 | 0.11 |
| | PA101, 40 mg/mL | 0.11 | 0.11 | | 0.11 | 0.11 |
| | PA101B, 10 mg/mL | 0.11 | 0.11 | <LOD | <LOD | <LOD |
| | PA101B, 20 mg/mL | 0.11 | 0.11 | <LOD | <LOD | <LOD |
| | PA101B, 40 mg/mL | 0.11 | 0.1 | 0.11 | 0.11 | <LOD |
| | KM104, 60 mg/mL | 0.11 | <LOD | | 0.11 | 0.11* |

*KM104 data are at 13 months duration

Example 4: Safety and Tolerability of Inhaled PA101 in IPF Subjects with Chronic Cough PA101 contains 4% (by weight) cromolyn as the active substance, 0.2% sodium chloride as an osmotic agent, 0.02% EDTA as a chelating agent, 1.25% mannitol as a non-ionic osmotic agent, and purified water q.s. PA101 has an osmolality of 200 mOsm/kg. Placebo A contained 0.4% sodium chloride as an osmotic agent, 0.02% EDTA as a chelating agent, 1.25% mannitol as a non-ionic osmotic agent, and purified water q.s., but no cromolyn sodium. The osmolality of Placebo A was adjusted to about 200 mOsm/kg. Placebo B contained 0.6% sodium chloride as an osmotic agent, 0.02% EDTA as a chelating agent, and purified water q.s., but no cromolyn sodium or mannitol. The osmolality of Placebo B was adjusted to about 200 mOsm/kg.

A primary objective of the study was to assess the safety and tolerability of inhaled PA101 (including the excipient mannitol in the formulation) in IPF subjects with refractory chronic cough. A secondary objective of the study was to assess the efficacy potential of inhaled PA101 after 3 days dosing.

The study design was as follows: Phase 1b, randomized, double-blind, single-center, 3-period crossover study in 6 IPF subjects (40-79 years of age) with refractory chronic cough. Each study treatment administered three times daily (TID) for 3 days and one dose the next day (total of 10 doses). 72-hours continuous monitoring for cough count.

The treatments given were one of the following: 1) 40 mg PA101, 2) Placebo-A (A=without cromolyn sodium, but included mannitol), and 3) Placebo-B (B=without mannitol and without cromolyn sodium). All treatments administered as oral inhalation using eFlow nebulizer.

Following administration of the treatment and two placebos to the subjects, any adverse events were recorded. Table 5 provides a summary of adverse events, divided by severity, type, and treatment.

TABLE 5

| Adverse Events | | | |
|---|---|---|---|
| | Placebo A (n = 6) | Placebo B (n = 6) | PA101 40 mg (n = 6) |
| Subjects with at least one AE | 2 (33.3%) | 3 (50%) | 5 (83.3%) |
| Related AEs | 1 (16.7%) | 2 (33.30%) | 5 (83.3%) |
| Not related AEs | 1 (16.7%) | 2 (33.30%) | 3 (50%) |
| Mild AEs | 2 (33.30%) | 3 (50%) | 5 (83.3%) |
| Moderate AEs | 0 | 0 | 1 (16.7%) |
| Severe AEs | 0 | 0 | 0 |
| Cough | 1 (16.7%) | 0 | 4 (66.7%) |
| Throat Irritation | 1 (16.7%) | 0 | 3 (50%) |
| Oropharyngeal pain | 0 | 0 | 1 (16.7%) |
| Rhinorrhoea | 0 | 0 | 1 (16.7%) |
| Dizziness | 1 (16.7%) | 2 (33.30%) | 2 (33.30%) |
| Headache | 0 | 1 (16.7%) | 2 (33.30%) |
| Chills | 0 | 0 | 1 (16.7%) |
| Malaise | 0 | 1 (16.7%) | 0 |
| Flushing | 1 (16.7%) | 0 | 1 (16.7%) |
| Defecation urgency | 0 | 0 | 1 (16.7%) |
| Nausea | 1 (16.7%) | 1 (16.7%) | 0 |
| Nasopharyngitis | 1 (16.7%) | 0 | 0 |

Figure 9:
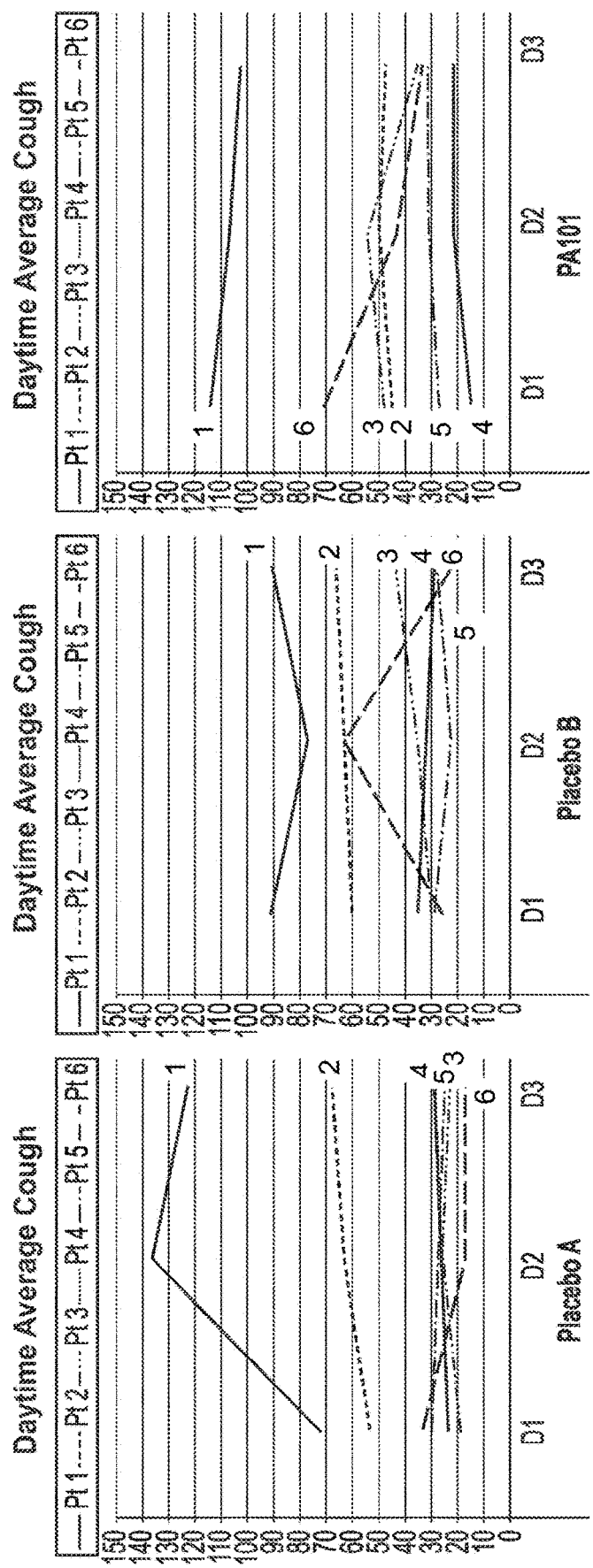
FIG. 9 is a series of graphs showing the average number of daytime coughs for each subject in Example 4 following treatment with either PA101 or with one of two placebo treatments.
Figure 10:
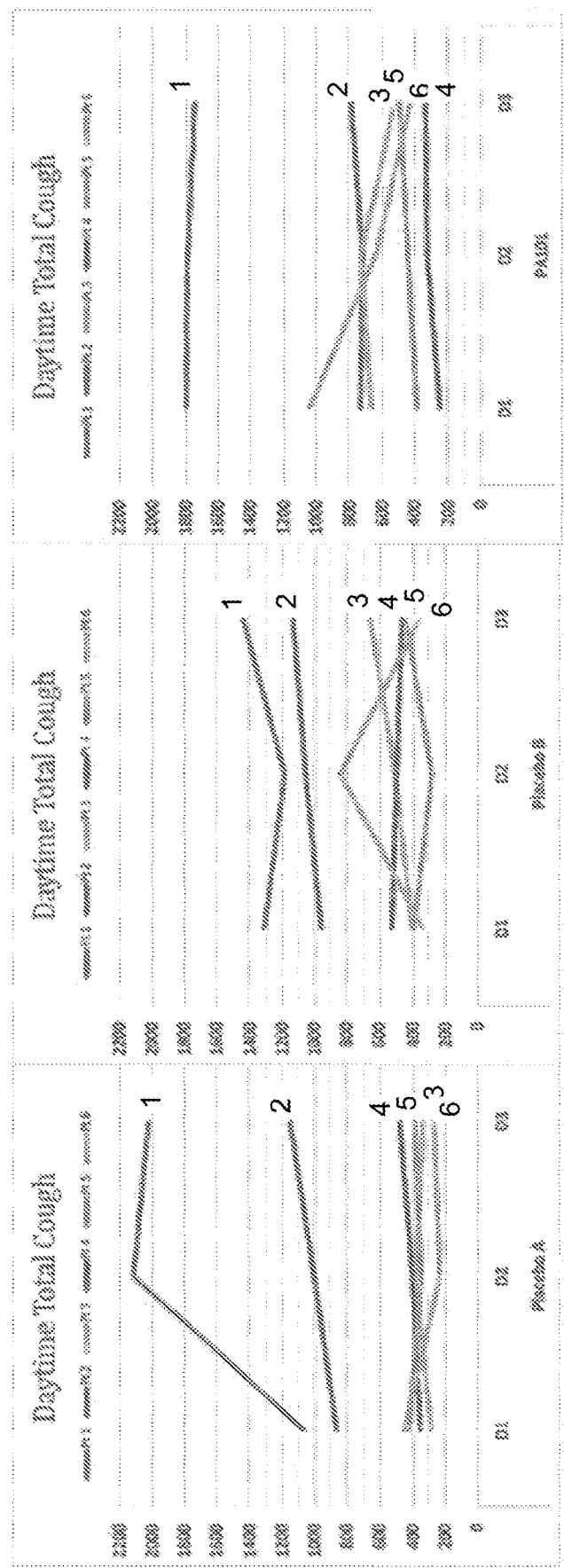
FIG. 10 is a series of graphs showing the total number of daytime coughs for each subject in Example 4 following treatment with either PA101 or with one of two placebo treatments.

Following administration of the treatment and two placebos to the subjects, the number of daytime coughs was recorded for each subject. FIG. 9 provides a summary of the average number of coughs at three daytime time points for each subject. FIG. 10 provides a summary of the total number of coughs at three daytime time points for each subject.

Whereas the number of coughs provided in FIGS. 9 and 10 are based upon subjective subject reports, the following cough counts are based upon an objective measure. To obtain an objective count of the subjects' coughs, the study used the Leicester Cough Monitor (LCM), a validated 24-h automated cough frequency monitor. The LCM requires the subject to wear a microphone adhered to the subject's chest and attached to a monitor (carried with shoulder strap) that is present on the subject 24 hours each day to record all coughs.

Table 6 provides the LCM count of the average cough per hour for each subject in each treatment condition as well as a breakout of the data across 24 hours, daytime hours, and nighttime hours. SD=Standard Deviation.

TABLE 6

| | | LCM Cough Count | | | | | |
|---|---|---|---|---|---|---|---|
| | | Placebo A | | Placebo B | | PA101 | |
| | | Mean | SD | Mean | SD | Mean | SD |
| 24 hr Cough/hr | Day 1 | 25 | 13 | 30 | 18 | 35 | 23 |
| | Day 2 | 33 | 31 | 32 | 15 | 34 | 21 |
| | Day 3 | 34 | 28 | 32 | 18 | 32 | 22 |
| | ΔD3 vs. D1 | 8.3 | 16.7 | 2.0 | 5.4 | −3.3 | 11.6 |

TABLE 6-continued

| | | LCM Cough Count | | | | | |
|---|---|---|---|---|---|---|---|
| | | Placebo A | | Placebo B | | PA101 | |
| | | Mean | SD | Mean | SD | Mean | SD |
| Daytime Cough/hr | Day 1 | 38 | 20 | 45 | 26 | 53 | 36 |
| | Day 2 | 48 | 25 | 48 | 22 | 51 | 30 |
| | Day 3 | 47 | 26 | 46 | 27 | 45 | 30 |
| | ΔD3 vs. D1 | 8.6 | 22.8 | 1.0 | 7.3 | −8.5 | 16.2 |
| Nighttime Cough/hr | Day 1 | 4 | 1 | 7 | 6 | 4 | 2 |
| | Day 2 | 4 | 2 | 5 | 4 | 5 | 2 |
| | Day 3 | 4 | 4 | 3 | 2 | 6 | 5 |
| | ΔD3 vs. D1 | 0.3 | 4.5 | −4.2 | 6.6 | 2.0 | 3.8 |

The study includes two additional subjective measures: Cough Severity and Urge-to-Cough, both provided quantitatively as a measure on a visual analogue scale (VAS). When using the visual analogue scale (VAS), for example, to measure cough severity, the subject is asked to mark on a 100 mm scale between 'no cough' and 'the worst cough severity'. When using the visual analogue scale (VAS), for example, to measure urge-to-cough, the subject is asked to mark on a 100 mm scale between 'no urge' and 'the worst urge-to-cough'.

Table 7 provides the mean, standard deviation (SD) and median scores on the VAS for each parameter by treatment at either day 1 or day 4 of the study.

TABLE 7

| Parameter (unit) | Treatment | Visit | Mean | SD | Median |
|---|---|---|---|---|---|
| Cough Severity (mm) | Placebo A | Day 1 | 61.7 | 18.4 | 62.0 |
| | | Day 4 | 64.0 | 13.5 | 58.0 |
| | Placebo B | Day 1 | 68.2 | 11.5 | 66.5 |
| | | Day 4 | 67.3 | 15.0 | 72.0 |
| | 40 mg PA101 | Day 1 | 68.5 | 10.3 | 70.5 |
| | | Day 4 | 67.0 | 20.6 | 72.0 |
| Urge-to-Cough (mm) | Placebo A | Day 1 | 62.5 | 16.5 | 62.0 |
| | | Day 4 | 58.0 | 19.2 | 52.0 |
| | Placebo B | Day 1 | 69.2 | 12.1 | 72.5 |
| | | Day 4 | 70.0 | 14.3 | 72.5 |
| | 40 mg PA101 | Day 1 | 70.7 | 11.4 | 72.5 |
| | | Day 4 | 67.5 | 20.1 | 70.0 |

Figure 11:
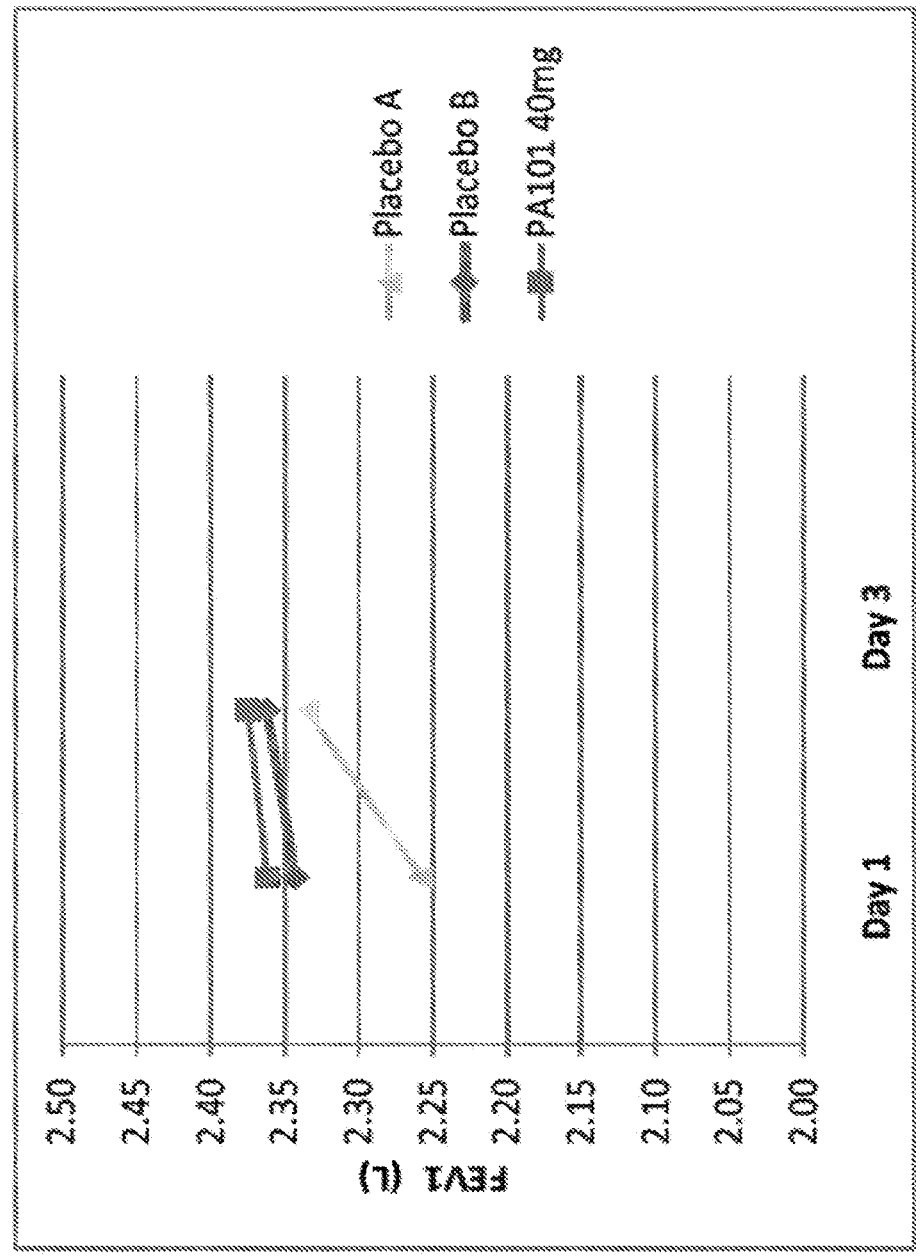
FIG. 11 is a graph depicting pulmonary function (measured as Forced Expiratory Volume in One Second (FEV1)) as a function of time for each of the treatment groups described in Example 4.

To assess pulmonary function of each of the subjects following treatment with PA101 or with one of the two placebo formulations, the subjects were evaluated using a forced vital capacity (FVC) test. The Forced Expiratory Volume in One Second (FEV1), the amount of air that is forcefully exhaled in the first second of the FVC test, was measured for each subject either on Day 1 or Day 3 of treatment. FIG. 11 summarizes the results for each treatment group.

The data from this study indicated that treatment with 40 mg PA101 including mannitol as the excipient in the formulation was overall safe and well tolerated following administration three times daily for 3 days in IPF subjects with refractory chronic cough. No difference in tolerability was observed between PA101 formulated with mannitol, placebo with mannitol, and placebo without mannitol. The majority of the adverse events were of mild intensity and did not require treatment. Most commonly reported adverse events were cough, throat irritation, dizziness, and headache. There were no clinically significant changes in cough count, severity of cough and urge to cough between the treatment groups following 3 days of treatment.

Example 5: Pharmacokinetics, Relative Bioavailability, and Safety Study of PA101 in Healthy Subjects (PK-01)

The primary objective of the study is to determine the systemic availability and pharmacokinetic (PK) profile of single doses of a representative inhaled cromolyn sodium formulation (PA-101) delivered via a nebulizer (eFlow®, PARI) using two different aerosol membranes (30 L and 40 L) in comparison with marketed formulations of cromolyn sodium (oral solution and an inhalation aerosol) in healthy subjects.

The secondary objective of the study is to assess the safety and tolerability of PA-101 in comparison with marketed formulations of cromolyn sodium (oral solution and an inhalation aerosol).

This was a Phase 1, randomized, open-label, single-centre, dose-ranging, cross-over study conducted in a total of 12 healthy adult subjects of 18-45 years of age.

Study Treatments, Dose and Mode of Administration:
1. 40 mg PA-101 (4% DSCG, 40 mg/1 mL), oral inhalation via eFlow 30 L.
2. 80 mg PA-101 (4% DSCG, 80 mg/2 mL), oral inhalation via eFlow 30 L.
3. 40 mg PA-101 (4% DSCG, 40 mg/1 mL), oral inhalation via eFlow 40 L.
4. 20 mg cromolyn sodium inhalation aerosol (1% DSCG, 20 mg/2 mL) (commercially available product), oral inhalation via LC Plus.
5. 200 mg oral sodium cromoglycate solution (commercially available product), oral administration.

All study subjects received each study treatment in the morning (at 8:00 am, +/−30 minutes) as a single dose treatment. Prior to each dosing day, subjects were admitted to the clinic in the morning for baseline (pre-dose) assessments. Subjects were required to remain in the clinic for 12 h after study drug administration on each dosing day. Treatment Visits were separated by a washout period of 2 to 5 days.

The main delivery device for administering PA-101 was the open system eFlow nebulizer using the 30 L aerosol head, which generates aerosol particles with a median size of about 3.0 μm. The duration of the study was one day.

Criteria for Evaluation:
Pharmacokinetic Measurements:
The PK parameters evaluated for plasma cromolyn sodium (DSCG) were maximum concentration ($C_{max}$), time to maximum concentration ($T_{max}$), terminal elimination half-life ($T_{1/2}$), area under the plasma concentration-time curve from time=0 to time of last measurable drug concentration ($AUC_{0-t}$), and area under the plasma concentration-time curve from time=0 to infinity ($AUC_{0-\infty}$). Urine DSCG levels were measured for total DSCG excretion in the urine, and the bioavailability of the DSCG was calculated from the measured levels.

Safety Measurements:
Adverse events including gastrointestinal disturbance (e.g., abdominal pain, nausea, vomiting), changes in vital signs, 12-lead ECG and clinical laboratory tests (hematology, chemistry and urinalysis).

Statistical Measurements:
Pharmacokinetic parameters and plasma concentrations are listed and summarized. The summary statistics are presented as the geometric mean, arithmetic mean, arithmetic standard deviation (SD), min, median, max and n. The geometric statistics are not presented for Tmax. Analysis of variance (ANOVA) including terms for subject and treatment are used to calculate point estimates, and confidence intervals (CI) for treatment differences with respect to PK parameters (90% CI) are calculated.

The incidence of AEs was compared between treatment groups: Summary tables and individual subject listings are provided for all safety measurements and the results are presented by treatment group. Descriptive statistics are used to summarize data where appropriate.

Results:
The pharmacokinetic parameters measured in the single dose study are shown in the following table:

TABLE 8

| PK parameter | Oral solution, 200 mg | Inhalation aerosol, 20 mg (Intal) | PA-101 (40L), 40 mg | PA-101 (30L), 40 mg | PA-101 (30L), 80 mg | Ratio (PA-101 (30L; 40 mg))/ (oral solution, 200 mg)) | Ratio (PA-101 (30L; 40 mg))/ (inhalation aerosol, 20 mg)) |
|---|---|---|---|---|---|---|---|
| $C_{max}$ (ng/mL) | 5.2 (±3.1) | 17.8 (±10.4) | 88.6 (±45.5) | 156 (±104) | 236 (±124) | x30 | x8.8 |
| $T_{max}$ (h) | 3.2 (±2.1) | 0.6 (±0.1) | 0.6 (±0.1) | 0.7 (±0.1) | 0.7 (±0.1) | | |
| $AUC_{0-t}$ (h * ng/mL) | 29.4 (±10.4) | 39.1 (±15.1) | 206 (±94.3) | 329 (±144) | 514 (±186) | x11 | x8.4 |
| $AUC_{(0-\infty)}$ (h * ng/mL) | 33.3 (±11.7) | 40.6 (±15.6) | 212 (±96.0) | 338 (±146) | 526 (±198) | | |
| $T_{1/2}$ (h) | 4.3 (±1.3) | 2.5 (±0.8) | 2.5 (±0.7) | 2.2 (±0.6) | 2.1 (±0.5) | | |
| Bioavailability (%) | 0.6 | 6.5 | 16.3 | 25.0 | 22.7 | x42 | x3.8 |

Values shown in parentheses are (±SD).

Modeling of lung deposition with an aerosol from the 30 L and 40 L devices using the Finlay model (Finlay, W H, and A R Martin, "Recent advances in predictive understanding respiratory tract deposition", Journal of Aerosol Medicine, Vol 21:189-205 (2008)) indicated that the lung deposition with the two devices should be very similar. However, the AUC value obtained with 40 mg dose using the 30 L device (338 ng*hr/mL) was surprisingly high compared to the value (212 ng*hr/mL) from the 40 L device. Cromolyn sodium is not metabolized in the body and is excreted intact via bile and urine. Cromolyn sodium deposited in the lung during inhalation will appear in the plasma, and the AUC would therefore be a surrogate for cromolyn sodium deposited in the lung. Any cromolyn sodium swallowed during inhalation will contribute negligibly to the AUC since the oral bioavailability of cromolyn is only about 1% (Richards et al, J Pharmacol Exp Ther, Vol. 241, No. 3: 1028-1032 (1987)). The AUC data therefore indicate that at the same dose (40 mg), the lung deposition with the 30 L device was surprisingly higher than that with the 40 L device.

The numbers of adverse events observed in the single dose study are shown in the following table:

TABLE 9

| Adverse Event | Placebo | PA-101 (40L), 40 mg | PA-101 (30L), 40 mg | PA-101 (30L), 80 mg | Inhalation aerosol, 20 mg | Oral solution, 200 mg |
|---|---|---|---|---|---|---|
| Cough | 1 | 1 | 0 | 1 | 1 | 0 |
| Oropharyngeal pain | 0 | 0 | 0 | 0 | 1 | 1 |
| Rhinorrhoea | 1 | 0 | 0 | 0 | 0 | 0 |
| Dizziness | 0 | 0 | 2 | 0 | 0 | 0 |
| Headache | 0 | 0 | 0 | 1 | 0 | 1 |
| Dysgeusia | 0 | 0 | 0 | 0 | 0 | 1 |
| Somnolence | 0 | 0 | 0 | 1 | 0 | 0 |
| Catheter-site Reaction | 0 | 0 | 1 | 0 | 0 | 1 |
| Nasopharygitis | 0 | 0 | 0 | 0 | 1 | 0 |
| Sinusitis | 0 | 0 | 0 | 1 | 0 | 0 |
| Abdominal Discomfort | 0 | 0 | 0 | 0 | 0 | 1 |
| Increased Appetite | 0 | 1 | 0 | 0 | 0 | 0 |

Table 10 provides a summary of adverse events observed following treatment with PA101 formulations versus placebo or other available cromolyn formulations.

TABLE 10

Part 1

| | Placebo (30 L) (N = 12) | | 40 mg PA (30 L) (N = 12) | | 80 mg PA (30 L) (N = 12) | | 40 mg PA (40 L) (N = 12) | | 20 mg Intral (LC Plus) (N = 12) | | 200 mg Nalcrom (oral) (N = 12) | |
|---|---|---|---|---|---|---|---|---|---|---|---|---|
| | n | (%) | n | (%) | n | (%) | n | (%) | n | (%) | n | (%) |
| Any AE | 2 | (16.7) | 3 | (25.0) | 4 | (33.3) | 2 | (16.7) | 3 | (25.0) | 2 | (16.7) |
| Any SAE | 0 | (0.0) | 0 | (0.0) | 0 | (0.0) | 0 | (0.0) | 0 | (0.0) | 0 | (0.0) |
| Probably related AE | 0 | (0.0) | 0 | (0.0) | 0 | (0.0) | 1 | (8.3) | 0 | (0.0) | 1 | (8.3) |
| Possibly related AE | 0 | (0.0) | 2 | (16.7) | 2 | (16.7) | 0 | (0.0) | 0 | (0.0) | 0 | (0.0) |
| Unlikely related AE | 1 | (8.3) | 0 | (0.0) | 2 | (10.7) | 1 | (8.3) | 2 | (16.7) | 1 | (8.3) |
| Not related AE | 1 | (8.3) | 1 | (8.3) | 0 | (0.0) | 0 | (0.0) | 1 | (8.3) | 1 | (8.3) |
| Related AE | 0 | (0.0) | 2 | (16.7) | 2 | (16.7) | 1 | (8.3) | 0 | (0.0) | 1 | (8.3) |
| Not related AE | 2 | (16.7) | 1 | (8.3) | 2 | (16.7) | 1 | (8.3) | 3 | (25.0) | 2 | (16.7) |
| Discontinued due to AE | 0 | (0.0) | 0 | (0.0) | 0 | (0.0) | 0 | (0.0) | 0 | (0.0) | 0 | (0.0) |

Example 6: Pharmacokinetics, Relative Bioavailability, and Tolerability Study of Three Different PA101 Formulations in Healthy Subjects (PK-02)

PA101 contains 4% (by weight) cromolyn as the active substance, 0.2% Sodium Chloride as an osmotic agent, 0.02% EDTA as a chelating agent, 1.25% mannitol as a non-ionic osmotic agent, and purified water q.s. PA101 has an osmolality of 200 mOsm/kg. PA101-B contains 4% or 6% (by weight) cromolyn as the active substance, 0.2% sodium chloride as an osmotic agent, 0.02% EDTA as a chelating agent, and purified water q.s. PA101-B (40 mg) has an osmolality of 125 mOsm/kg. PA101-B (60 mg) has an osmolality of 135 mOsm/kg.

A primary objective of the study was to evaluate the pharmacokinetics, relative bioavailability, and tolerability three different PA101 formulations in healthy subjects.

The study was designed as a randomized, double-blind, 4-period cross-over study using 12 healthy volunteers, between 18 and 45 years old.

The treatments given were one of the following: 1) 40 mg PA101 (with mannitol), 2) 40 mg PA101B (no mannitol), 3) 60 mg PA101B (no mannitol), and 4) Placebo TID (no mannitol). All treatments administered three times per day (TID) as a single day treatment. Each study treatment separated by a washout period of minimum 24 hrs. All formulations were administered with a Pari eFlow 30 L device. The placebo contained 0.2% sodium chloride as an osmotic agent, 0.02% EDTA as a chelating agent, and purified water q.s. The osmolality of the placebo was about 65 mOsm/kg.

Study demographics: 13 total subjects, 5 male and 8 female, having a mean age of 28 years old (total range of 21-40 years old).

Disposition: 13 subjects were randomized. 12 subjects completed the study whereas one subject discontinued during the treatment period 1 (subject was receiving placebo) due to an adverse event (a cough that started 1 minute post-dosing and lasted three minutes).

Table 11 provides a summary of the adverse events observed during this study.

TABLE 11

| | PA101 (N = 12) | | PA101-B (40) (N = 12) | | PA101-B (60) (N = 12) | | Placebo (N = 13) | |
|---|---|---|---|---|---|---|---|---|
| | n | (%) | n | (%) | n | (%) | n | (%) |
| Any AE | 5 | (41.7) | 7 | (58.3) | 5 | (41.7) | 7 | (53.8) |
| Any SAE | 0 | (0.0) | 0 | (0.0) | 0 | (0.0) | 0 | (0.0) |
| Probably related AE | 0 | (0.0) | 2 | (16.7) | 1 | (8.3) | 4 | (30.8) |
| Possibly related AE | 0 | (0.0) | 0 | (0.0) | 1 | (8.3) | 1 | (7.7) |
| Unlikely related AE | 1 | (8.3) | 1 | (8.3) | 2 | (16.7) | 1 | (7.7) |
| Not related AE | 5 | (41.7) | 6 | (50.0) | 1 | (8.3) | 2 | (15.4) |
| Related AE* | 0 | (0.0) | 2 | (16.7) | 2 | (16.7) | 4 | (30.8) |
| Not related AE* | 5 | (41.7) | 6 | (50.0) | 3 | (25.0) | 3 | (23.1) |
| Discontinued due to AE | 0 | (0.0) | 0 | (0.0) | 0 | (0.0) | 1 | (7.7) |
| Concomitant medication given | 2 | (16.7) | 2 | (16.7) | 0 | (0.0) | 0 | (0.0) |
| AE of mild intensity | 5 | (41.7) | 7 | (58.3) | 5 | (41.7) | 7 | (53.8) |
| AE of moderate intesity | 2 | (16.7) | 2 | (16.7) | 0 | (0.0) | 2 | (15.4) |
| AE severe intensity | 0 | (0.0) | 0 | (0.0) | 0 | (0.0) | 0 | (0.0) |

Tables 12A and 12B provide an accounting of all adverse events observed during this study.

TABLE 12A

| System Organ Class<br>Preferred term | PA101<br>(N = 12) n | (%) | PA101-<br>B (40)<br>(N = 12) n | (%) | PA101-<br>B (60)<br>(N = 12) n | (%) | Placebo<br>(N = 13) n | (%) |
|---|---|---|---|---|---|---|---|---|
| Number of subject with at least one TEAE | 5 | (41.7) | 7 | (58.3) | 5 | (41.7) | 7 | (53.8) |
| GENERAL DISORDERS AND ADMINISTRATION SITE CONDITIONS | 4 | (33.3) | 2 | (16.7) | 2 | (16.7) | 2 | (15.4) |
| APPLICATION SITE REACTION | 1 | (8.3) | 1 | (8.3) | 1 | (8.3) | 0 | (0.0) |
| FEELING HOT | 0 | (0.0) | 0 | (0.0) | 1 | (8.3) | 0 | (0.0) |
| ASTHENIA | 0 | (0.0) | 0 | (0.0) | 0 | (0.0) | 1 | (7.7) |
| CATHETER SITE PAIN | 1 | (8.3) | 0 | (0.0) | 0 | (0.0) | 1 | (7.7) |
| CATHETER SITE RELATED REACTION | 2 | (16.7) | 1 | (8.3) | 0 | (0.0) | 0 | (0.0) |
| FATIGUE | 0 | (0.0) | 0 | (0.0) | 0 | (0.0) | 1 | (7.7) |
| GASTROINTESTINAL DISORDERS | 0 | (0.0) | 1 | (8.3) | 0 | (0.0) | 2 | (15.4) |
| ABDOMINAL PAIN UPPER | 0 | (0.0) | 0 | (0.0) | 0 | (0.0) | 1 | (7.7) |
| DRY MOUTH | 0 | (0.0) | 1 | (8.3) | 0 | (0.0) | 0 | (0.0) |
| NAUSEA | 0 | (0.0) | 0 | (0.0) | 0 | (0.0) | 1 | (7.7) |
| INVESTIGATIONS | 0 | (0.0) | 1 | (8.3) | 0 | (0.0) | 0 | (0.0) |
| SPUTUM ABNORMAL | 0 | (0.0) | 1 | (8.3) | 0 | (0.0) | 0 | (0.0) |
| MUSCULOSKELETAL AND CONNECTIVE TISSUE DISORDERS | 1 | (8.3) | 0 | (0.0) | 0 | (0.0) | 0 | (0.0) |
| BACK PAIN | 1 | (8.3) | 0 | (0.0) | 0 | (0.0) | 0 | (0.0) |

TABLE 12B

| System Organ Class<br>Preferred term | PA101<br>(N = 12) n | (%) | PA101-<br>B (40)<br>(N = 12) n | (%) | PA101-<br>B (60)<br>(N = 12) n | (%) | Placebo<br>(N = 13) n | (%) |
|---|---|---|---|---|---|---|---|---|
| NERVOUS SYSTEM DISORDERS | 1 | (8.3) | 4 | (33.3) | 3 | (25.0) | 1 | (7.7) |
| DIZZINESS | 1 | (8.3) | 3 | (25.0) | 2 | (16.7) | 1 | (7.7) |
| HEADACHE | 1 | (8.3) | 2 | (16.7) | 2 | (16.7) | 0 | (0.0) |
| RESPIRATORY, THORACIC AND MEDIASTINAL DISORDERS | 0 | (0.0) | 3 | (25.0) | 3 | (25.0) | 4 | (30.8) |
| COUGH | 0 | (0.0) | 0 | (0.0) | 2 | (16.7) | 4 | (30.8) |
| THROAT IRRITATION | 0 | (0.0) | 1 | (8.3) | 1 | (8.3) | 2 | (15.4) |
| NASAL CONGESTION | 0 | (0.0) | 1 | (8.3) | 0 | (0.0) | 0 | (0.0) |
| OROPHARYNGEAL PAIN | 0 | (0.0) | 1 | (8.3) | 0 | (0.0) | 0 | (0.0) |
| SKIN AND SUBCUTANEOUS TISSUE DISORDERS | 1 | (8.3) | 0 | (0.0) | 0 | (0.0) | 1 | (7.7) |
| PETECHIAE | 1 | (8.3) | 0 | (0.0) | 0 | (0.0) | 0 | (0.0) |
| SKIN REACTION | 0 | (0.0) | 0 | (0.0) | 0 | (0.0) | 1 | (7.7) |
| VASCULAR DISORDERS | 1 | (8.3) | 0 | (0.0) | 0 | (0.0) | 0 | (0.0) |
| THROMBOPHLEBITIS | 1 | (8.3) | 0 | (0.0) | 0 | (0.0) | 0 | (0.0) |

Table 13 provides a summary of adverse events observed during this study related to administration of PA101 or PA101-B.

TABLE 13

| System Organ Class<br>Preferred term | PA101<br>(N = 12) n | (%) | PA101-<br>B (40)<br>(N = 12) n | (%) | PA101-<br>B (60)<br>(N = 12) n | (%) | Placebo<br>(N = 13) n | (%) |
|---|---|---|---|---|---|---|---|---|
| Number of subject with at least one TEAE | 0 | (0.0) | 2 | (16.7) | 2 | (16.7) | 4 | (30.8) |
| RESPIRATORY, THORACIC AND MEDIASTINAL DISORDERS | 0 | (0.0) | 1 | (8.3) | 2 | (16.7) | 4 | (30.8) |
| COUGH | 0 | (0.0) | 0 | (0.0) | 1 | (8.3) | 1 | (30.8) |
| THROAT IRRITATION | 0 | (0.0) | 1 | (8.3) | 1 | (8.3) | 2 | (15.4) |
| NERVOUS SYSTEM DISORDERS | 0 | (0.0) | 0 | (0.0) | 1 | (8.3) | 0 | (0.0) |
| DIZZINESS | 0 | (0.0) | 0 | (0.0) | 1 | (3.3) | 0 | (0.0) |
| GASTROINTESTINAL DISORDERS | 0 | (0.0) | 1 | (8.3) | 0 | (0.0) | 1 | (7.7) |
| DRY MOUTH | 0 | (0.0) | 1 | (8.3) | 0 | (0.0) | 0 | (0.0) |
| NAUSEA | 0 | (0.0) | 0 | (0.0) | 0 | (0.0) | 1 | (7.7) |

Table 14 provides a summary of moderate adverse events observed during this study.

TABLE 14

| System Organ Class<br>Preferred term | PA101<br>(N = 12) n | (%) | PA101-<br>B (40)<br>(N = 12) n | (%) | PA101-<br>B (60)<br>(N = 12) n | (%) | Placebo<br>(N = 13) n | (%) |
|---|---|---|---|---|---|---|---|---|
| Number of subject with in least one TEAE | 2 | (16.7) | 2 | (16.7) | 0 | (0.0) | 2 | (15.4) |
| GENERAL DISORDERS AND ADMINISTRATION SITE CONDITIONS | 0 | (0.0) | 1 | (8.3) | 0 | (0.0) | 1 | (7.7) |
| APPLICATION SITE REACTION | 0 | (0.0) | 1 | (8.3) | 0 | (0.0) | 0 | (0.0) |
| CATHETER SITE PAIN | 0 | (0.0) | 0 | (0.0) | 0 | (0.0) | 1 | (7.7) |
| NERVOUS SYSTEM DISORDERS | 1 | (8.3) | 2 | (16.7) | 0 | (0.0) | 0 | (0.0) |
| HEADACHE | 1 | (8.3) | 2 | (16.7) | 0 | (0.0) | 0 | (0.0) |
| RESPIRATORY, THORACIC AND MEDIASTINAL DISORDERS | 0 | (0.0) | 0 | (0.0) | 0 | (0.0) | 1 | (7.7) |
| COUGH | 0 | (0.0) | 0 | (0.0) | 0 | (0.0) | 1 | (7.7) |
| VASCULAR DISORDERS | 1 | (8.3) | 0 | (0.0) | 0 | (0.0) | 0 | (0.0) |
| THROMBOPHLEBITIS | 1 | (8.3) | 0 | (0.0) | 0 | (0.0) | 0 | (0.0) |

Pharmacokinetic Results:

Table 15 provides the mean and standard deviation (SD) for each pharmacokinetic parameter measured for each PA101 formulation studied. As used herein, "$K_{el}$"=is the elimination rate constant that describes the rate at which the cromolyn of PA101 or PA101-B formulations is removed from the subject's system. This measure is equivalent to the fraction of cromolyn that is removed per unit of time ($T^{-1}$, or in this case 1/hours(h)).

TABLE 15

|  | 40 mg PA101 | | 40 mg PA101-B | | 60 mg PA101-B | |
| --- | --- | --- | --- | --- | --- | --- |
| Parameter | Mean | SD | Mean | SD | Mean | SD |
| 1st Dose | | | | | | |
| $C_{max}$, ng/mL | 76.8 | 31.0 | 75.6 | 29.1 | 119 | 41.0 |
| $T_{max}$, $h^a$ | 0.56 (0.31-2.04) | | 0.56 (0.31-2.04) | | 0.56 (0.13-2.04) | |
| $AUC_{0-6}$, h·ng/mL | $229^b$ | $966^b$ | $216^b$ | $797^b$ | $358^b$ | $136^b$ |
| 2nd Dose | | | | | | |
| $C_{max}$, ng/mL | 84.7 | 34.7 | 82.3 | 32.1 | 148 | 60.3 |
| $T_{max}$, $h^a$ | 0.56 (0.23-2.04) | | 0.56 (0.13-2.06) | | 0.56 (0.23-1.04) | |
| $AUC_{0-6}$, h·ng/mL | $266^b$ | $123^b$ | $258^b$ | $101^b$ | 420 | 175 |
| 3rd Dose | | | | | | |
| $C_{max}$, ng/mL | 92.1 | 30.1 | 92.9 | 35.1 | 157 | 58.2 |
| $T_{max}$, $h^a$ | 0.56 (0.23-0.81) | | 0.56 (0.23-2.04) | | 0.56 (0.13-0.56) | |
| $AUC_{0-t}$, h·ng/mL | 330 | 142 | 330 | 140 | 529 | 257 |
| $AUC_{0-inf}$, h·ng/mL | 342 | 147 | 340 | 145 | 542 | 262 |
| $k_{el}$, 1/h | 0.281 | 0.0282 | 0.294 | 0.0229 | 0.306 | 0.0385 |
| $t_{1/2}$, h | 2.49 | 0.237 | 2.37 | 0.184 | 2.30 | 0.265 |

The pharmacokinetic parameters of the PA101 treatments of the study (described in Example 2—PK-01) and the study (described in this Example—PK-02) are compared in Table 16 below. Note that subjects in one of the PK-01, 40 mg group was administered the formulation comprising cromolyn sodium using a Pari eFlow 40 L device, while the formulations were administered to all other subjects in the study using a Pari eFlow 30 L device. In the PK-01 study there were three subjects whose plasma values were very high compared to the average, and these outlier values skewed the Cmax and AUC results in the PK-01 study. If the data are analyzed by excluding these outliers, the Cmax and AUC results of the PK-01 and PK-02 studies are comparable. This was supported by the finding that the urine cromolyn levels were similar in the two studies.

TABLE 16

|  | Intal 20 mg | Nalcrom 200 mg | PK-01 PA101 40 mg (40L) | PK-01 PA101 40 mg (30L) | PK-01 PA101 80 mg (30L) | PK-02 PA101 40 mg (30L) | PK-02 PA101B 40 mg (30L) | PK-02 PA10113 60 mg (30L) |
| --- | --- | --- | --- | --- | --- | --- | --- | --- |
| $C_{max}$ (ng/mL) | 17.8 (10.4) | 5.2 (3.1) | 88.6 (45.5) | 156 (104) | 236 (104) | 76.8 (31.0) | 75.6 (29.1) | 119 (41.0) |
| $T_{max}$ (h) | 0.6 (0.1) | 3.2 (2.1) | 0.6 (0.1) | 0.7 (0.1) | 0.7 (0.1) | 0.6 (0.3) | 0.6 (0.3) | 0.6 (0.1) |
| $AUC_{0-t}$ (h·ng/mL) | 39.1 (15.1) | 29.4 (10.4) | 206 (94.3) | 329 (144) | 514 (186) | 229 (97) | 216 (80) | 358 (136) |
| $AUC_{(0-\infty)}$ (h·ng/mL) | 40.6 (15.6) | 33.3 (11.7) | 212 (96.0) | 338 (146) | 526 (198) | | | |
| $T_{1/2}$ (h) | 2.5 (0.8) | 4.3 (1.3) | 2.5 (0.7) | 2.2 (0.6) | 2.1 (0.5) | | | |

PA101 formulations from the Phase I and Phase II studies are safe and well-tolerated. The most common adverse events, reported in at least 2 subjects, include cough, throat irritation, dizziness, headache and catheter-site reaction. Treatment-related adverse events include cough, throat irritation, dizziness, dry mouth and nausea. Both the frequency and severity of adverse events are comparable between active and placebo treatments, which was unexpected given that the PA101-B formulations (without mannitol) exhibited osmolalities that were significantly different than formulations comprising mannitol. Accordingly, the majority of adverse events have a mild intensity and transient duration.

Thus, the PA101-B formulations (at both 40 mg and 60 mg dosages) are well-tolerated with an adverse event (AE) profile similar to PA101.

PA101-B formulations (at both 40 mg and 60 mg dosages) have a comparable pharmacokinetic profile to PA101.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A method of preventing a decline of forced vital capacity (% PVC) in a subject having idiopathic pulmonary fibrosis, comprising administering to a subject in need thereof a pharmaceutical composition with a high-efficiency nebulizer,
   wherein the pharmaceutical composition comprises from about 1% by weight to about 99% by weight of cromolyn sodium;
   wherein the pharmaceutical composition has an osmolality of between about 120 mOsm/kg and about 140 mOsm/kg,
   wherein the administration of the pharmaceutical composition to the subject produces in the subject an $AUC_{(0-\infty)}$ of cromolyn greater than about 5.3 ng*hr/mL per mg of cromolyn sodium administered to the subject; and
   wherein the pharmaceutical composition does not comprise a sugar alcohol or propylene glycol.

2. The method according to claim 1, wherein the nebulizer, a high-efficiency nebulizer is a vibrating mesh nebulizer.

3. The method according to claim 2, wherein the vibrating mesh nebulizer provides an aerosol of the pharmaceutical composition having a respirable fraction ≤3.3 µm of at least about 30% and a respirable fraction ≤5 µm of at least about 65%.

4. The method according to claim 2, wherein the vibrating mesh nebulizer provides an aerosol of the pharmaceutical composition having a respirable fraction ≤3.3 µm of at least about 45% and a respirable fraction ≤5 µm of at least about 75%.

5. The method according to claim 1, wherein the subject experiences a decline of forced vital capacity (% PVC) of less than about 10% following administration of the pharmaceutical composition to the subject for at least 2 weeks.

6. The method according to claim 1, wherein the subject experiences a decline of forced vital capacity (% PVC) of less than about 9% following administration of the pharmaceutical composition to the subject for at least 2 weeks.

7. The method according to claim 1, wherein the subject experiences a decline of forced vital capacity (% PVC) of less than about 8% following administration of the pharmaceutical composition to the subject for at least 2 weeks.

8. The method according to claim 1, wherein the subject experiences a decline of forced vital capacity (% PVC) of less than about 7% following administration of the pharmaceutical composition to the subject for at least 2 weeks.

9. The method according to claim 1, wherein the subject experiences a decline of forced vital capacity (% PVC) of less than about 6% following administration of the pharmaceutical composition to the subject for at least 2 weeks.

10. The method according to claim 1, wherein the subject experiences a decline of forced vital capacity (% PVC) of less than about 5% following administration of the pharmaceutical composition to the subject for at least 2 weeks.

11. The method according to claim 1, wherein the subject experiences a decline of forced vital capacity (% PVC) of less than about 4% following administration of the pharmaceutical composition to the subject for at least 2 weeks.

12. The method according to claim 1, wherein the subject experiences a decline of forced vital capacity (% PVC) of less than about 3% following administration of the pharmaceutical composition to the subject for at least 2 weeks.

13. The method according to claim 1, wherein the subject experiences a decline of forced vital capacity (% PVC) of less than about 2% following administration of the pharmaceutical composition to the subject for at least 2 weeks.

14. The method according to claim 1, wherein the subject experiences a decline of forced vital capacity (% PVC) of less than about 1% following administration of the pharmaceutical composition to the subject for at least 2 weeks.

15. The method according to claim 1, wherein the subject experiences no decline of forced vital capacity (% PVC) following administration of the pharmaceutical composition to the subject for at least 2 weeks.

16. The method according to claim 1, wherein the pharmaceutical composition comprises about 1%, about 2%, about 3%, about 4%, about 5%, about 6%, about 7%, about 8%, about 9%, about 10%, about 20%, about 30%, about 40%, about 50%, about 60%, about 70%, about 80%, about 90%, or about 99% by weight of cromolyn sodium.

17. The method according to claim 16, wherein the pharmaceutical composition comprises about 2%, about 4%, or about 6% by weight of cromolyn sodium.

18. The method according to claim 2, wherein said pharmaceutical composition further comprises sodium chloride.

19. The method according to claim 2, wherein the pharmaceutical composition does not comprise a non-ionic osmotic agent.

20. The method according to claim 1, wherein the administration of the pharmaceutical composition to the subject produces in the subject a $C_{max}$ of greater than about 1.9 ng/mL per mg of cromolyn sodium administered to the subject.

* * * * *